US011180534B1

(12) United States Patent
Bond et al.

(10) Patent No.: US 11,180,534 B1
(45) Date of Patent: Nov. 23, 2021

(54) COMPOSITIONS AND METHODS FOR TREATING SARS-COV-2 INFECTIONS

(71) Applicant: MOREHOUSE SCHOOL OF MEDICINE, Atlanta, GA (US)

(72) Inventors: Vincent C. Bond, Stone Mountain, GA (US); Ming Bo Huang, Atlanta, GA (US); James W. Lillard, Jr., Smyrna, GA (US)

(73) Assignee: MOREHOUSE SCHOOL OF MEDICINE, Atlanta, GA (US)

( * ) Notice: Subject to any disclaimer, the term of this patent is extended or adjusted under 35 U.S.C. 154(b) by 0 days.

(21) Appl. No.: 17/339,197

(22) Filed: Jun. 4, 2021

(51) Int. Cl.
| | | |
|---|---|---|
| C07K 14/16 | (2006.01) | |
| A61K 47/54 | (2017.01) | |
| A61K 45/06 | (2006.01) | |
| A61P 31/14 | (2006.01) | |
| A61K 47/60 | (2017.01) | |
| A61K 38/00 | (2006.01) | |

(52) U.S. Cl.
CPC ............ *C07K 14/163* (2013.01); *A61K 45/06* (2013.01); *A61K 47/542* (2017.08); *A61K 47/60* (2017.08); *A61P 31/14* (2018.01); *A61K 38/00* (2013.01)

(58) Field of Classification Search
CPC ...... C07K 14/163; A61K 47/60; A61K 45/06; A61K 47/542; A61K 38/00; A61P 31/14
See application file for complete search history.

(56) References Cited

U.S. PATENT DOCUMENTS

| | | | |
|---|---|---|---|
| 4,569,789 A | 2/1986 | Blattler et al. | |
| 4,631,190 A | 12/1986 | Shen et al. | |
| 5,252,714 A | 10/1993 | Harris et al. | |
| 5,306,809 A | 4/1994 | Boon et al. | |
| 5,560,234 A | 10/1996 | Ross et al. | |
| 5,665,358 A | 9/1997 | Barton et al. | |
| 5,672,662 A | 9/1997 | Harris et al. | |
| 5,985,263 A | 11/1999 | Lee et al. | |
| 5,990,237 A | 11/1999 | Bentley et al. | |
| 8,431,530 B2 | 7/2013 | Bond et al. | |
| 10,040,831 B2 | 8/2018 | Bond et al. | |
| 10,544,193 B2 * | 1/2020 | Bond ...................... | A61K 38/16 |
| 10,800,817 B2 | 10/2020 | Bond et al. | |
| 2004/0192627 A1 | 9/2004 | Weissig et al. | |
| 2012/0121507 A1 | 5/2012 | Filfil et al. | |
| 2012/0171115 A1 | 7/2012 | Hudson et al. | |
| 2014/0142121 A1 | 5/2014 | Altieri et al. | |
| 2014/0196172 A1 | 7/2014 | Eudes et al. | |
| 2016/0237129 A1 | 8/2016 | Keefe et al. | |

OTHER PUBLICATIONS

Riva et al. Discovery of SARS-CoV-2 antiviral drugs through large-scale compound repurposing. Nature, Oct. 2020, vol. 586, No. 7827, pp. 113-119. (Year: 2020).*
Barberis et al. Circulating Exosomes Are Strongly Involved in SARS-CoV-2 Infection. Frontiers in Molecular Biosciences. Feb. 22, 2021, vol. 8, Article 632290, pp. 1-18. (Year: 2021).*
Inagawa et al. Novel ACE2-IgG1 fusions with improved in vitro and in vivo activity against SARS-CoV2, bioRxiv, Jul. 24, 2020, 21 pages. (Year: 2020).*
Guy, B. et al., "Mutational analysis of the HIV nef Protein", Virology, 1990, vol. 176, pp. 413-425.
Campbell, T. D. et al., "HIV-1 Nef protein is secreted into vesicles that can fuse with target cells and virions", Ethnicity & Disease, 2008, vol. 18(2), pp. S2-14-S2-19.
Sanfridson, A. et al., "Nef proteins encoded by human and simian immunodeficiency viruses induce the accumulation of endosomes and lysosomes in human T cells", Proc. Natl. Acad. Sci., 1997, vol. 94(3), pp. 873-838.
Esser, M. T. et al., "Differential Incorporation of CD45, CD80 (B7-1), CD86 (B7-2), and Major Histocompatibility Complex Class I and II Molecules into Human Immunodeficiency Virus Type 1 Virions and Microvesicles: Implications for Viral Pathogenesis and Immune Regulation", Journal of Virology, 2001, vol. 75(13), pp. 6173-6182.
Joliot, A. et al., "Transduction peptides: from technology to physiology", Nature Cell Biology, 2004, vol. 6(3), pp. 189-196.
Heitz, F. et al., "Twenty years of cell-penetrating peptides: from molecular mechanisms to therapeutics", British Journal of Pharmacology, 2009, vol. 157(2), pp. 195-206.
Gaertner, H. F. et al., "Site-specific attachment of functionalized poly(ethylene glycol) to the amino terminus of proteins", Bioconjugate Chem., 1996, vol. 7(1), pp. 38-44.
Ali, S. A. et al., "Genetic Characterization of HIV Type 1 Nef-Induced Vesicle Secretion", AIDS Research and Human Retroviruses, 2010, vol. 26(2), pp. 173-192.
Ellman, G. L. et al., "A new and rapid colorimetric determination of acetylcholinesterase activity", Biochemical Pharmacology, 1961, vol. 7, pp. 88-95.
Shelton, M. N. et al., "Secretion Modification Region-Derived Peptide Disrupts HIV-1 Net's Interaction with Mortalin and Blocks Virus and Nef Exosome Release", Journal of Virology, 2012, vol. 86(1), pp. 406-419.

* cited by examiner

*Primary Examiner* — Marcela M Cordero Garcia
(74) *Attorney, Agent, or Firm* — Ping Wang; Morris, Manning & Martin LLP

(57) ABSTRACT

The present application relates to methods and compositions and methods for treating viral infections, especially those caused by SARS-CoV-2. In one aspect, a method of treatment comprises administering to a subject in need of such treatment an effective amount of a pharmaceutical composition comprising a multipartite SARS-CoV-2-inhibiting peptide comprising a secretion modulating region (VI-SMR) peptide from HIV-1 Nef in combination with a cell-penetrating peptide (CPP) domain, a Clusterin (Clu)-binding peptide (Clu-BP) domain, a mitochondrial targeting (Mito-T) peptide domain, an anti-fusogenic (AF) peptide domain, a viral attachment inhibitor (VAI) domain or combination thereof, optionally where the SARS-CoV-2-inhibiting peptide is pegylated and/or modified with one or more hydrophobic domains.

12 Claims, 9 Drawing Sheets

Specification includes a Sequence Listing.

COMPOSITIONS AND METHODS FOR TREATING SARS-COV-2 INFECTIONS

FIELD

The present application generally relates to methods for treating viral infections. More particularly, the present application relates to an antiviral composition comprising a multipartite virus inhibiting secretion modulating region (VI-SMR) peptide for treatment and prevention of SARS-CoV-2 viral infections.

BACKGROUND

Extracellular vesicles (EVs) are bioactive, small membrane vesicles (30-100 nm). They are released via fusion of multi vesicular bodies (MVBs), derived from multivesicular endosomes, with the plasma membrane leading to release of EVs, such as exosomes, into the extracellular medium. EVs contain microRNAs, mRNAs, DNA fragments, lipids and proteins which can be shuttled from a donor cell to recipient cells. EVs are produced by cells, from intracellular compartments through fusion with the cytoplasmic membrane of a cell, resulting in their release into the extracellular biological fluids of an organism or into cell culture media.

EV release has been demonstrated from different cell types in varied physiological contexts. Virus-infected cells, including those infected by HIV are known to release Nef-containing exosomes (Guy et al., (1990) Virology 176, 413-425; and Campbell et al., (2008) Ethn. Dis. 18, S2-S9), which serve to suppress the immune system allowing HIV to survive. Importantly, EV secretion has been shown to utilize the same endosomal trafficking pathway involved in virion release from infected cells (Sanfridson et al., (1997) Proc. Natl. Acad. Sci. U.S.A 94, 873-878; and Esser et al., (2001) J Virol. 75, 6173-6182).

Recent studies have demonstrated that uptake into cells of peptide antagonists from the Secretion Modification Region (SMR) of HIV-1 Nef protein causes the peptide antagonists to interact with at least four SMR-specific cellular binding proteins, including mortalin, and block EV secretion from cells. Mortalin (GRP75/HSP9A) is primarily a mitochondrial protein, but is also found in the endoplasmic reticulum, cytoplasm and cytoplasmic vesicles. Mortalin expression is low or undetectable in normal unstressed cells. Mortalin is a mitochondrial chaperone and a member of the heat shock protein (Hsp) family, which plays a significant role in maintaining mitochondrial function. As such, mortalin participates in a cell's response to stress and plays a role in mitochondrial import, intracellular trafficking, and cell proliferation. In addition, mortalin binds to complement C9 and plays a role in resistance to complement-dependent cytotoxicity (CDC).

During viral infection, large amounts of viral proteins are rapidly synthesized, whereby protein folding may be a limiting step. Most viruses exploit cellular chaperone proteins not only to facilitate the folding of their own proteins, but also for the regulation of cellular processes to create a favorable environment for their proliferation. For example, the heat shock protein 70 family of chaperones regulates all phases of the Enterovirus A71 life cycle and mortalin (HSPA9) plays a particularly significant role in its life cycle (Su et al., Front. Microbiol. Vol. 11, Article 1656, doi: 10.3389/micb.2020.01656).

The recent SARS-CoV-2 (or COVID-19) pandemic has become one of the biggest public health challenges in history, with the virus having infected over 119 million individuals world-wide, including 223 countries/areas/territories, and claiming more than 2.6 million lives (WHO Situation report; Mar. 14, 2021). Similar to many other viruses, SARS-CoV-2 utilizes exosomal and extracellular vesicle cellular transport avenues for reproduction and intra-host spreading as a mode of systemic virus dissemination.

Emerging evidence has implicated the involvement of EVs, including exosomes, in the pathogenesis of infectious diseases induced by RNA viruses, such as SARS-CoV-2 (reviewed in Xia et al., Fundamental Research, Feb. 26, 2012, doi:10.1016/j.fmre.2021.02.005). EVs can transfer viral receptors (e.g., ACE2 and CD9) to recipient cells to facilitate viral infection, directly transport infectious viral particles to adjacent cells for virus spreading, and mask viruses with host structures to escape immune surveillance. EVs may also mediate cell entry of SARS-CoV-2 through CD9, an EV-enriched tetraspanin, since CD9 and TMPRSS2 work together in cleaving the S protein of MERS coronavirus to facilitate a quick viral entry. Recent studies indicated that circulating exosomes are strongly modulated during COVID-19 infection and are involved in the spread of infection in a host. A proteomic analysis of patient-derived exosomes identified several molecules involved in the immune response, inflammation, and activation of the coagulation and complement pathways, which are the main mechanisms of COVID-19-associated tissue damage and multiple organ dysfunctions (Barberis et al., Front. Mol. Biosci., Vol. 8, Article 632290, Feb. 22, 2021).

Presently, there are few FDA approved antiviral agents showing efficacy for treatment or prevention of coronavirus infections, such as SARS-CoV-2. In view of the outbreak and its toll on human lives, there is a need for improved therapeutic options for treating coronavirus infections, especially those caused by SARS-CoV-2. The present application provides therapeutic SMR-peptide based agents for treatment of SARS-CoV-2 infections and other viral infections where EVs are released.

SUMMARY

The present application relates to compositions and methods for treating, preventing or reducing symptoms of viral infections, such as those caused by SARS-CoV-2.

In one aspect, a composition for treating viral infections comprises a multipartite virus-inhibiting secretion modulating region (VI-SMR) peptide comprising a secretion modifying region (SMR) peptide from HIV-1 Nef; a cell-penetrating peptide (CPP), Clusterin-binding peptide (Clu-BP), or both; and a mitochondrial targeting (Mito-T) peptide, anti-fusogenic (AF) peptide, viral attachment inhibitor (VAI) peptide, or combination thereof.

In another aspect, a method for treating a viral infection comprises administering to a subject in need of such treatment an effective amount of a pharmaceutical composition comprising a multipartite virus-inhibiting secretion modulating region (VI-SMR) peptide. In one embodiment, the VI-SMR peptide comprises an SMR peptide from HIV-1 Nef in combination with a CPP, Clu-BP, or both, wherein the VI-SMR peptide further comprises a Mito-T peptide, an AF peptide, a VAI peptide, or any combination thereof.

In one embodiment, a method for preventing or reducing the severity of chronic immune activation (CIA) comprises administering to a virus-infected patient (e.g., infected with HIV or SARS-CoV-2) an effective amount of a pharmaceutical composition comprising a multipartite virus-inhibiting secretion modulating region (VI-SMR) peptide. In one embodiment, the VI-SMR peptide comprises an SMR peptide from HIV-1 Nef in combination with a CPP, Clu-BP, or both, wherein the VI-SMR peptide further comprises a Mito-T peptide, an AF peptide, a VAI peptide, or any combination thereof.

In another embodiment, a method for treating a SARS-CoV-2 infection comprises administering to a subject infected with SARS-CoV-2 an effective amount of a pharmaceutical composition comprising a VI-SMR peptide comprising an SMR peptide from HIV-1 Nef in combination with a CPP, a Clu-BP, or both, where the VI-SMR peptide further comprises an anti-SARS-CoV-2 AF peptide, an anti-SARS-CoV-2 VAI peptide, or both.

In another embodiment, a method for reducing viral load in a SARS-CoV-2 infected patient comprises administering an effective amount of a pharmaceutical composition comprising a VI-SMR peptide comprising an SMR peptide from HIV-1 Nef in combination with a CPP, a Clu-BP, or both, where the VI-SMR peptide further comprises an anti-SARS-CoV-2 AF peptide, an anti-SARS-CoV-2 VAI peptide, or both, where the treatment results in at least a 2 or 3 $\log_{10}$ reduction in viral RNA copies per mg of lung tissue compared to a negative control.

In another embodiment, a method for preventing or reducing the severity of cytokine storm in a SARS-CoV-2 infected patient comprises administering an effective amount of a pharmaceutical composition comprising a VI-SMR peptide comprising an SMR peptide from HIV-1 Nef in combination with a CPP, a Clu-BP, or both, where the VI-SMR peptide further comprises an anti-SARS-CoV-2 AF peptide, an anti-SARS-CoV-2 VAI peptide, or both, where the treatment results in a reduction of at least 10%, 20%, 50% or 80% in cytokine levels for one or more of IL-6, IL-1β, IL-2, IL-10, IFN-γ, TNF-α, GM-CSF, or VEGF.

In another aspect, the method for treating a SAR-CoV-2 infection comprises administering to a subject infected with SARS-CoV-2 an effective amount of a pharmaceutical composition comprising a mortalin inhibitor in combination with an anti-SARS-CoV-2 peptide, wherein the anti-SARS-CoV-2 peptide comprises an anti-SARS-CoV-2 AF peptide or an anti-SARS-CoV-2 VAI peptide, optionally where the AF peptide and the VAI peptide are administered independently or as a single peptide.

In another embodiment, the method for treating a SARS-CoV-2 infection comprises administering to a subject infected with SARS-CoV-2 an effective amount of a pharmaceutical composition comprising a mortalin inhibitor in combination with an anti-SARS-CoV-2 peptide, a VI-SMR peptide, or both, where the anti-SARS-CoV-2 peptide comprises a CPP, Clu-BP, or both, optionally where the AF peptide and the VAI peptide are administered independently or as a single peptide, or are administered in combination with the VI-SMR peptide, or where the anti-SARS-CoV-2 peptide and the VI-SMR peptide are administered as a single peptide.

In another embodiment, a method for treating a virus infection comprises administering to a subject infected with a virus an effective amount of a pharmaceutical composition comprising a VI-SMR peptide comprising an SMR peptide from HIV-1 Nef in combination with a CPP, Clu-BP, or both, where the VI-SMR peptide further comprises a Mito-T peptide, an AF peptide, a VAI peptide, or a combination thereof.

In some embodiments, the SMR peptide includes the amino acid sequence of VGFPV (SEQ ID NO: 1), VGFPVAAVGFPV (SEQ ID NO: 2), VGFPVAAVGFPVGRKKRRQRRRPPQ (SEQ ID NO: 4), or VGFPVAAVGFPVAAHPLSKHPYWSQPAAHPLSKHPYWSQP (SEQ ID NO: 48).

In some embodiments, the VI-SMR peptide is pegylated.
In some embodiments, the VI-SMR peptide is conjugated to a fatty acid.
In some embodiments, wherein the VI-SMR peptide is pegylated and conjugated to a fatty acid.
In some embodiments, the pharmaceutical composition contains a dimeric or multimeric VI-SMR peptide.
In some embodiments, the method further comprises administration of one or more antiviral agents.
In some embodiments, the VI-SMR peptide is incorporated into, onto, or otherwise associated with a nanoparticle.
In some embodiments, the VI-SMR peptide is loaded into an exosome that is administered into the subject infected with SARS-CoV-2.

In another aspect, the present application provides polynucleotide encoding any of the VI-SMR peptides and/or the anti-SARS-CoV-2 peptides described herein. In certain particular embodiments, an expression vector comprising the polynucleotide is operably linked to a regulatory sequence. In another embodiment, the present application provides an exosome loaded with a VI-SMR peptide described herein. In another embodiment, the present application provides an exosome comprising the expression vector.

BRIEF DESCRIPTION OF THE DRAWINGS

The above and other objects and advantages of the application will be apparent upon consideration of the following detailed description, taken in conjunction with the accompanying figures and paragraphs. The following are brief descriptions of the drawings herein, which illustrate certain aspects and embodiments of the present application, but are not considered limiting in any way.

Figure 1:
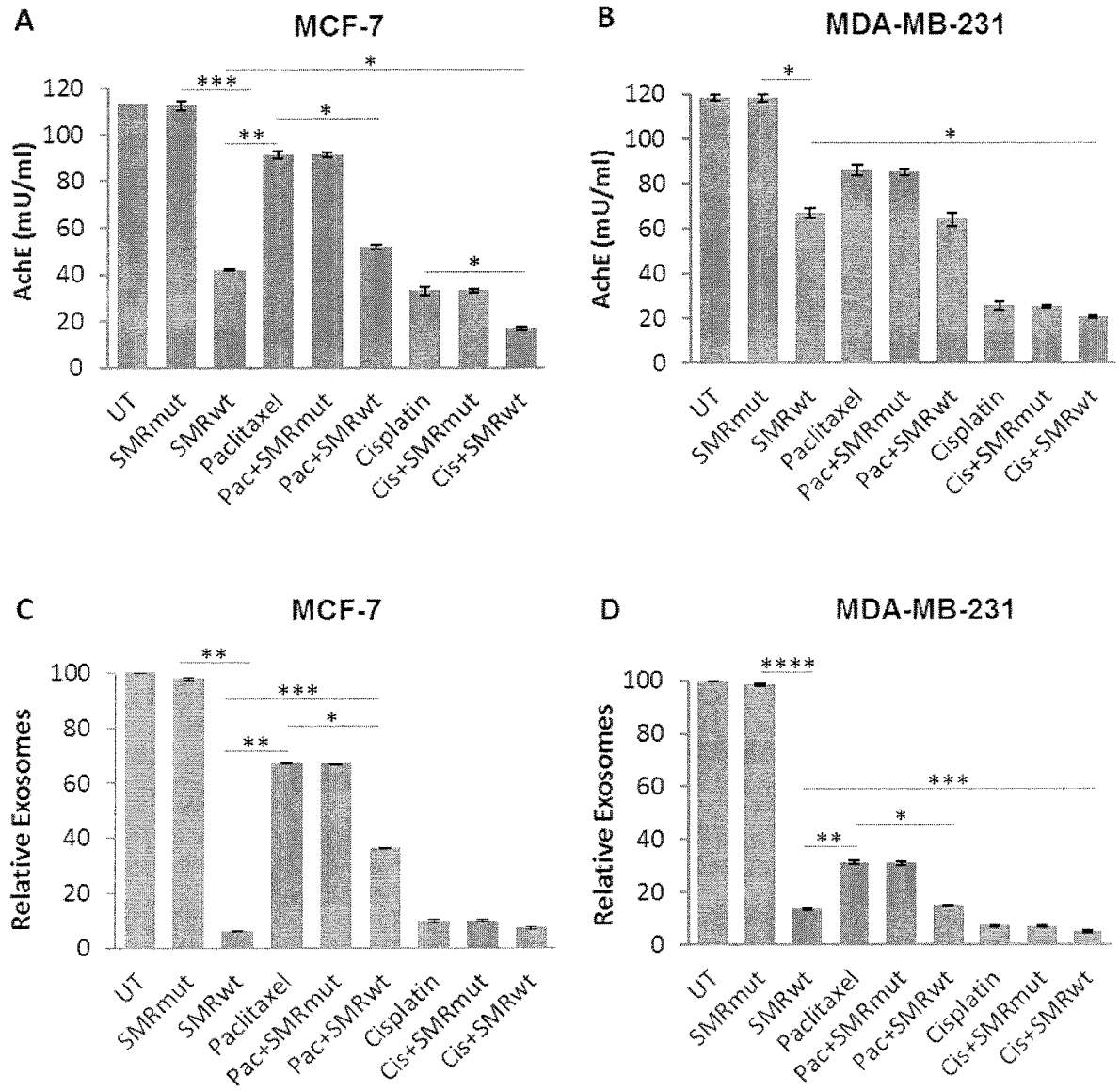
FIG. 1 that PEG-SMRwt-CLU peptide antagonist blocks exosome release from MCF-7 and MDA-MB-231 cells. Cells were treated for 48 hr with peptide alone or combined with paclitaxel or cisplatin. Panels A and B show relative level of exosomes released from MCF-7 and MDA-MB-231 cells respectively, determined by AchE assay. Error bars represent mean+SD of four independent experiments. Significant differences relative to SMRwt peptide: *p<0.01, p<0.001, *p<0.0001 for MCF-7 cells; and*p<0.01 for MDA-MB-231 cells. Panels C and D show relative numbers of exosomes released by MCF-7 and MDA-MB-231 cells respectively, as determined by Nanosight measurement. Error bars represent mean+SD of two independent experiments. Significant differences relative to SMRwt peptide: *p<0.01, p<0.001, *p<0.0001 for MCF-7 cells and *p<0.03, p<0.02, *p<0.01 and****p<0.001 on MDA-MB-231 cells.

While the present disclosure will now be described in detail, and it is done so in connection with the illustrative embodiments, it is not limited by the particular embodiments illustrated in the figures and the appended claims.

DETAILED DESCRIPTION

The disclosure and accompanying drawings will now be discussed to enable one skilled in the art to practice the invention described herein. The skilled artisan will understand, however, that the embodiments described below can be practiced without employing every specific detail, or that they can be used for purposes other than those described herein. Indeed, they can be modified and can be used in conjunction with products and techniques known to those of skill in the art considering the present disclosure. The drawings and descriptions are intended to be exemplary of various aspects of the disclosure and are not intended to narrow the scope of the appended claims. Furthermore, it will be appreciated that the drawings may show aspects of the disclosure in isolation and the elements in one figure may be used in conjunction with elements shown in other figures.

It will be appreciated that reference throughout this specification to aspects, features, advantages, or similar language does not imply that all the aspects and advantages may be realized with the present disclosure or realized in any single embodiment of the disclosure. Rather, language referring to the aspects and advantages should be understood to mean that a specific aspect, feature, advantage, or characteristic described in connection with an embodiment is included in at least one embodiment of the present disclosure. Thus, discussion of the aspects and advantages, and similar language, throughout this specification may, but do not necessarily, refer to the same embodiment.

The described aspects, features, advantages, and characteristics of the disclosure may be combined in any suitable manner in one or more further embodiments. Furthermore, one skilled in the relevant art will recognize that the embodiments may be practiced without one or more of the specific aspects or advantages of a particular embodiment. In other instances, additional aspects, features, and advantages may be recognized and claimed in certain embodiments that may not be present in all embodiments of the disclosure.

Unless otherwise defined, all technical and scientific terms used herein have the same meaning as commonly understood by one of ordinary skill in the art to which this application belongs. One of skill in the art will recognize many techniques and materials similar or equivalent to those described here, which could be used in the practice of the aspects and embodiments of the present application. The described aspects and embodiments of the application are not limited to the methods and materials described.

As used in this specification and the appended claims, the singular forms "a," "an" and "the" include plural referents unless the content clearly dictates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to "the value," greater than or equal to the value" and possible ranges between values are also disclosed, as appropriately understood by the skilled artisan. For example, if the value "10" is disclosed the "less than or equal to 10" as well as "greater than or equal to 10" is also disclosed.

The term "SMR peptide" refers to a peptide of less than 100 amino acids in length comprising one or more copies of the amino acid sequence, VGFPV (SEQ ID NO: 1). In some embodiments, the SMR peptide of less than 100 amino acids in length includes an amino acid sequence from an HIV Nef protein comprising at least one VGFPV (SEQ ID NO: 1) sequence. The term "SMRmut peptide" refer to a peptide less than 100 amino acids in length comprising one or more copies of a mutated SMR peptide sequence that abolishes the functional ability of an SMRwt peptide. Exemplary SMR peptides include VGFPV (SEQ ID NO: 1), VGFPVAAVGFPV (SEQ ID NO: 2) and VGFPVAAVGFPVGRKKRRQRRRPPQ (SEQ ID NO: 4). Exemplary SMRmt peptides include AGFPV (SEQ ID NO: 51), AGFPVAAAGFPV (SEQ ID NO: 52) and AGFPVAAAGFPVGRKKRRQRRRPPQ (SEQ ID NO: 50).

The term "anti-SARS-CoV-2 peptide", refers to a SARS-2 anti-fusogenic peptide or a SARS-2 attachment inhibitor peptide as described herein below.

The term "lipopeptide" refers to a peptide of two or more amino acids that is conjugated to one or more hydrophobic moieties. The lipopeptide may exhibit an anti-fusogenic and/or anti-viral activity if the level of membrane fusion events is lower in the presence of the lipopeptide than in its absence.

The term "hydrophobic" refers to the tendency of chemical moieties with nonpolar atoms to interact with each other rather than water or other polar atoms. Materials that are "hydrophobic" are, for the most part, insoluble in water. Non limiting examples of natural products with hydrophobic properties include lipids, fatty acids, phospholipids, sphingolipids, acylglycerols, waxes, sterols, steroids, terpenes, prostaglandins, thromboxanes, leukotrienes, isoprenoids, retinoids, biotin, and hydrophobic amino acids such as tryptophan, phenylalanine, isoleucine, leucine, valine, methionine, alanine, proline, and tyrosine. A chemical moiety is also hydrophobic or has hydrophobic properties if its physical properties are determined by the presence of nonpolar atoms. The term also includes lipophilic groups.

The term "lipophilic group" refers to a group having high hydrocarbon content thereby giving the group high affinity to lipid phases. A lipophilic group can be, e.g., a relatively long chain alkyl or cycloalkyl (preferably n-alkyl) group having approximately 6 to 30 carbons. The alkyl group may terminate with a hydroxyl, primary amine or any other reactive group. Exemplary lipophilic molecules include naturally-occurring and synthetic aromatic and non-aromatic moieties such as fatty acids, esters, alcohols, other lipid molecules, cage structures, such as adamantane, and aromatic hydrocarbons, such as benzene, perylene, phenanthrene, anthracene, naphthalene, pyrene, chrysene, and naphthacene.

The term "aliphatic", "aliphatic group" or "aliphatic chain" refers to a straight-chain (i.e., unbranched) or branched, substituted or unsubstituted hydrocarbon chain that is completely saturated or that contains one or more unsaturated bonds. Unless otherwise specified, aliphatic groups contain at least aliphatic carbon atoms. In some embodiments, aliphatic groups contain between 6 and 30 aliphatic carbon atoms. In other embodiments, aliphatic groups contain at least 8 aliphatic carbon atoms. In other embodiments, aliphatic groups contain at least 10 aliphatic carbon atoms. In still other embodiments, aliphatic groups contain at least 12 aliphatic carbon atoms, and in yet other embodiments aliphatic groups contain at least 16 aliphatic carbon atoms. Suitable aliphatic groups include, but are not limited to, linear or branched, substituted or unsubstituted alkyl, alkenyl, alkynyl, and heteroalkyl groups.

The terms "anti-fusogenic" and "cell fusion inhibitor", as used herein, refer to an agent's ability to inhibit or reduce the level of membrane fusion events between two or more moieties relative to the level of membrane fusion which occurs between these moieties in the absence of e.g., a lipopeptide conjugated to the peptides of the present application. When used in the context of the antiviral peptides described herein, the term "anti-viral" refers to the peptide's ability to inhibit viral infection of cells, via, for example, cell-cell fusion or free virus infection. Such infection may involve membrane fusion, as occurs in the case of enveloped viruses, or some other fusion event involving a viral structure and a cellular structure (e.g., such as the fusion of a viral pilus and bacterial membrane during bacterial conjugation).

The phrase "antiviral agent" refers to a small molecule, protein or antibody that can inhibit the progression of coronavirus infections or induce or mediate the death (e.g., necrosis or apoptosis) of coronavirus-infected cells in a subject (e.g., a human).

The term "small molecule" refers to an organic or inorganic molecule that is not a polymer, that has medicinal activity, and that has a molecular weight less than about 2 kDa, less than about 1 kDa, less than about 900 Da, less than about 800 Da or less than about 700 Da. The term encompasses most medicinal compounds termed "drugs" other than protein or nucleic acids, although a small molecule peptide or nucleic acid analog can be considered a "small molecule". Small molecules drugs can be derived synthetically, semi-synthetically (i.e., from naturally occurring precursors), or biologically.

The term "nanoparticle" refers to any particle having an average diameter of less than 500 nanometers (nm). In some embodiments, nanoparticles have an average diameter of less than 300 nm, less than 100 nm, less than 50 nm, less than 25 nm, less than 10 nm or less than 5 nm. In some embodiments, each nanoparticle has a diameter of less than 300 nm, less than 100 nm, less than 50 nm, less than 25 nm, less than 10 nm or less than 5 nm.

The terms "treat" and "treatment" refer to the amelioration of one or more symptoms associated with a corona virus infection; prevention or delay of the onset of one or more symptoms of a coronavirus infection; and/or lessening of the severity or frequency of one or more symptoms of the infection.

The phrases "to a patient in need thereof", "to a patient in need of treatment" or "a subject in need of treatment" includes subjects, such as mammalian subjects, that would benefit from administration of the VI-SMR peptide and/or other therapeutic agent(s) of the present disclosure for treatment of a viral infection.

The phrases "therapeutically effective amount", "pharmacologically effective amount", and "physiologically effective amount" are used interchangeably to mean the amount of a VI-SMR peptide and/or other therapeutic agent(s) that are needed to provide a threshold level of active antagonist agents in the bloodstream or in the target tissue. The precise amount will depend upon numerous factors, e.g., the particular active agent, the components and physical characteristics of the composition, intended patient population, patient considerations, and the like, and can readily be determined by one skilled in the art, based upon the information provided herein or otherwise available in the relevant literature.

The phrase "cytokine storm" refers to an excessively activated cytokine cascade or hypercytokinemia, i.e., an excessive or uncontrolled release of proinflammatory cytokines, which can be associated with a wide variety of infectious and noninfectious diseases or disorders.

The phrases "pharmaceutical composition comprises" and "pharmaceutical composition comprising" should be interpreted such that the "comprises" or "comprising" components are included in a single pharmaceutical composition or in one or more independent pharmaceutical compositions.

The terms, "improve", "increase" or "reduce", as used in this context, indicate values or parameters relative to a baseline measurement, such as a measurement in the same individual prior to initiation of the treatment described herein, or a measurement in a control individual (or multiple control individuals) in the absence of the treatment described herein.

The term "control individual" is an individual who is not afflicted with the same viral infection as the individual being treated, who is about the same age as the individual being treated (to ensure that the stages of the disease in the treated individual and the control individual(s) are comparable). The individual (also referred to as "patient" or "subject") being treated may be a fetus, infant, child, adolescent, or adult human.

Compositions and Methods of Treatment

The present application relates to compositions and methods for preventing or reducing symptoms of viral infections, including SARS-CoV-2 infections.

In one aspect, a composition for treating viral infections comprises a multipartite virus-inhibiting secretion modulating region (VI-SMR) peptide comprising a secretion modifying region (SMR) peptide from HIV-1 Nef; a cell-penetrating peptide (CPP), Clusterin-binding peptide (Clu-BP), or both. In another embodiment, the VI-SMR peptide further comprises a mitochondrial targeting (Mito-T) peptide, anti-fusogenic (AF) peptide, viral attachment inhibitor (VAI) peptide, or combination thereof.

In another embodiment, the present application provides an exosome comprising an expression vector encoding a VI-SMR peptide and/or an anti-SARS-CoV-2 peptide. In this case, the expression vector may encode a single peptide comprising the VI-SMR peptide and the anti-SARS-CoV-2 peptide. Alternatively, one or more expression vector(s) may independently express the VI-SMR peptide and the anti-SARS-CoV-2 peptide.

In another aspect, a method for treating a viral infection comprises administering to a subject in need of such treatment an effective amount of a pharmaceutical composition comprising a multipartite virus-inhibiting secretion modulating region (VI-SMR) peptide.

In one embodiment, a method for treating a SARS-CoV-2 infection comprises administering to a subject infected with SARS-CoV-2 an effective amount of a pharmaceutical composition comprising a VI-SMR peptide comprising an SMR peptide from HIV-1 Nef in combination with a CPP, a Clu-BP, or both, where the VI-SMR peptide further comprises an anti-SARS-CoV-2 AF peptide, an anti-SARS-CoV-2 VAI peptide, or both.

In another embodiment, a method for treating a SARS-CoV-2 infection comprises administering to a subject in need of such treatment an effective amount of exosomes loaded with a VI-SMR peptide and/or an anti-SARS-CoV-2 peptide.

In another embodiment, a method for treating a virus infection comprises administering to a subject in need of such treatment an effective amount of a pharmaceutical composition comprising a VI-SMR peptide comprising an SMR peptide from HIV-1 Nef in combination with a CPP, Clu-BP, or both, where the VI-SMR peptide further comprises a Mito-T peptide, an AF peptide, a VAI peptide, or a combination thereof.

In another aspect, a method for treating a SARS-CoV-2 infection comprises administering to a subject in need thereof an effective amount of a pharmaceutical composition comprising a mortalin inhibitor in combination with an anti-SARS-CoV-2 peptide, where the anti-SARS-CoV-2 peptide comprises an anti-SARS-CoV-2 AF peptide or an anti-SARS-CoV-2 VAI peptide, optionally where the AF peptide and the VAI peptide are administered independently or as a single peptide.

In another embodiment, the method for treating a SARS-CoV-2 infection comprises administering to a subject infected with SARS-CoV-2 an effective amount of a pharmaceutical composition comprising a mortalin inhibitor in combination with an anti-SARS-CoV-2 peptide, a VI-SMR peptide, or both, where the anti-SARS-CoV-2 peptide comprises a CPP, Clu-BP, or both, optionally where the AF peptide and the VAI peptide are administered independently or as a single peptide, or are administered in combination with the VI-SMR peptide, or where the anti-SARS-CoV-2 peptide and the VI-SMR peptide are administered as a single peptide.

1. Multipartite Virus Inhibiting Secretion Modulating Region (VI-SMR) Peptides

In one embodiment, the monomeric or multimeric multipartite virus-inhibiting secretion modulating region (VI-SMR) peptide includes at least one secretion modifying region (SMR) peptide from HIV-1 Nef which is fused to at least one cell-penetrating peptide (CPP), at least one Clusterin (Clu)-binding peptide (Clu-BP), or both. In other embodiments, the VI-SMR peptide includes at least one SMR peptide, at least one CPP peptide, at least one Clu-BP peptide, at least one mitochondrial targeting peptide (Mito-T), or a combination thereof. The VI-SMR peptide may include 1, 2, 3, 4, 5, 6, 7, 8, 9, 10, 15 or 20 SMR peptides, CPP peptides, Clu-BP peptides, Mito-T peptides, or any combination thereof.

In some embodiments, the VI-SMR peptide is monomeric. In other embodiments, the VI-SMR peptide is dimeric or multimeric.

The peptide domains described herein may be positioned at the amino-terminal end, the C-terminal end or they may be positioned internally. For example, the VI-SMR peptide may have an SMR peptide domain at its N-terminal end and a CPP peptide domain at its C-terminal end. In other embodiments, the VI-SMR peptide may have a CPP peptide at its N-terminal end and a VI-SMR peptide at its C-terminal end. In addition, any of the peptide domains may be separated from one another by a spacer peptide.

In certain preferred embodiments, the SMR peptide includes the amino acid sequence of VGFPV (SEQ ID NO: 1) or VGFPVAAVGFPV (SEQ ID NO: 2).

The cell-penetrating peptide (CPP) domain enhances the uptake of the VI-SMR peptide into eukaryotic cells. Exemplary CPP domains for use in the present application include, but are not limited to, HIV TAT$_{49-57}$, peptide, HIV TAT$_{48-60}$ peptide (GRKKRRQRRRPPQ; SEQ ID NO: 3), low molecular weight protamine (LMWP) peptide; Chariot™, also known as Pep-1 (Morris et al., Nat. Biotechnol., 19:1173-1176, 2001); Antp43-58 peptide, MPG (HIV Gp41-SV40 NLS), SAP, MPG R9, MAP, K-FGF, Penetratin, Buforin II, Transportan, Ku70, Prion, pVEC, Pep-1-K, Pep-7, HN-1, TP10, and CP26 (See e.g., Joliot et al., Nature Cell Biol., 6(3):189-196, 2004 and Heitz et al., Br. J Pharmacol., 157:195-206, 2009).

The Clusterin (Clu)-binding peptide (Clu-BP) is derived from a molecular chaperone involved in protein secretion. Exemplary Clu-BP peptide domains for use in the present application include, but are not limited an amino acid sequences selected from the group consisting of HPLSKHPYWSQP (SEQ ID NO: 5), NTYWSQLLHFQT (SEQ ID NO: 6) and SHALPLTWSTAA (SEQ ID NO: 7) as described in U.S. Patent Publication No. 2012/0121507. In particular embodiments, the VI-SMR peptide has an amino acid sequence selected from the group consisting of VGFPVAAVGFPVGRKKRRQRRRPPQ (SEQ ID NO: 4), NXNVGFPVAAVGFPV (SEQ ID NO: 32), NXNVGFPVAAVGFPVHPLSKHPYWSQP (SEQ ID NO: 33), VGFPVAAVGFPVHPLSKHPYWSQP (SEQ ID NO: 46), VGFPVAAVGFPVAAHPLSKHPYWSQP (SEQ ID NO: 47) and VGFPVAAVGFPVAAHPLSKHPYWSQPAAHPLSKHPYWSQP (SEQ ID NO: 48).

A VI-SMR peptide of the present application may include one or more mitochondrial targeting (Mito-T) peptides. Mito-T peptides can facilitate uptake of the multipartite VI-SMR peptides into mitochondria, where mortalin is localized. Exemplary mitochondrial targeting peptide sequences include those described in U.S. Patent Publication No. 2004/0192627, including the presequence peptide from nuclear-encoded human cytochrome c oxidase (COX) subunit VIII (MSVLTPLLLRGLTGSARRLPVPRAKIHSL; SEQ ID NO: 8); the amino-terminal leader peptide of the rat ornithine transcarbamylase (OTC) (MLSNLRILLN-KAALRKAHTSMVRNFRYGKPVQC; SEQ ID NO: 9), the presequence peptide of cytochrome oxidase subunit IV (MLSLRQSIRFFKPATRTL; SEQ ID NO: 10); an Antennapedia a-helical domain, such as RQIKIWFQNRRMKWKK (SEQ ID NO: 11); and various mitochondrial targeting peptides described in U.S. Patent Publication No. 2014/0196172, including N-terminal mitochondrial targeting peptides, MFSYLPRYPLRAASARALVRATRPSYRSALL-RYQ (SEQ ID NO: 12), MAAWMRSLFSPLKKLWIRMH (SEQ ID NO: 13), MKLLWRLILSRKW (SEQ ID NO: 14), MWWRRSRTNSLRYT (SEQ ID NO: 15), and MLFRLRRSVRLRGLLA (SEQ ID NO: 16); and the N-terminal mitochondrial targeting peptide MWTLGRRAVAGL-LASPSPAQ (SEQ ID NO: 17) as described in U.S. Patent Publication No. 2016/0237129. Exemplary mitochondrial targeting signal peptide sequences directing proteins or peptides to the mitochondria include RRIV-VLHGYGAVKEVLLNHK (SEQ ID NO: 18), amino acids 74-95 of Rat Cytochrome P450 2E1 (CYP2E1), the cleavable prepiece from the yeast cytochrome c oxidase IV precursor (MLSLRQDIRFFKPATRTLCSSR; SEQ ID NO: 19), the mitochondrial-targeting signal from the PB2 protein of influenza viruses, the import signal contained within heme lyases, and the leader peptide of the mitochondrial matrix enzyme ornithine transcarbamylase (OTC) as described in U.S. Patent Publication No. 2014/0142121.

The VI-SMR peptide may include one or more antiviral peptide domains that function as an anti-fusogenic peptide inhibitor or a viral attachment inhibitor. In certain preferred embodiments, the VI-SMR peptide includes an antiviral anti-fusogenic peptide domain, preferably an anti-fusogenic peptide domain derived from a coronavirus, such as SARS-CoV-2.

Fusion between the viral and target cell membranes is an obligatory step for the infectivity of all enveloped viruses, and blocking this process is a clinically validated therapeutic strategy. Viral fusion is driven by specialized proteins which, although specific to each virus, act through a common mechanism, the formation of a complex between two heptad repeats ("HRs") regions. The HR regions are initially separated in an intermediate termed "prehairpin", which bridges the viral and cell membranes, and then fold onto each other to form a 6-helical bundle ("6HB"), driving the two membranes to fuse. HR-derived peptides can inhibit viral infectivity by binding to the prehairpin intermediate and preventing its transition to the 6HB. The antiviral activity of HR-derived peptides differs considerably among enveloped viruses. For weak inhibitors, potency can be increased by peptide engineering strategies, but sequence-specific optimization is time-consuming.

Accordingly, in some embodiments, the VI-SMR peptide may include an anti-fusogenic peptide domain. In addition, in certain cases it is possible to increase the potency of the fusogenic peptide domains without changing the native sequence by attaching hydrophobic moieties, such as cholesterol groups, to HR containing peptides ("cholesterol-tagging") and/or by combining e.g., cholesterol-tagging with dimerization of the HR-derived sequence as further described below. Conjugation of the hydrophobic moiety to a VI-SMR peptide containing anti-fusogenic peptide domain can enhance the anti-fusogenic activity of such peptides at significantly higher level after conjugation than prior to conjugation. In some embodiments, conjugation of hydrophobic moieties to the VI-SMR peptide can enhance the anti-fusogenic activity by at least 2 fold, at least 10-fold, or at least 20 fold. In addition, conjugation of hydrophobic moieties can provide greater stability and improved half-life in vivo.

Exemplary anti-fusion peptide domain sequences targeting coronaviruses include, but are not limited to, SLDQ-INVTFLDLEYEMKKLEEAIKKLEESYIDLKEL (SEQ ID NO: 20); ISGINASVVNIQKEIDRLNEVAKNLNESL-IDLQEL (SEQ ID NO: 21); ISGINASVVNIQKEIDRLNE-VAKNLNESLIDLQELK (SEQ ID NO: 22); DISGI-NASVVNIQKEIDRLNEVAKNLNESLIDLQEL (SEQ ID NO: 23); residues 1168-1203 of SARS-CoV-2 S-protein for SARS-CoV-2; and residues 1251-1286 of MERS-CoV S protein for MERS-CoV. Non-coronavirus anti-fusion peptide coronavirus peptide domains are described in U.S. Patent Publication Nos. US 2012/0028887 and US 2017/0216448.

In some embodiments, the VI-SMR peptide includes a viral attachment inhibitor (VAI) domain that inhibits viral attachment. Exemplary VAI peptide domains may be derived from coronavirus targeted receptors, such as angiotensin-converting enzyme 2 (ACE2; SARS-CoV-2 receptor), dipeptidyl peptidase 4 (DPP4), and aminopeptidase N (APN), or coronavirus proteins that bind to such receptors, including coronavirus S proteins. Exemplary VAI peptide domain sequences include, but are not limited to, YKYRYL (SEQ ID NO: 24); FLDKFNHEAEDLFYQSSL (SEQ ID NO: 25); EEQAKTFLDKFNHEAEDLFYQSSGLGK-GDFR (SEQ ID NO: 26); GFLYVYKGYQPI (SEQ ID NO: 27); FYTTTGIGYQPY (SEQ ID NO: 28); STSQKSIVAY™ (SEQ ID NO: 29); GGGYSKAQKAQAKQAKQAQKAQ-KAQAK- QAKQAQKAQKAQAKQAKQ (SEQ ID NO: 30); and GSHMGDAQDKLKYLVKQLERALRELKKS-LDELERSLEELEKNPSEDALVENNRLNVEN NKIIV-EVLRIILELAKASAKLA (SEQ ID NO: 31).

The VI-SMR peptide may include a cell targeting domain for targeting the peptide to specific viral attachment sites, including viral receptors (as described above) and other cell surface receptors. The targeting domain may comprise a peptide fused to the VI-SMR peptide or it may comprise a non-peptide-based domain chemically conjugated to or covalently attached to the VI-SMR peptide. Exemplary targeting domains include peptides, small molecules, ligands, antibody fragments, and aptamers. In some embodiments, the targeting domain is present at the C-terminal end of the VI-SMR peptide. In other embodiments, the targeting domain is present at the N-terminal end of the VI-SMR peptide.

The VI-SMR peptide may be linked to an immunoglobulin Fc region. The Fc region can enhance stability and in vivo half-life and can facilitate recruitment of Fc receptor-bearing natural killer cells, macrophages, neutrophils, and mast cells, which can stimulate phagocytic or cytotoxic cells to destroy microbes or infected cells by antibody-mediated phagocytosis or antibody-dependent cell-mediated cytotoxicity.

In preferred embodiments, the VI-SMR peptide of the present disclosure includes one or more spacers between two or more functional domains within the VI-SMR peptide. The spacer is designed to facilitate the independent folding of each domain relative to one another, ensure that the individual domains in the peptide do not interfere with one another and/or increase the flexibility of the protein and facilitate adoption of an extended conformation. In some embodiments, the spacer comprises 1 to 50 amino acids, preferably 2 to 10 amino acids.

In some embodiments, the spacer includes one or more a glycine and/or serine residues to force the spacer to adopt a loop conformation, because the absence of a P-carbon permits the polypeptide backbone to access dihedral angles that are energetically forbidden for other amino acids. In addition, spacers comprising glycine and/or serine have a high freedom degree for linking of two peptides, i.e., they enable the fused proteins to fold and produce functional proteins. Other residues that can enhance stability and folding include the amino acids alanine, proline, lysine, and combinations thereof. In one embodiment, the spacer is an Ala-Ala dipeptide linker. In another embodiment, the spacer has the formula [(Gly)n-Ser/Ala]m, where n is from 1 to 4, inclusive, and m is from 1 to 4, inclusive.

In some embodiments, the spacer is designed so that a decrease in pH causes cleavage of the spacer to thereby release of one or more peptide domains into a target cell. A decrease in pH is implicated in many physiological and pathological processes, such as endosome trafficking and inflammation. The pH drops from a physiological 7.4 to 5-6 in endosomes or 4-5 in lysosomes. Examples of acid sensitive spacer moieties which may be used to target lysosomes or endosomes of virus-infected cells, include those with acid-cleavable bonds such as those found in acetals, ketals, orthoesters, hydrazones, trityls, cis-aconityls, or thiocarbamoyls (see for example, U.S. Pat. Nos. 4,569,789, 4,631,190, 5,306,809, and 5,665,358). Other exemplary acid-sensitive spacer moieties include the dipeptide sequences Phe-Lys and Val-Lys.

Cleavable spacer moieties may be sensitive to biologically supplied cleaving agents that are associated with a particular target cell, for example, lysosomal or virus-associated enzymes. Examples of linking moieties that can be cleaved enzymatically include, but are not limited to, esters and endopeptidase cleavage recognition sites.

In some embodiments, the VI-SMR peptide is incorporated into, onto, or otherwise associated with a nanoparticle.

In some embodiments, the VI-SMR peptide is loaded into an exosome that is administered into the subject infected with SARS-CoV-2.

2. Chemical Modifications in the VI-SMR Peptide

The VI-SMR peptide of the present application can be modified to contain nonproteinaceous moieties, including water-soluble polymers, lipids and fatty acids known in the art and readily available. Non-limiting examples of water soluble polymers include, but are not limited to, polyethylene glycol (PEG), triethylene glycol (TEG), polyvinyl alcohol (PVA), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, polypropylene glycol (PPG) homopolymers, propylene oxide/ethylene oxide co-polymers, polyoxyethylated polyols (e.g., glycerol; POG), polyvinyl alcohol, and mixtures thereof. Polyethylene glycol propionaldehyde may have advantages in manufacturing due to its stability in water.

Pegylation

In some embodiments, the VI-SMR peptide is pegylated. PEGylation is a process for covalently attaching polyethylene glycol polymer chains to another molecule, normally a drug or therapeutic peptide/protein. PEGylation can be achieved by incubation of a reactive derivative of PEG with the VI-SMR peptide. The covalent attachment of PEG to a VI-SMR peptide can "mask" the VI-SMR peptide from the host's immune system (reduced immunogenicity and antigenicity), increase the hydrodynamic size (size in solution) of the VI-SMR peptide which prolongs its circulatory time by reducing renal clearance. PEGylation can also provide water solubility to hydrophobic proteins. Various methods are known in the art for conjugating PEGs to peptides or proteins, as describe in U.S. Patent Publication No. 2012/0171115.

The PEG molecules are typically characterized as having for example from about 2 to about 1000, or from about 2 to about 300 repeating units. For example water-soluble polymers, including but not limited to PEG, poly(ethylene oxide) (PEO), polyoxyethylene (POE), polyvinyl alcohols, hydroxyethyl celluloses, or dextrans, are commonly conjugated to proteins to increase stability or size, etc., of the protein as described in U.S. Patent Publication No. 2012/0171115.

PEG, PEO and POE are oligomers or polymers of ethylene oxide. In the case of PEG, these oligomers or polymers are produced by, e.g., anionic ring opening polymerization of ethylene oxide initiated by nucleophilic attack of a hydroxide ion on the epoxide ring. One of the more useful forms of PEG for protein modification is monomethoxy PEG (mPEG).

Preferred PEGs are monodisperse or polydisperse, preferably monodisperse. The skilled artisan will be aware that PEG can be polydisperse or monodisperse. Polydisperse PEG comprises a mixture of PEGs having different molecular weights. In the case of polydisperse PEGs, reference to a specific molecular weight will be understood to refer to the number average molecular weight of PEGs in the mixture. The size distribution is characterized statistically by its weight average molecular weight (MW) and its number average molecular weight (Mn), the ratio of which is called the polydispersity index (Mw/Mn). MW and Mn are measured, in certain aspects, by mass spectroscopy. Most of the PEG-protein conjugates, particularly those conjugated to PEG larger than 1 kDa, exhibit a range of molecular weights due to a 30 polydisperse nature of the parent PEG molecule. For example, in the case of mPEG2K (Sunbright ME-020HS, NOF), actual molecular masses are distributed over a range of 1.5-3.0 kDa with a polydispersity index of 1.036. Based on the foregoing, the skilled artisan will be aware that monodisperse PEG comprises a mixture of PEGs comprising substantially the same molecular weight. Monodisperse PEGs are commercially available, e.g., from Polypure AS, Norway.

The average or preferred molecular weight of the PEG may range from 500 Da to 200 kDa, from 1 to 100 kDa, from 2 to 50 kDa, from 5 to 25 kDa, or from 5 kDa to 10 kDa, including any integers encompassed within these ranges.

An activated PEG may be used with cyanuric chloride to produce a PEG dichlorotriazine derivative. This derivative can react with multiple functional nucleophilic functional groups, such as lysine, serine, tyrosine, cysteine and histidine. Two widely used forms of PEG used to conjugate to proteins are succinimidyl carbonate PEG and benzotriazole carbonate PEG (BTC-PEG; U.S. Pat. No. 5,560,234). Both of these compounds react preferentially with lysine residues to form carbamate linkages, however are also known to react with histidine and tyrosine. SC-PEG is slightly more resistant to hydrolysis than BTC-PEG.

Another PEG useful for conjugating to proteins is PEG-propionaldehyde (U.S. Pat. No. 5,252,714). An advantage of this chemistry is that under acidic conditions (about pH5) it is largely selective for N-terminal a-amine thus avoiding potential problems with non-specific conjugation. An acetal derivative of PEG-propionaldehyde, i.e., PEG-acetaldehyde provides an additional benefit in so far as it provides for longer storage than PEG-propionaldehyde (U.S. Pat. No. 5,990,237).

Active esters of PEG carboxylic acids are probably one of the most used acylating agents for protein conjugation. Active esters react with primary amines near physiological conditions to form stable amides. Activation of PEG-carboxylic acids to succinimidyl active esters is accomplished by reacting the PEG-carboxylic acid with N-hydroxysuccinimide (NHS or HOSu) and a carbodiimide. Exemplary carboxylic acid derivatives of PEG include carboxymethylated PEG (CM-PEG), butanoic acid derivatives and propionic acid derivatives (U.S. Pat. No. 5,672,662). Changing the distance between the active ester and the PEG backbone by the addition of methylene units can dramatically influence reactivity towards water and amines (e.g., by reducing hydrolysis). Alternatively or in addition, hydrolysis can be reduced by introducing an α-branching moiety to the carboxylic acid.

PEGylation of free cysteine residues in a protein is useful for site-specific conjugation (e.g., using a protein modified to include cysteine residues as described herein). Exemplary PEG derivatives for cysteine conjugation include PEG-maleimide, PEG-vinylsulfone, PEG-iodoacetamide and PEG-orthopyridyl disulfide. Exemplary methods for conjugating PEG to cysteine residues and for conjugation using PEG-vinylsulfone are well known in the art.

U.S. Pat. No. 5,985,263 describes methods for conjugating PEG to the secondary amine group of histidine, which has a lower pKa than the primary amine. An advantage of this approach is that the acyl-histidine bond is not stable meaning that the peptide or protein is slowly released (i.e., the conjugate behaves as a slow release formulation or a pro-drug).

Another approach for PEGylation is to take advantage of an N-terminal serine or threonine, which can be converted to periodate as discussed above. Using this approach, PEG has been conjugated to bioactive proteins (e.g., Gaertner and Offord, 1996). PEG can also be conjugated to carbohydrate groups.

The choice of the suitable functional group for the PEG derivative is based on the type of available reactive group on the molecule that will be coupled to the PEG. For peptides or proteins, typical reactive amino acids include lysine, cysteine, histidine, arginine, aspartic acid, glutamic acid, serine, threonine, tyrosine. The N-terminal amino group and the C-terminal carboxylic acid can also be used as a site specific site by conjugation with aldehyde functional polymers.

In certain embodiments, the PEG derivatives are produced by reacting the PEG polymer with a group that is reactive with hydroxyl groups, typically anhydrides, acid chlorides, chloroformates and carbonates. In other embodiments, more efficient functional groups such as aldehyde, esters, amides, etc. are made available for protein conjugation.

In certain embodiments, heterobifunctional PEGs are used for conjugation. These heterobifunctional PEGs are useful for linking two entities, where a hydrophilic, flexible and biocompatible spacer is needed. Preferred end groups for heterobifunctional PEGs are maleimide, vinyl sulfones, pyridyl disulfide, amine, carboxylic acids and NHS esters. In other embodiments, the pegylation agents contain branched, Y shaped or comb shaped polymers that show reduced viscosity and lack of organ accumulation.

Conjugation of PEGs may include the use of spacer moieties that are cleavable or non-cleavable. In some embodiments, the cleavable spacer moiety is a redox-cleavable spacer moiety, such that the spacer moiety is cleavable in environments with a lower redox potential, such as the cytoplasm and other regions with higher concentrations of molecules with free sulfhydryl groups. Examples of spacer moieties that may be cleaved due to a change in redox potential include those containing disulfides. The cleaving stimulus can be provided upon intracellular uptake of the conjugated protein where the lower redox potential of the cytoplasm facilitates cleavage of the spacer moiety. In the case of PEG, the molecule can be activated to facilitate its binding to amines or imidazoles, a carboxylic group, a hydroxyl group or a sulfhydryl group.

In certain embodiments, placement of a suitable endopeptidase cleavage recognition sequence can serve to liberate an attached PEG moiety and/or liposomal moiety linked to the peptide, or liberate one or more peptide domains from one another so that one or more these peptide domains can function independently of one another in e.g., their targeted site. Incorporation of an endopeptidase cleavage recognition sequences can facilitate site specific cleavage by a suitable endopeptidase present in a eukaryotic or mammalian cell, such as asparagine endopeptidase, Factor Xa, furin, thrombin, cathepsin B, plasmin, and various matrix metalloproteinases (MMPs), such as MMP2, MMP7, MMP9, or MMP14.

Asparagine endopeptidase, also known as legumain, is a lysosomal cysteine protease that cleaves protein substrates on the C-terminal side of asparagine, such as Asn-Asp or Asn-Xaa-Asn (NXN). Exemplary peptides conjugated to PEG via an NXN sequence include NXNVGFPVAAVGFPV (SEQ ID NO: 32) and NXNVGFPVAAVGFPVHPL-SKHPYWSQP (SEQ ID NO: 33).

Sequences cleavable by MMP2, MMP7, MMP9, or MMP14 include PLGLAG (SEQ ID NO: 34), PLG-C(me)-AG (SEQ ID NO: 35), RPLALWRS (SEQ ID NO: 36), ESPAYYTA (SEQ ID NO: 37), DPRSFL (SEQ ID NO: 38), PPRSFL (SEQ ID NO: 39), RLQLKL (SEQ ID NO: 40), and RLQLK(Ac) (SEQ ID NO: 41). Cathepsin B is a tumor associated protease that can act upon the dipeptide sequences valine-citrulline and Phe-Lys. Furin cleaves the recognition sequence R-X-X-R (SEQ ID NO: 42), more preferably R-X-(K/R)-R (SEQ ID NO: 43). Factor Xa cleaves after the arginine residue in its preferred cleavage site I-(E/D)-G-R (SEQ ID NO: 44) and will sometimes cleave at other basic residues, depending on the conformation of the protein substrate. The most common secondary site, among those that have been sequenced, is Gly-Arg. Thrombin preferentially cleaves between Arg and Gly residues in e.g., the sequence LVPRGS (SEQ ID NO: 45).

Chemical Conjugation to Hydrophobic Moieties (Lipopeptides)

In certain preferred embodiments, the VI-SMR peptide is a monomeric, dimeric or multimeric lipopeptide containing one or more hydrophobic moieties chemically conjugated thereto. The hydrophobic moieties may be conjugated to N-terminus or C-terminus of the VI-SMR peptide through any free functional group on the N-terminal or C-terminal amino acids, for example, to the 6-amino group of lysine. Conjugation of the hydrophobic moiety can enhance anti-fusogenic activity of the VI-SMR peptide so that the activity is significantly higher after conjugation than prior to conjugation. In some embodiments, conjugation of a hydrophobic moiety to the VI-SMR peptide can enhance the anti-fusogenic activity by at least 2 fold, at least 10-fold, or at least 20 fold. In addition, conjugation of hydrophobic moieties can provide greater stability and improved half-life in vivo.

The hydrophobic moiety can be a fatty acid, sterol or fat soluble vitamin, such as vitamin A, vitamin D, vitamin E or vitamin K. The fatty acid can be a saturated, unsaturated, monounsaturated, or polyunsaturated fatty acid. In some embodiments, the fatty acid for conjugation is a beta-hydroxy fatty acid or a beta-amino fatty acid. In other embodiments, the fatty acids is selected from the group consisting of decanoic acid, undecanoic acid, dodecanoic acid, myristic acid, palmitic acid, stearic acid, arachidic acid, lignoceric acid, palmitoleic acid, oleic acid, linoleic acid, linolenic acid, arachidonic acid, trans-hexadecanoic acid, elaidic acid, lactobacillic acid, tuberculostearic acid, and cerebronic acid.

In some embodiments, the hydrophobic moiety is a sterol, such as a steroid with a hydroxyl group at the 3-position of the A-ring. Non-limiting examples of sterols for conjugation include, but are not limited to, zoosterols, such as cholesterol or derivatives thereof; and phytosterols, such as stigmasterol, beta-sitosterol, campesterol, ergosterol (provitamin D2), brassicasterol, delta-7-stigmasterol and delta-7-avenasterol.

In some embodiments, the hydrophobic moiety is an aliphatic group comprising between 6-22 carbons and a reactive group through which the aliphatic group is linked to the peptide. Non limiting examples of the reactive groups include, but are not limited to a carboxyl group, a carbonyl group, an amine group, a thiol group, a maleimide, an imido ester, an N-hydroxysuccinimide, alkyl halide, and aryl azide.

In some embodiments, the VI-SMR peptide is a monomeric lipopeptide. In other embodiments, the VI-SMR peptide is a dimeric or multimeric lipopeptide. In certain preferred embodiments, the VI-SMR peptide is a dimeric lipopeptide or a pegylated monomeric or dimeric lipopeptide.

In some embodiments, the VI-SMR peptide has a modular structure including a plurality of functional domains in a particular configuration (from amino to carboxyl ends), where A is a PEG, such as a 10 kD PEG; B is a peptide cleavage linker sequence for an endopeptidase; C is an SMR-containing peptide sequence, D is a cell penetrating peptide (CPP) sequence; E is a Clusterin binding peptide (Clu-BP); F is a mitochondrial targeting peptide (MTP); G is an anti-fusogenic peptide inhibitor domain; H is a viral attachment inhibitor (VAI) domain; and I is a hydrophobic moiety, such as a fatty acid. Additionally, in the described configurations below, parentheses define an optional domain and forward backslashes defines alternative domains in a particular position. Any combination of the foregoing functional domains in any configuration may be employed in the compositions and methods of the present application.

In a particulate embodiment, the VI-SMR peptide has the configuration (I)-A-(B)-D-E/F/G/H or a dimer thereof.

In another embodiment, the VI-SMR peptide has the configuration (I)-A-(B)-D-E/F/G/H or a dimer thereof.

In another embodiment, the VI-SMR peptide has the configuration (I)-A-(B)-C-E-G/H-(F) or a dimer thereof.

In another embodiment, the VI-SMR peptide has the configuration (I)-A-(B)-D-E-G/H-(F) or a dimer thereof.

In another embodiment, the VI-SMR peptide has the configuration C-D-E/F/G/H-(B)-A-(I) or a dimer thereof.

In another embodiment, the VI-SMR peptide has the configuration C-D-E/F/G/H-(B)-A-(I) or a dimer thereof.

In another embodiment, the VI-SMR peptide has the configuration C-D-E-G/H-(F)-(B)-A-(I) or a dimer thereof.

In another embodiment, the VI-SMR peptide has the configuration D-C-E-G/H-(F)-(B)-A-(I) or a dimer thereof.

Any of the foregoing configurations or other embodiments of the present application may further include a spacer peptide as described herein between one or more functional domains, such as Ala-Ala.

Other Chemical Modifications

The VI-SMR peptide of the present application may be chemically modified at the N-terminal, internal and/or C-terminal ends. Such modifications can be used e.g., to increase peptide stability, in vivo half-life, solubility and facilitate attachment of proteinaceous or non-proteinaceous moieties. Exemplary N-terminal modification include acetylation, biotinylation, dansyl labelling, fluorescein-labelling, 7-methoxycoumarin acetic acid (Mca)-labelling, palmitic acid conjugation, methylation (i.e., —$NHCH_3$ or —$NH(CH_3)_2$), adding a 1-amino-cyclohexane-carboxylic acid moiety (Chex); and adding a carbobenzoyl group, or blocking the amino terminus with any blocking group containing a carboxylate functionality defined by RCOO—, where R is selected from the group consisting of naphthyl, acridinyl, steroidyl, and similar groups. An exemplary C-terminal modification is amidation. Where the C-terminus is amidated, the carboxylic acid of the amino acid is converted to an amide, i.e., $NH_2$—$CH_2$—C(O)—$NH_2$.

Additional modifications include carboxylation, glycosylation, methylation (e.g., substitution of a-hydrogens with methyl groups), carbonylation, phosphorylation, dimerization, addition of interchain and/or intrachain disulfide bonds, addition of trans olefin, derivatization by known protecting/blocking groups, circularization, and substitution with D amino acids.

The VI-SMR peptide of the present application may further contain one or more covalently attached functional groups, preferably attached to either or both of the N and C termini. These covalently attached groups can include stabilizers, couplers, ligands, enzymatic substrates and/or combinations thereof. Preferred groups include acyl groups on the N terminus and cysteamine (cya) coupling groups on the C terminal end. To the latter may be conveniently attached other chemical moieties, e.g., dyes, ligands, small molecule drugs, proteins, enzymes, enzymatic substrates, etc. Alternatives to cya are also known to those of skill in the art. For stabilizing and/or blocking, e.g., cya may be replaced with an alky group such as methyl or ethyl, which are known to be conveniently positioned onto a —COOH group.

In some embodiments, a derivitizing group, including, but not limited to, a sulfhydryl-containing group or moiety may be positioned at the C-terminus of the VI-SMR peptide, even when it is not coupled to another chemical moiety. In one embodiment, the C-terminal end may be modified with a cysteamide group (—NH—$CH_2$—$CH_2$—SH), which can allow further coupling to drugs. A cysteamide group is compatible with the peptide synthesis using the Fmoc strategy and leads to a C-terminal protected peptide. Alternatively, the peptide can include a C-terminal cysteine residue containing a sulfhydryl (—SH) group that can be optionally utilized for conjugation to other moieties. In another embodiment, the C-terminal end includes a 2,4-diaminobutyric acid (DAB) moiety. C-terminal modifications may further include replacing the free acid with a carboxamide group or forming a cyclic lactam at the carboxy terminus to introduce structural constraints.

Naturally occurring side chains of the 20 genetically encoded amino acids (or D amino acids) may be replaced with other side chains with similar properties, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclic.

Such substitutions can include but are not necessarily limited to: (1) non-standard positively charged amino acids, like: ornithine; N-(4-aminobutyl)-glycine having a lysine side chain attached to the "N-terminus" and aminopropyl or aminoethyl groups attached to the amino group of glycine; (2) Non-naturally occurring amino acids with no net charge and sidechains similar to arginine, such as citrulline, with or without methylene groups; (3) non-standard non-naturally occurring amino acids with OH (e.g., serine), such as, homoserine, hydroxyproline, hydroxyvaline, and penicillamin; (4) proline derivatives, such as, D-Pro, including 3,4-dehydroproline, pyroglutamine, proline with fluorine substitutions on the ring, 1,3-thiazolidine-4-carboxylic acid; (5) Histidine derivative, such as beta-(2-thienyl)-alanine; or (6) alkyl derivatives, such as 2-aminobutyric acid, norvaline, norleucine, homoleucine, and alpha-aminoisobutyric acid.

In other embodiments, the C-terminal carboxyl group or a C-terminal ester may be induced to cyclize by internal displacement of the —OH or the ester (—OR) of the carboxyl group or ester respectively with the N-terminal amino group to form a cyclic peptide. For example, after synthesis and cleavage to give the peptide acid, the free acid is converted to an activated ester by an appropriate carboxyl group activator such as dicyclohexylcarbodiimide (DCC) in solution, for example, in methylene chloride ($CH_2Cl$), dimethyl formamide (DMF) mixtures. The cyclic peptide is then formed by internal displacement of the activated ester with the N-terminal amine. Internal cyclization as opposed to polymerization can be enhanced by use of very dilute solutions. Such methods are well known in the art.

In other embodiments, the VI-SMR peptide of the present disclosure is cyclized or includes a desamino or descarboxy residue at the peptide termini so that there are no terminal amino or carboxyl groups. This can decrease susceptibility to proteases and/or to restrict the conformation of the peptide. C-terminal functional groups of the compounds of the present disclosure include amide, amide lower alkyl, amide di(lower alkyl), lower alkoxy, hydroxy, and carboxy, and the lower ester derivatives thereof, and the pharmaceutically acceptable salts thereof. The VI-SMR peptide may be cyclized by adding an N and/or C terminal cysteine and cyclizing the peptide through disulfide linkages or other side chain interactions.

3. VI-SMR-Encoded Polynucleotides

Another aspect of the present disclosure relates to a polynucleotide encoding any of the VI-SMR peptides described herein. In one embodiment, the polynucleotide is an expression vector. As used herein, the term "expression vector" refers to a non-viral or a viral vector that comprises a polynucleotide encoding the VI-SMR peptide of the present disclosure in which the peptide coding sequences are operably linked to regulatory sequences sufficient for expressing the peptide in a cell.

The regulatory sequences may be selected on the basis of the host cells to be used for expression, such that the design of the expression vector and inclusion of regulatory sequences depends on such factors as the choice of the host cell to be transformed, the level of expression of protein desired, whether the peptide is to be secreted into the extracellular milieu and the like. The expression vectors of the disclosure can be introduced into host cells to direct the expression of the VI-SMR peptide of the present disclosure in vitro for production purposes or in vivo for therapeutic purposes.

As used herein, the terms “control sequences” or “regulatory sequences” refer to DNA sequences refer to promoter sequences, polyadenylation signals, transcription termination sequences, upstream regulatory domains, origins of replication, internal ribosome entry sites (“IRES”), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell. Control/regulatory sequences include those which direct constitutive expression of a nucleotide sequence in many types of host cells and those which direct expression of the nucleotide sequence only in certain host cells (e.g., tissue-specific regulatory sequences).

A nucleic acid sequence is “operably linked” to another nucleic acid sequence when the former is placed into a functional relationship with the latter. In preferred embodiments, the expression vector encodes an exogenous presequence or signal peptide that is operably linked to the peptide coding sequences for expression as a preprotein that participates in the secretion of the polypeptide. Further, a promoter or enhancer is said to be operably linked to a coding sequence if it affects the transcription of the sequence and a ribosome binding site is operably linked to a coding sequence if it is positioned so as to facilitate translation. An expression vector may further include an intron or chimeric intron.

In certain cases, these vectors may be engineered to target certain diseases or cell populations by using the targeting characteristics inherent to the virus vector or engineered into the virus vector. Specific cells may be “targeted” for delivery of polynucleotides, as well as expression. Thus, the term “targeting”, in this case, may be based on the use of endogenous or heterologous binding agents in the form of capsids, envelope proteins, antibodies for delivery to specific cells, the use of tissue-specific regulatory elements for restricting expression to specific subset(s) of cells, or both.

In certain embodiments, the expression vector is engineered to direct expression of the peptide ubiquitously or preferentially in a particular cell type (e.g., tissue-specific regulatory elements are used to express the polynucleotide). Thus, in certain embodiments, expression of the peptide is under the control of a tissue specific or ubiquitous promoter, such as the CMV promoter or a CMV-chicken beta-actin hybrid (CAG) promoter. As used herein, the term “promoter” is to be taken in its broadest context and includes transcriptional regulatory elements (TREs) from genomic genes or chimeric TREs therefrom, including the TAT A box or initiator element for accurate transcription initiation, with or without additional TREs (i.e., upstream activating sequences, transcription factor binding sites, enhancers and silencers) which regulate activation or repression of genes operably linked thereto in response to developmental and/or external stimuli and trans-acting regulatory proteins or nucleic acids. The promoter may be constitutively active or it may be active in one or more tissues or cell types in a developmentally regulated manner. A promoter may contain a genomic fragment or it may contain a chimera of one or more TREs combined together.

In some embodiments, a tissue specific or virus-specific promoter may be used. Exemplary tissue-specific regulatory elements are known in the art and may include liver-specific promoter (e.g., albumin promoter), lymphoid-specific promoters, epithelial cell-specific promoters, promoters of T cell receptors and immunoglobulins, neuron-specific promoters (e.g., the neurofilament promoter), pancreas-specific promoters (e.g., insulin promoter), and mammary gland-specific promoters (e.g., milk whey promoter). Developmentally-regulated promoters (e.g., the a-fetoprotein promoter) are also encompassed.

In some embodiments, the expression vector is a viral vector, typically used for in vivo gene delivery. Exemplary viral vectors may include or be derived from an adeno-associated virus (AAV), adenovirus, herpesvirus, vaccinia virus, poliovirus, poxvirus, HIV virus, lentivirus, retrovirus, Sindbis and other RNA viruses and the like. Also preferred are any viral families which share the properties of these viruses which make them suitable for use as vectors. Retroviruses include Murine Moloney Leukemia virus (MMLV), HIV and other lentivirus vectors. Adenovirus vectors are relatively stable and easy to work with, have high titers and can be delivered in aerosol formulation and can transfect non-dividing cells. Poxviral vectors are large and have several sites for inserting genes, they are thermostable and can be stored at room temperature. Viral delivery systems typically utilize viral vectors having one or more genes removed and with and an exogenous gene and/or gene/promoter cassette being inserted into the viral genome in place of the removed viral DNA. The necessary functions of the removed gene(s) may be supplied by cell lines which have been engineered to express the gene products of the early genes in trans.

A viral vector may be derived from an adeno-associated virus (AAV), adenovirus, herpesvirus, vaccinia virus, poliovirus, poxvirus, a retrovirus (including a lentivirus, such as HIV-1 and HIV-2), Sindbis and other RNA viruses, alphavirus, astrovirus, coronavirus, orthomyxovirus, papovavirus, paramyxovirus, parvovirus, picornavirus, togaviruses and the like. A non-viral vector is simply a “naked” expression vector that is not packaged with virally derived components (e.g., capsids and/or envelopes).

Non-viral expression vectors can be utilized for non-viral gene transfer, either by direct injection of naked DNA or by encapsulating the VI-SMR peptide-encoding polynucleotides in liposomes, nanoparticles, hydrogels, microcapsules, or virus-like particles. Such compositions can be further linked by chemical conjugation to targeting domains to facilitate targeted delivery and/or entry of nucleic acids into desired cells of interest. In addition, plasmid vectors may be incubated with synthetic gene transfer molecules such as polymeric DNA-binding cations like polylysine, protamine, and albumin, and linked to cell targeting ligands such as asialoorosomucoid, insulin, galactose, lactose or transferrin.

Alternatively, naked DNA may be employed. Uptake efficiency of naked DNA may be improved by compaction or by using biodegradable latex beads. Such delivery may be improved further by treating the beads to increase hydrophobicity and thereby facilitate disruption of the endosome and release of the DNA into the cytoplasm.

4. VI-SMR-Loaded Exosomes

In another aspect, the present application provides an exosome loaded with a VI-SMR peptide described herein. Exosomes are recognized and endocytosed by tissue cells via specific interactions between surface-membrane proteins. Engineering exosomes loaded with the VI-SMR peptides of the present application and/or other therapeutic agents described herein (as molecular cargo) for delivery can provide increased circulation half-life, enhanced uptake by target cells and protection of the molecular cargo therein from immunological attack. Methods for loading exosomes are described in U.S. Patent Appl. Nos. 2014/0356382, 2020/0306297, and 2020/0347112. In other embodiments, exosomes for delivery are loaded with expression vectors encoding a VI-SMR peptide of the present application.

5. Production of VI-SMR Peptides

The VI-SMR peptides of the present disclosure can be chemically synthesized or produced from cells transformed with polynucleotide expression vectors encoding the VI-SMR peptide. VI-SMR peptides of the present disclosure may be synthesized using traditional liquid or solid-phase synthesis. Fmoc and t-Boc solid phase peptide synthesis (SPPS) can be employed to grow the peptides from carboxy to amino-terminus.

In other embodiments the VI-SMR peptides are synthesized using recombinant DNA technologies well known to those skilled in the art. Polynucleotide expression vectors can be designed to facilitate preparative expression levels in many different cell hosts, including bacteria, yeast, insect cells, and mammalian cells.

In another aspect, a method of producing a VI-SMR peptide according to the present disclosure comprises culturing a host cell transformed with a VI-SMR peptide-encoding polynucleotide or expression vector under conditions that allows production of the VI-SMR peptide, and purifying the VI-SMR peptide from the cell. The peptides may be produced by culturing a cell transiently or stably expressing a VI-SMR peptide; and purifying the peptide from the cultured cells. Any cell capable of producing a functional peptide may be used. The peptide-expressing cell may be of prokaryotic or bacterial origin, such as *E. coli* or it may be of eukaryotic or mammalian origin, such as a human cell. In other embodiments, the cell is a yeast cell or an insect cell. Where the cell is of eukaryotic origin, the peptide-producing cell is preferably stably transformed with a polynucleotide so as to express the peptide.

Recombinant antiviral VI-SMR peptide-encoding nucleic acids may be introduced (e.g., transduced, transformed or transfected) into host cells, for example, via a vector, such as an expression vector. The vector is typically a plasmid, but such vectors can also be, for example, a viral particle, a phage, etc. Host cells for expressing the VI-SMR peptide include prokaryotic (i.e., bacterial) host cells, such as *E. coli, Streptomyces* and *Salmonella typhimurium*; fungal cells, such as *Saccharomyces cerevisiae, Pichia pastoris* and *Neurospora crassa*; insect cells such as *Drosophila* and *Spodoptera frugiperda*; mammalian cells such as 3T3, COS, CHO, BHK, HEK 293 or Bowes melanoma; plant cells, including algae cells, etc.

For stable, high-yield production of recombinant antiviral VI-SMR peptide, stable expression systems may be employed. For example, polynucleotides encoding a VI-SMR peptide can be introduced into suitable host cells using expression vectors which contain a selectable marker gene. Following the introduction of the vector, cells are allowed to grow for 1-2 days in an enriched media before they are switched to selective media. The selectable marker confers resistance to selection and its presence allows growth and recovery of cells which successfully express the introduced sequences. For example, resistant groups or colonies of stably transformed cells can proliferate using tissue culture techniques appropriate to the cell type. Host cells transformed with a nucleic acid encoding the VI-SMR peptide are cultured under conditions suitable for the expression, secretion and recovery of the encoded protein from cell culture.

6. Inhibitory Activity of the VI-SMR Peptide

VI-SMR peptides may be tested for binding and/or functional activities via binding assays, infectivity assays and the like. The VI-SMR peptide-containing composition may be evaluated for coronavirus binding activity using a variety of SARS-CoV-2 S protein-, SARS-CoV-2 S1 subunit (receptor binding domain, RBD) protein-, and/or ACE2 protein reagents, which may be His-tagged, Fc-tagged, Avi-tagged, or biotin-labeled in order to facilitate detection of binding on microtiter plates and the like using suitable colorimetric, chemiluminescent substrates (BPS Bioscience, San Diego, Calif.).

VI-SMR peptides will be tested for anti-SARS-CoV-2 activity using a functional assay evaluating the ability of the VI-SMR peptides to inhibit CoV-2 replication. The functional assays described below further allow for the generation of a dose-response curve reflecting the degree of CoV-2 inhibition, including an IC50 determination for a given VI-SMR peptide.

In one embodiment, a VI-SMR peptide is tested for inhibitory activity by an in vitro plaque reduction assay using SARS-CoV-2 infected Vero E6 cells, a monkey kidney cell line, which is known to express the ACE2 receptor. Briefly, Vero E6 cells are plated onto 12-well tissue culture plates and incubated overnight to allow for adherence to the plates. Serial dilutions of VI-SMR peptide in cell maintenance media are then incubated with a defined amount of SARS-CoV-2 for one hour in the absence of Vero E6 cells. Negative control solutions include SARS-CoV-2 incubated for 1 hr in cell maintenance media without VI-SMR peptide or cells. Following the one hour incubation, the cell maintenance media is removed from the Vero E6 seeded plates and replaced with the pre-incubated solutions of VI-SMR peptide/SARS-CoV-2/cell media (test) or SARS-CoV-2/cell media (negative control). The cells are then incubated for 1 hr to allow adsorption of virus to the cells. Following the 1 hr incubation, the suspension is removed and methylcellulose overlays containing matched concentrations of VI-SMR peptide are added to each well. The plates are incubated for 3 days, inactivated and then stained with crystal violet stain. Dose response curves are then generated based on the degree of replication inhibition in each well compared to the corresponding negative controls (i.e., absence of VI-SMR peptide).

In another embodiment, a VI-SMR peptide is tested for inhibitory activity using lentivirus-based, VSV-based or MuLV-based virus particles pseudotyped with a CoV Spike (S) protein, such as SARS-CoV-2 S protein, and operably linked to a luciferase reporter. More particularly, the assay evaluates the ability of VI-SMR peptide to block expression of the luciferase reporter in ACE2-expressing cells infected with the S/S1-pseudotyped lentivirus reporter. A "bald" or non-pseudotyped control containing the luciferase reporter alone can be used as a negative control.

The ACE2-expressing cells or cell lines are infected with the pseudotyped or non-pseudotyped virus particles in the presence of increasing concentrations of VI-SMR peptide. When using cells exhibiting low or no ACE2 expression, the pseudotyped and/or non-pseudotyped virus particles are co-infected with an expression construct, such as replication-defective HIV-1 particles engineered to express human ACE2. A lentivirus-based luciferase reporter system for carrying out this assay includes pseudotyped (CoV-2 S protein) lentivirus reporters, non-pseudotyped lentivirus reporters (negative control), and ACE2-expressing lentiviruses (BPS Bioscience, San Diego, Calif., BPS #s 79942, 79943 and 79944). Additional reagents and cell lines for carrying out the above experiments may be obtained from BPS Bioscience (San Diego, Calif.) and Creative Biogene (Shirley, N.Y.).

7. Combination Therapies

In some embodiments, the above-described methods of the present application further comprise administration of one or more antiviral agents. These agents may be administered before, at the same time or after administration of the V-SMR peptide. In one embodiment, the additional active agent is an antiviral agent. Exemplary antiviral agents for use in the present application include, but are not limited to, viral polymerase inhibitors, such as Remdesivir, GS-441524, Faviravir, EIDD-2801, EIDD-2901, EIDD-1931, Ribavirin, 6-azauridine; convalescent plasma; neutralizing mAbs or mAbs inhibiting coronavirus attachment or entry, such as REGN10933, REGN10987, LY3819253, AZD7442, BRII-196, CT-P59, JS016, SCTA01, STI-1499, TY027, 47D11; anti-IL6 monoclonal antibodies, such as Tocilizumab; protease inhibitors targeting $MP^{pro}$, such as Lopinavir, Ritonavir, Dipyridamole, and Danoprevir; Ivermectin; Saracatinib; protease inhibitors targeting TMPRSS2, such as Camostat, Nafomastat, and Nafomastat mesylate; S-protein targeted drugs, such as Arbidol (umifenovir) and Hydroxychloroquine; cytokines, such as interferons-α, -β, -λ, Dexamethasone, Anakinra, Hydrocortisone, Azithromycin, Ulinastatin and Ciclesonide; Janus kinase inhibitors, such as Ruxolitinib and Baricitinib; AXL kinases inhibitors, such as Bemcentinib; Dihydroorotate dehydrogenase (DHODH) inhibitors, such as PTC299; recombinant ACE2; HR2P-EK1C4, IPB03 and other lipopeptide fusion inhibitors described herein above; Fluvoxamine; Apilomod; Ciclesonide; Tetrahydroquinoline oxocarbazate; GC373; Vitamin D; $Zn^{2+}$; and combinations thereof.

In some embodiments, the additional active agent is a heat shock protein family inhibitor. In a particular embodiment, the heat shock inhibitor is a mortalin inhibitor. The mortalin inhibitor may be administered with or without the VI-SMR peptide. Exemplary mortalin (Hsp70) inhibitors include, but are not limited to, MKT-077 (1-Ethyl-2-[[3-ethyl-5-(3-methyl-2(3H)-benzothiazolylidene)-4-oxo-2-thiazolidinylidene]methyl]-pyridinium chloride); Omeprazole (5-Methoxy-2-[[(4-methoxy-3,5-dimethyl-2-pyridinyl) methyl]sulfinyl]-1H-benzimidazole); DMA (5-(N,N-Dimethyl)amiloride); PES (2-phenylethynesulfonamide); Mortaparib (5-[1-(4-methoxyphenyl)(1,2,3,4-tetraazol-5-yl)]-4-phenylpyrimidine-2-ylamine); JG-98 (3-benzyl-2-((Z)-((E)-5-(6-chloro-3-methylbenzo[d]thiazol-2(3H)-ylidene)-3-ethyl-4-oxothiazolidin-2-ylidene)methyl)thiazol-3-ium chloride); Embelin (2,5-dihydroxy-3-undecyl-2, 5-cyclohexadiene-1, 4-benzoquinone), and AR-12. Additional mortalin inhibitors are described in U.S. Pat. No. 9,642,843 and U.S. Patent Publication Nos. 2012/0252818, 2017/0014434, and 2018/0002325.

8. Viral Infections for Treatment

The compositions and methods of the present application may be applied to any coronavirus in the Orthocoronavirinae family, including but not limited to those described herein. The genetically diverse Orthocoronavirinae family is divided into four genera (alpha, beta, gamma, and delta coronaviruses). Human CoVs are limited to the alpha and beta subgroups. Exemplary human CoVs include severe acute respiratory syndrome coronavirus-2 (SARS-CoV-2), severe acute respiratory syndrome coronavirus (SARS-CoV), Middle East respiratory syndrome coronavirus (MERS-CoV), HCoV-229E, HCoV-OC43, HCoV-NL63, and HCoV-HKU1.

Before the advent of human SARS CoV-2 or COVID-19, human coronaviruses were believed to cause 10% of all upper and lower respiratory tract infections, which typically present with common-cold like symptoms, but were known to cause more severe disease in young children, as well as people with underlying respiratory conditions (i.e. asthma, COPD) and the elderly.

Zoonotic CoVs have a natural predilection for emergence into new host species giving rise to new diseases most recently exemplified in humans by severe acute respiratory syndrome coronavirus 2 (SARS-CoV-2), severe acute respiratory syndrome coronavirus (SARS-CoV), and Middle East respiratory syndrome coronavirus (MERS-CoV) (de Wit et al., 2016). Interestingly, all known human CoVs are thought to have emerged as zoonoses from wild or domestic animals.

Nonlimiting examples of subgroup 1a alphacoronaviruses and their GenBank Accession Nos. include FCov.FIPV.79.1146.VR.2202 (NV 007025), transmissible gastroenteritis virus (TGEV) (NC_002306; Q811789.2; DQ811786.2; DQ811788.1; DQ811785.1; X52157.1; AJ011482.1; KC962433.1; AJ271965.2; JQ693060.1; KC609371.1; JQ693060.1; JQ693059.1; JQ693058.1; JQ693057.1; JQ693052.1; JQ693051.1; JQ693050.1); porcine reproductive and respiratory syndrome virus (PRRSV) (NC 001961.1; DQ811787), as well as any subtype, clade or sub-clade thereof, including any other subgroup 1a coronavirus now known (e.g., as can be found in the GenBank® Database) or later identified in the GenBank® Database.

Nonlimiting examples of a subgroup 1b alphacoronaviruses and their GenBank Accession Nos. include HCoV.NL63.Amsterdam.I (NC_005831), BtCoV.HKU2.HK.298.2006 (EF203066), BtCoV.HKU2.HK.33.2006 (EF203067), BtCoV.HKU2.HK.46.2006 (EF203065), BtCoV.HKU2.GD.430.2006 (EF203064), BtCoV.1A.AFCD62 (NC_010437), BtCoV.1B.AFCD307 (NC_010436), BtCov.HKU8.AFCD77 (NC_010438), BtCoV.512.2005 (DQ648858); porcine epidemic diarrhea viruses (NC_003436, DQ355224.1, DQ355223.1, DQ355221.1, JN601062.1, JN601061.1, JN601060.1, JN601059.1, JN601058.1, JN601057.1, JN601056.1, JN601055.1, JN601054.1, JN601053.1, JN601052.1, JN400902.1, JN547395.1, FJ687473.1, FJ687472.1, FJ687471.1, FJ687470.1, FJ687469.1, FJ687468.1, FJ687467.1, FJ687466.1, FJ687465.1, FJ687464.1, FJ687463.1, FJ687462.1, FJ687461.1, FJ687460.1, FJ687459.1, FJ687458.1, FJ687457.1, FJ687456.1, FJ687455.1, FJ687454.1, FJ687453 FJ687452.1, FJ687451.1, FJ687450.1, FJ687449.1, AF500215.1, KF476061.1, KF476060.1, KF476059.1, KF476058.1, KF476057.1, KF476056.1, KF476055.1, KF476054.1, KF476053.1, KF476052.1, KF476051.1, KF476050.1, KF476049.1, KF476048.1, KF177258.1, KF177257.1, KF177256.1, KF177255.1), HCoV.229E (NC_002645), as well as any subtype, clade or sub-clade thereof, including any other subgroup 1b coronavirus now known (e.g., as can be found in the GenBank® Database) or later identified in the GenBank® Database.

Nonlimiting examples of subgroup 2a betacoronaviruses and their GenBank Accession Nos. include HCoV.HKU1.C.N5 (DQ339101), MHV.A59 (NC_001846), PHEV.VW572 (NC_007732), HCoV.OC43.ATCC.VR.759 (NC_005147), bovine enteric coronavirus (BCoV.ENT) (NC_003045), as well as any subtype, clade or sub-clade thereof, including any other subgroup 2a coronavirus now known (e.g., as can be found in the GenBank® Database) or later identified in the GenBank® Database.

Nonlimiting examples of subgroup 2b betacoronaviruses and their GenBank Accession Nos. include human SARS CoV-2 isolates, such as Wuhan-Hu-1 (NC_045512.2) and any CoV-2 isolates comprising a genomic sequence set forth in GenBank Accession Nos., such as MT079851.1, MT470137.1, MT121215.1, MT438728.1, MT470115.1, MT358641.1, MT449678.1, MT438742.1, LC529905.1, MT438756.1, MT438751.1, MT460090.1, MT449643.1, MT385425.1, MT019529.1, MT449638.1, MT374105.1, MT449644.1, MT385421.1, MT365031.1, MT385424.1, MT334529.1, MT466071.1, MT461669.1, MT449639.1, MT415321.1, MT385430.1, MT135041.1, MT470179.1, MT470167.1, MT470143.1, MT365029.1, MT114413.1, MT192772.1, MT135043.1, MT049951.1; human SARS CoV-1 isolates, such as SARS CoV.A022 (AY686863), SARSCoV.CUHK-W1 (AY278554), SARSCoV.GDO1 (AY278489), SARSCoV.HC.SZ.61.03 (AY515512), SARS-CoV.SZ16 (AY304488), SARSCoV.Urbani (AY278741), SARSCoV.civet010 (AY572035), SARSCoV.MA.15 (DQ497008); bat SARS CoV isolates, such as BtSAR-S.HKU3.1 (DQ022305), BtSARS.HKU3.2 (DQ084199), BtSARS.HKU3.3 (DQ084200), BtSARS.Rm1 (DQ412043), BtCoV.279.2005 (DQ648857), BtSARS.Rfl (DQ412042), BtCoV.273.2005 (DQ648856), BtSARS.Rp3 (DQ071615), as well as any subtype, clade or sub-clade thereof, including any other subgroup 2b coronavirus now known (e.g., as can be found in the GenBank® Database) or later identified in the GenBank® Database.

Nonlimiting examples of subgroup 2c betacoronaviruses and their GenBank Accession Nos. include Middle East respiratory syndrome coronavirus (MERS) isolates, such as Riyadh_2_2012 (KF600652.1), Al-Hasa_18_2013 (KF600651.1), Al-Hasa_17_2013 (KF600647.1), Al-Hasa_15_2013 (KF600645.1), Al-Hasa_16_2013 (KF600644.1), Al-Hasa_21_2013 (KF600634), Al-Hasa_19_2013 (KF600632), Buraidah_1_2013 (KF600630.1), Hafr-Al-Batin_1_2013 (KF600628.1), Al-Hasa_12_2013 (KF600627.1), Bishaltoreq._1_2012 (KF600620.1), Riyadh_3_2013 (KF600613.1), Riyadh_1_2012 (KF600612.1), Al-Hasa_3_2013 (KF186565.1), Al-Hasa_1_2013 (KF186567.1), Al-Hasa2_2013 (KF186566.1), Al-Hasa_4_2013 (KF186564.1); Betacoronavirus England 1-N1 (NC_019843), SA-N1 (KC667074); human betacoronavirus 2c Jordan-N3/2012 (KC776174.1); human betacoronavirus 2c EMC/2012, (JX869059.2); any bat coronavirus subgroup 2c isolate, such as bat coronavirus Taper/CII_KSA_287/Bisha/Saudi Arabia (KF493885.1), bat coronavirus Rhhar/CII_KSA 003/Bisha/Saudi Arabia/2013 (KF493888.1), bat coronavirus Pikuh/CII_KSA_001/Riyadh/Saudi Arabia/2013 (KF493887.1), bat coronavirus Rhhar/CII_KSA 002/Bisha/Saudi Arabia/2013 (KF493886.1), bat coronavirus Rhhar/CII_KSA_004/Bisha/Saudi Arabia/2013 (KF493884.1), bat coronavirus BtCoV.HKU4.2 (EF065506), bat coronavirus BtCoV.HKU4.1 (NC_009019), bat coronavirus BtCoV.HKU4.3 (EF065507), bat coronavirus BtCoV.HKU4.4 (EF065508), bat coronavirus BtCoV133.2005 (NC_008315), bat coronavirus BtCoV.HKU5.5 (EF065512), bat coronavirus BtCoV.HKU5.1 (NC_009020), bat coronavirus BtCoV.HKU5.2 (EF065510), bat coronavirus BtCoV.HKU5.3 (EF065511), and bat coronavirus HKU5 isolate (KC522089.1); any additional subgroup 2c, such as KF192507.1, KF600656.1, KF600655.1, KF600654.1, KF600649.1, KF600648.1, KF600646.1, KF600643.1, KF600642.1, KF600640.1, KF600639.1, KF600638.1, KF600637.1, KF600636.1, KF600635.1, KF600631.1, KF600626.1, KF600625.1, KF600624.1, KF600623.1, KF600622.1, KF600621.1, KF600619.1, KF600618.1, KF600616.1, KF600615.1, KF600614.1, KF600641.1, KF600633.1, KF600629.1, KF600617.1, KC869678.2; KC522088.1, KC522087.1, KC522086.1, KC522085.1, KC522084.1, KC522083.1, KC522082.1, KC522081.1, KC522080.1, KC522079.1, KC522078.1, KC522077.1, KC522076.1, KC522075.1, KC522104.1, KC522104.1, KC522103.1, KC522102.1, KC522101.1, KC522100.1, KC522099.1, KC522098.1, KC522097.1, KC522096.1, KC522095.1, KC522094.1, KC522093.1, KC522092.1, KC522091.1, KC522090.1, KC522119.1, KC522118.1, KC522117.1, KC522116.1, KC522115.1, KC522114.1, KC522113.1, KC522112.1, KC522111.1, KC522110.1, KC522109.1, KC522108.1, KC522107.1, KC522106.1, KC522105.1); *Pipistrellus* bat coronavirus HKU4 isolates (KC522048.1, KC522047.1, KC522046, 1, KC522045.1, KC522044.1, KC522043.1, KC522042.1, KC522041.1, KC522040.1, KC522039.1, KC522038.1, KC522037.1, KC522036.1, KC522048.1, KC522047.1, KC522046.1, KC522045.1, KC522044.1, KC522043.1, KC522042.1, KC522041.1, KC522040.1, KC522039.1, KC522038.1, KC522037.1, KC522036.1, KC522061.1, KC522060.1, KC522059.1, KC522058.1, KC522057.1, KC522056.1, KC522055.1, KC522054.1, KC522053.1, KC522052.1, KC522051.1, KC522050.1, KC522049.1, KC522074.1, KC522073.1, KC522072.1, KC522071.1, KC522070.1, KC522069.1, KC522068.1, KC522067.1, KC522066.1, KC522065.1, KC522064.1, KC522063.1, KC522062.1), as well as any subtype, clade or sub-clade thereof, including any other subgroup 2c coronavirus now known (e.g., as can be found in the GenBank® Database) or later identified in the GenBank® Database.

Nonlimiting examples of subgroup 2d betacoronaviruses and their GenBank Accession Nos. include BtCoV.HKU9.2 (EF065514), BtCoV.HKU9.l (NC_009021), BtCoV.HkU9.3 (EF065515), BtCoV.HKU9.4 (EF065516), as well as any subtype, clade or sub-clade thereof, including any other subgroup 2d coronavirus now known (e.g., as can be found in the GenBank® Database) or later identified in the GenBank® Database.

Nonlimiting examples of subgroup 3 gammacoronaviruses include IBV.Beaudette.IBV.p65 (DQ001339) or any other subgroup 3 coronavirus now known (e.g., as can be found in the GenBank® Database) or later identified in the GenBank® Database.

A coronavirus defined by any of the isolates or genomic sequences in the aforementioned subgroups 1a, 1b, 2a, 2b, 2c, 2d and 3 can be targeted for prophylactic or therapeutic use in accordance with the methods and compositions of the present application.

The methods of the present application may be also be used to prevent or treat other viral infections that are inhibited by the VI-SMR peptide of the present application, including enveloped RNA and DNA viruses. In certain preferred embodiments, the virus includes a surface protein containing mannose residues.

Exemplary RNA viruses for prophylactic or therapeutic treatment include retroviruses (e.g., HIV-1, HIV-2, HTLV-I, HTLV-II); bunyaviruses (e.g., Rift Valley fever virus, Crimean-Congo hemorrhagic fever virus); filoviruses (e.g., Ebola virus, Marburg virus); flaviviruses (e.g., Hepatitis C virus, West Nile virus, Dengue fever virus, Zika virus, yellow fever virus, tick-borne encephalitis virus, Saint Louis encephalitis virus, GB virus C); enteroviruses (Types A to L, including coxsackieviruses (Types A to C), echoviruses, rhinoviruses (Types A to C), poliovirus); orthomyxoviruses (e.g., influenza Types A, -B, -C, -D, including A subtypes H1N1, H5N1, H3N2); paramyxoviruses (e.g., rubulavirus (mumps), rubeola virus (measles), respiratory syncytial virus, Newcastle disease, parainfluenza); parvoviruses (e.g., parvovirus B19 virus); rhabdoviruses (e.g., Rabies virus); arenaviruses (e.g., lymphocytic choriomeningitis virus and several Lassa fever viruses, including Guanarito virus, Junin virus, Lassa virus, Lujo virus, Machupo virus, Sabia virus, Whitewater Arroyo virus); alphaviruses (e.g., Venezuelan equine encephalitis virus, eastern equine encephalitis virus; western equine encephalitis virus); Hepatitis A virus; Hepatitis D virus; Hepatitis E virus; as well as any type, subtype, clade or sub-clade thereof.

Exemplary DNA viruses for prophylactic or therapeutic treatment include herpesviruses (e.g., HSV-1, HSV-2, EBV, VZV, HCMV-1, HHV-6, HHV-7, HHV-8), papillomaviruses (e.g., human papilloma virus (HPV) Types 1, 2, 4, 6, 11, 16, 18, 26, 30, 31, 33, 34, 35, 39, 40, 41, 42, 43, 44, 45, 51, 52, 54, 55, 56, 57, 58, 59, 61, 62, 64, 67, 68, 69, 70); poxviruses (e.g., smallpox virus), hepadnaviruses (Hepatitis B virus); anelloviruses (e.g., transfusion transmitted virus or torque teno virus (TTV); as well as any type, subtype, clade or sub-clade thereof.

Pharmaceutical Compositions for Administration

The VI-SMR peptide or expression vector encoding the same is generally administered in combination with a pharmaceutically acceptable carrier. As used herein, the term "pharmaceutically acceptable" refers to a molecular entity or composition that does not produce an adverse, allergic or other untoward reaction when administered to an animal or a human, as appropriate. The term "pharmaceutically acceptable carrier", as used herein, includes any and all solvents, solubilizers, fillers, stabilizers, surfactants, binders, absorbents, bases, buffering agents, excipients, lubricants, controlled release vehicles, diluents, emulsifying agents, humectants, lubricants, gels, dispersion media, coatings, antibacterial or antifungal agents, isotonic and absorption delaying agents, and the like, compatible with pharmaceutical administration. The use of such carriers and agents for pharmaceutically active substances is well-known in the art.

Exemplary carriers or excipients include but are not limited to, calcium carbonate, calcium phosphate, various sugars, starches, cellulose derivatives, gelatin, polymers such as polyethylene glycols, water, saline, isotonic aqueous solutions, phosphate buffered saline, dextrose, 0.3% aqueous glycine, glycerol, ethanol and the like, as well as combinations thereof. In many cases, it will be preferable to include isotonic agents, for example, sugars, polyalcohols such as mannitol, sorbitol, or sodium chloride in the composition, or glycoproteins for enhanced stability, such as albumin, lipoprotein and globulin. Pharmaceutically acceptable carriers may further comprise minor amounts of auxiliary substances such as wetting or emulsifying agents, preservatives or buffers, which enhance the shelf life or effectiveness of the therapeutic agents. In certain embodiments, the pharmaceutically acceptable carrier comprises serum albumin.

Formulation characteristics that can be modified include, for example, pH and osmolality. For example, it may be desired to achieve a formulation that has a pH and osmolality similar to that of human blood or tissues to facilitate the formulation's effectiveness when administered parenterally.

Buffers are useful in the present disclosure for, among other purposes, manipulation of the total pH of the pharmaceutical formulation (especially desired for parenteral administration). A variety of buffers known in the art can be used in the present formulations, such as various salts of organic or inorganic acids, bases, or amino acids, and including various forms of citrate, phosphate, tartrate, succinate, adipate, maleate, lactate, acetate, bicarbonate, or carbonate ions. Particularly advantageous buffers for use in parenterally administered forms of the presently disclosed compositions in the present disclosure include sodium or potassium buffers, including sodium phosphate, potassium phosphate, sodium succinate and sodium citrate.

Sodium chloride can be used to modify the tonicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%).

In one embodiment, sodium phosphate is employed in a concentration approximating 20 mM to achieve a pH of approximately 7.0. A particularly effective sodium phosphate buffering system comprises sodium phosphate monobasic monohydrate and sodium phosphate dibasic heptahydrate. When this combination of monobasic and dibasic sodium phosphate is used, advantageous concentrations of each are about 0.5 to about 1.5 mg/ml monobasic and about 2.0 to about 4.0 mg/ml dibasic, with preferred concentrations of about 0.9 mg/ml monobasic and about 3.4 mg/ml dibasic phosphate. The pH of the formulation changes according to the amount of buffer used.

Depending upon the dosage form and intended route of administration it may alternatively be advantageous to use buffers in different concentrations or to use other additives to adjust the pH of the composition to encompass other ranges. Useful pH ranges for compositions of the present disclosure include a pH of about 2.0 to a pH of about 12.0.

In some embodiments, it will also be advantageous to employ surfactants in the presently disclosed formulations, where those surfactants will not be disruptive of the drug-delivery system used. Surfactants or anti-adsorbants that prove useful include polyoxyethylenesorbitans, polyoxyethylenesorbitan monolaurate, polysorbate-20, such as Tween-20™, polysorbate-80, polysorbate-20, hydroxycellulose, genapol and BRIJ surfactants. By way of example, when any surfactant is employed in the present disclosure to produce a parenterally administrable composition, it is advantageous to use it in a concentration of about 0.01 to about 0.5 mg/ml.

Additionally useful additives can be readily determined by those of skill in the art according to the particular needs or intended uses of the compositions and formulator. One such particularly useful additional substance is sodium chloride, which is useful for adjusting the osmolality of the formulations to achieve the desired resulting osmolality. Particularly preferred osmolalities for parenteral administration of the disclosed compositions are in the range of about 270 to about 330 mOsm/kg. The optimal osmolality for parenterally administered compositions, particularly injectables, is approximately 300 mOsm/kg and achievable by the use of sodium chloride in concentrations of about 6.5 to about 7.5 mg/ml with a sodium chloride concentration of about 7.0 mg/mi being particularly effective.

VI-SMR peptides can be stored as a lyophilized powder under aseptic conditions and combined with a sterile aqueous solution prior to administration. The aqueous solution used to resuspend the peptides can contain pharmaceutically acceptable auxiliary substances as required to approximate physical conditions, such as pH adjusting and buffering agents, tonicity adjusting agents and the like, as discussed above. Alternatively, the VI-SMR peptides can be stored as a suspension, preferable an aqueous suspension, prior to administration.

The pharmaceutical composition of the present disclosure is formulated to be compatible with its intended route of administration. Examples of routes of administration include parenteral, e.g., intrathecal, intra-arterial, intravenous, intradermal, subcutaneous, oral, transdermal (topical) and transmucosal administration. Solutions or suspensions used for parenteral, intradermal, or subcutaneous application can include the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the requited particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the VI-SMR peptide in the required amount in an appropriate solvent with one or a combination of ingredients enumerated above, as required, followed by filtered sterilization. Generally, dispersions are prepared by incorporating the VI-SMR peptide into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active peptide plus any additional desired ingredient from a previously sterile-filtered solution thereof.

Oral compositions generally include an inert diluent or an edible carrier. They can be enclosed in gelatin capsules or compressed into tablets. The tablets, pills, capsules, troches and the like can contain any of the following ingredients, or compounds of a similar nature, including a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

For administration by inhalation, the peptides are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the pharmaceutical compositions are formulated into ointments, salves, gels, or creams as generally known in the art.

In certain embodiments, the pharmaceutical composition is formulated for controlled or delayed release of the active ingredient. For example, in certain embodiments, the peptides may be delivered from with an enteric coating applied as a barrier to an oral formulation so as to prevent release of the peptides before they reach the small intestine. As used herein, the term "enteric coating" is a coating comprising of one or more polymers having a pH dependent or pH-independent release profile. An enteric coated pill will not dissolve in the acidic juices of the stomach (pH~3), but they will in the alkaline (pH 7-9) environment present in the small intestine or colon. An enteric polymer coating typically resists releases of the active agents until sometime after a gastric emptying lag period of about 3-4 hours after administration.

Such enteric coatings or barrier coatings are also used to protect acid-unstable peptides from the stomach's acidic exposure, delivering them instead to a basic pH environment (intestine's pH 5.5 and above) where they do not degrade and can mediate their desired action. An oral formulation may comprise a plurality of barrier coatings comprising a variety of different materials to facilitate release in a temporal manner. The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols, and/or polyvinylpyrrolidone) or a coating based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose. Furthermore, the formulation may additionally include a time delay material such as glyceryl monostearate or glyceryl distearate.

Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from e.g. Alza Corporation and Nova Pharmaceuticals, Inc. Liposomal suspensions (including liposomes targeted to infected cells with monoclonal antibodies to tumor antigens or viral antigens) can also be used as pharmaceutically acceptable carriers.

It is especially advantageous to formulate the peptide compositions in dosage unit form for ease of administration and uniformity of dosage. Suitable unit dosage forms include, but are not limited to powders, tablets, pills, capsules, lozenges, suppositories, patches, nasal sprays, injectibles, implantable sustained-release formulations, lipid complexes, etc.

Routes and Dosages of VI-SMR Peptide for Administration

The antiviral VI-SMR peptide of the present application may be administered by any route, including but not limited to any of the various parenteral, gastrointestinal, inhalation, and topical (epicutaneous) routes of administration. Parenteral administration generally involves injections or infusions and includes, for example, intravenous, intraarterial, intratumoral, intracardiac, intramuscular, intravesicular (e.g., to the bladder), intracerebral, intracerebroventricular, intraosseous infusion, intravitreal, intaarticular, intrathecal, epidural, intradermal, subcutaneous, transdermal, and intraperitoneal administration. Gastrointestinal administration includes oral, buccal, sublingual and rectal administration. The route of administration may involve local or systemic delivery of the VI-SMR peptides.

As a general proposition, the therapeutically effective amount of a VI-SMR peptide administered will be in a weight range of about 1 ng/kg body weight/day to about 100 mg/kg body weight/day whether by one or more administrations. In more particular embodiments, the antiviral VI-SMR peptide or VI-SMR peptide-containing formulation is administered in weight range from about 1 ng/kg body weight/day to about 1 µg/kg body weight/day, 1 ng/kg body weight/day to about 100 ng/kg body weight/day, 1 ng/kg body weight/day to about 10 ng/kg body weight/day, 10 ng/kg body weight/day to about 1 µg/kg body weight/day, 10 ng/kg body weight/day to about 100 ng/kg body weight/day, 100 ng/kg body weight/day to about 1 µg/kg body weight/day, 100 ng/kg body weight/day to about 10 µg/kg body weight/day, 1 µg/kg body weight/day to about 10 µg/kg body weight/day, 1 µg/kg body weight/day to about 100 µg/kg body weight/day, 10 µg/kg body weight/day to about 100 µg/kg body weight/day, 10 µg/kg body weight/day to about 1 mg/kg body weight/day, 100 µg/kg body weight/day to about 10 mg/kg body weight/day, 1 mg/kg body weight/day to about 100 mg/kg body weight/day and 10 mg/kg body weight/day to about 100 mg/kg body weight/day.

In other embodiments, a VI-SMR peptide is administered at a dosage range of 1 ng-10 ng per injection, 10 ng-100 ng per injection, 100 ng-1 µg per injection, 1 µg-10 µg per injection, 10 µg-100 µg per injection, 100 µg-1 mg per injection, 1 mg-10 mg per injection, 10 mg-100 mg per injection, and 100 mg-1000 mg per injection. The VI-SMR peptide or VI-SMR peptide-containing formulation may be injected once daily, twice daily, three times daily, and/or every 2, 3, 4, 5, 6 or 7 days. In addition, the VI-SMR peptide or VI-SMR peptide-containing formulation may be administered over a period of one month, two months, six months, 12 months, 2 years, 5 years, 10 years, 20 years, or more.

In other embodiments, the antiviral VI-SMR peptide or VI-SMR peptide-containing formulation may be administered in a range from about 1 ng/kg to about 100 mg/kg. In more particular embodiments, the antiviral VI-SMR peptide or VI-SMR peptide-containing formulation may be administered in a range from about 1 ng/kg to about 10 ng/kg, about 10 ng/kg to about 100 ng/kg, about 100 ng/kg to about 1 µg/kg, about 1 µg/kg to about 10 µg/kg, about 10 µg/kg to about 100 µg/kg, about 100 µg/kg to about 1 mg/kg, about 1 mg/kg to about 10 mg/kg, about 10 mg/kg to about 100 mg/kg, about 0.5 mg/kg to about 30 mg/kg, and about 1 mg/kg to about 15 mg/kg.

In other particular embodiments, the amount of antiviral VI-SMR peptide administered is, or is about, 0.0006, 0.001, 0.003, 0.006, 0.01, 0.03, 0.06, 0.1, 0.3, 0.6, 1, 3, 6, 10, 30, 60, 100, 300, 600 and 1000 mg/day.

The specific dose of VI-SMR peptide is determined by the particular circumstances of the individual patient including the size, weight, age and sex of the patient, the nature and stage of the disease, the aggressiveness of the disease, and the route of administration of the pharmaceutical composition.

In certain embodiments, the VI-SMR peptide may be administered at least once per day, typically once, twice, three times or four times per day with the doses given at equal intervals throughout the day and night in order to maintain a constant presence of the drug in order to provide sufficient efficacy. However, a skilled artisan will appreciate that a treatment schedule can be optimized for any given patient, and that administration of compound may occur less frequently than once per day.

In other embodiments, a VI-SMR peptide or VI-SMR peptide-containing formulation of the present application is prescribed to be taken in combination with other antiviral agents and/or the other active agents described above. Examples of other antiviral agents include, but are not limited to, antibiotics, other antiviral peptides, and in vivo expression vectors that encode a VI-SMR peptide of the present application. When used in such combinations, the antiviral VI-SMR peptide of the present application and other antiviral agents may be administered simultaneously, by the same or different routes, or at different times during treatment.

The treatment may be carried out for as long a period as necessary, i.e., until the infection is cleared or no longer a threat to the host. In some cases, the treatment may be continued indefinitely while the disease state persists, although discontinuation might be indicated if the antiviral compositions no longer produce a beneficial effect. In one embodiment, the treatment is carried out for 6 months and then discontinued. The treating physician can determine whether to increase, decrease, or interrupt treatment based on a patient's response, including evaluation of immune responses, viral loads etc.

Dosage unit form as used herein includes physically discrete units suited as unitary dosages for the subject to be treated; each unit containing a predetermined quantity of the VI-SMR peptide calculated to produce the desired therapeutic effect in association with the required pharmaceutical carrier. The specification for the dosage unit forms of the disclosure are dictated by and directly dependent on the unique characteristics of the VI-SMR peptide and the particular therapeutic effect to be achieved.

Data obtained from the cell culture assays and animal studies can be used in formulating a range of dosage for use in humans. The dosage of such peptides lies preferably within a range of circulating concentrations that include the ED50 with little or no toxicity. The dosage may vary within this range depending upon the dosage form employed and the route of administration utilized. For any peptide used in the methods of the present disclosure, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. The pharmaceutical compositions can be included in a container, pack, or dispenser together with instructions for administration.

The present application is further illustrated by the following examples that should not be construed as limiting. The contents of all references, patents, and published patent applications cited throughout this application, as well as the Figures and Tables, are incorporated herein by reference.

EXAMPLES

Example 1: Materials and Methods 1.1. Cell lines, reagents and antibodies. The MCF-7 cell line, a noninvasive estrogen receptor positive (ER+) and MDA-MB-231 cell line (ER negative) were purchased from the American Type Culture Collection (ATCC, Manassas, Va.). MCF-10A cell line, an epithelial cell line was also purchased from ATCC. 3-(4,5-dimethylthiazol-2-yl)-2, 5-diphenyltetrazolium (MTT), Dulbecco's Modified Eagle's Medium (DMEM) with high glucose and FLUORO-BRITE™ phenol red-free DMEM, (MCF-7) were purchased from Thermo Fisher Scientific (Rockford, Ill.) The RPMI 1640 medium (MDA-MB-231 cells) was obtained from Life Technologies Company (Carlsbad, Calif.). The basal medium MEBM and the additive MEGM (MCF-10A cells) were obtained from Lonzal/Clonetics Corporation (Lonza, Walkersville, Md.). The CD63 Rabbit polyclonal and Alix goat polyclonal antibodies were purchased from Santa Cruz Biotechnology Inc. (Santa Cruz, Calif.). The PEG-SMRwt-Clu PEG-SMRwt and PEG-SMRmut HIV-1 Nef peptides were purchased from InnoPep Company (San Diego, Calif.).

1.2. Cell culture. Cells were cultured in the media described above with addition of exosome-free fetal bovine serum (System Biosciences Inc., Mountain View, Calif.), 100 units/mL penicillin, and 100 mg/mL streptomycin and maintained in a humidified atmosphere at 37° C. and 5% $CO_2$.

1.3. EV isolation and purification. EVs were isolated from cells by differential centrifugation as previously described (Ali SA. et al., 2010). Untreated cells were used as a control. Briefly, the above treated and untreated cell culture supernatants were centrifuged at 400×g for 10 minutes. The supernatants were transferred to a clear tube and centrifuged at 10,000×g for 30 minutes. The supernatants from the second spin were ultracentrifuged at 400×g for 10 minutes. The supernatants were transferred to a clear tube and centrifuged at 10,000×g for 30 minutes. The supernatants from the second spin were ultracentrifuged at 200,000×g for 2 hours to pellet the EVs. Finally, the EV pellets were re-suspended with PBS and stored at 4° C. until used for analysis.

1.4. Exosome characterization by acetylcholinesterase (AchE) assay. Purified EVs were quantitated by measurement of AchE as described (Ellman et al., 1961). Briefly, a 100 mM dithibionitrobenzoic (DTNB) solution was prepared for use as a stock color indicator, and a 28.9 mg/mL acetylthiocholine iodide in PBS solution was prepared as a stock substrate. The stock substrate stock can be stored at −20° C. up to one month, while the color indicator can be stored at 4° C. for two weeks. A working solution was prepared by mixing 10 mL of PBS with 200 μL of Substrate and 500 μl of DTNB. 50 μL of each exosome sample was transferred to 96 well microtitre plates, and a standard curve was prepared using AchE from 0.98 mU/mL to 2000 mU/mL. After 50 μL of standards were added into separate wells, 200 μL of the working solution was added to all wells. After 20 min incubation, AchE activity was measured at 450 nm using a SpectroMax M5 fluorimeter.

1.5. EV nanoparticle tracking analysis (NTA). Analysis of absolute size distribution of EVs was performed using NanoSight LM10 with NTA2.3 (NanoSight Ltd., Minton Park, UK). EV particles were automatically tracked and sized based on Brownian motion and the diffusion coefficient. After isolation, the untreated and treated EVs were re-suspended in 0.5 mL of PBS. Control medium and filtered PBS were used as controls in this technique. The NTA measurement conditions were: temperature=21.0+/−0.5° C.; viscosity=0.99+/−0.01 cP; frames per second=25; measurement time=30 s. The detection threshold was similar in all samples. Two recordings were performed for each sample.

1.6. Western blot analysis. EVs were isolated from culture supernatants as described above. Protein concentrations were determined by measuring absorbance at 280 nm (Nanodrop 2000). Protein samples were denatured in SDS-PAGE sample buffer by heating at 95° C. for 15 min. Criterion TGX Precast Gels (4-20% Bio-Rad, Richmond, Calif.) were used to separate the proteins and blotted as previously described (Huang MB. et al 2004). Blots were incubated with the primary antibodies, anti-CD63 and anti-Alix, followed by goat or rabbit anti-Ig secondary antibodies. Specific bands were detected using ECL chemiluminescent substrate (Santa Cruz Biotechnology, Santa Cruz, Calif.) and visualized on the ImageQuant LAS 4000 imaging system (GE Healthcare, Piscataway, N.J. 08854).

1.7. Fluorescent N—Rh-PE measurement. The fluorescent phospholipid analog N—Rh-PE [N-(lissamine rhodamine B sulfonyl) phosphatidyl ethanolamine] is a lipid marker of EVs, including exosomes and intraluminal vesicles of multivesicular bodies as previously described (Willem J et al., 1990). Briefly, 10 mM of the N—Rh-PE was stored in chloroform/methanol (2:1). A 5 μM N—Rh-PE solution in a pre-cooled reaction medium was then added to the treated with MCF-7 cells transfected with siRNA-Negative or siRNA-HSPA9, and then were incubated at 4° C. for 1 h. After this incubation period, the medium was removed and the cells were extensively washed with cold medium to remove excess unbound lipids. Labeled cells were cultured in complete RPMI-1640 with 10% exosome-depleted FBS medium heat inactivated at 37° C. overnight. Measurement of N—Rh-PE in the collected supernatants/EVs was carried out using a spectrometer at 550 nm and 590 nm excitation and emission wavelengths, respectively.

1.8. Transfection with mortalin antibody. MCF-7 cells were transfected with mortalin antibody using a Chariot kit (Active Motif, Carlsbad, Calif.) in accordance with the manufacturer's protocol. Following a 48 hour incubation of these cells, the EVs were isolated and measured via AchE assay and NanoSight analysis.

1.9. Transient transfection with small interfering RNA (siRNA). MCF-7 cells were transfected with double-stranded siRNAs using Amaxa's Nucleofector kit (Lonza Walkersville Inc., Walkersville, Md.) in accordance with the manufacturer's protocol. Transfection of plasmids was carried out using Amaxa Biosystems Nucleofector II as recommended by the supplier. Mortalin siRNAs were prepared as previously described (Shelton et al., J Virol (2012) 86(1): p. 406-19). Following transfection, the cells were incubated at 37° C. for 24, 48, 72 and 96 hours, and EVs were isolated and measured by AchE assay and Western blotting.

1.10. Statistical analysis. Data was expressed as the mean±standard deviation (S.D.). A two-sample t—Test assuming equal variances was used to compare the differences between controls and treated samples in each group. A value of $p<0.05$ was considered to be statistically significant.

Example 2: SMR Peptides Block Exosome Release

Acetylcholinesterase (AchE) assays, NanoSight analysis and Western blot analysis were performed to characterize EVs released from MCF-7 and MDA-MB-231 cells treated for 48 hr with the various peptides. The results indicated that exosome release was inhibited by the SMRwt peptides.

AchE activity in EVs was assayed and the results of this analysis are shown in FIG. 1, Panels A and B. In MCF-7 cells, the control EVs were found to contain 113.49 mU/mL of AchE activity. In contrast, 41.95 mU/mL of activity was found in cells treated with PEG-SMRwt-CLU peptide; 51.87 mU/mL activity was found in cells treated with PEG-SMRwt-CLU in combination with paclitaxel; and 16.95 mU/mL activity was found in cells treated with PEG-SMRwt-CLU in combination with (FIG. 1, Panel A). In MDA-MB-231 cells, the control EVs contained 118.48 mU/mL of AchE activity, whereas 66.77 mU/mL activity was found in cells treated with PEG-SMRwt-CLU peptide; 64.15 mU/mL activity was found in cells treated with PEG-SMRwt-CLU peptide in combination with paclitaxel; and 27.0 mU/mL activity was found in cells treated with PEG-SMRwt-CLU in combination with cisplatin (FIG. 1, Panel B).

Figure 4:
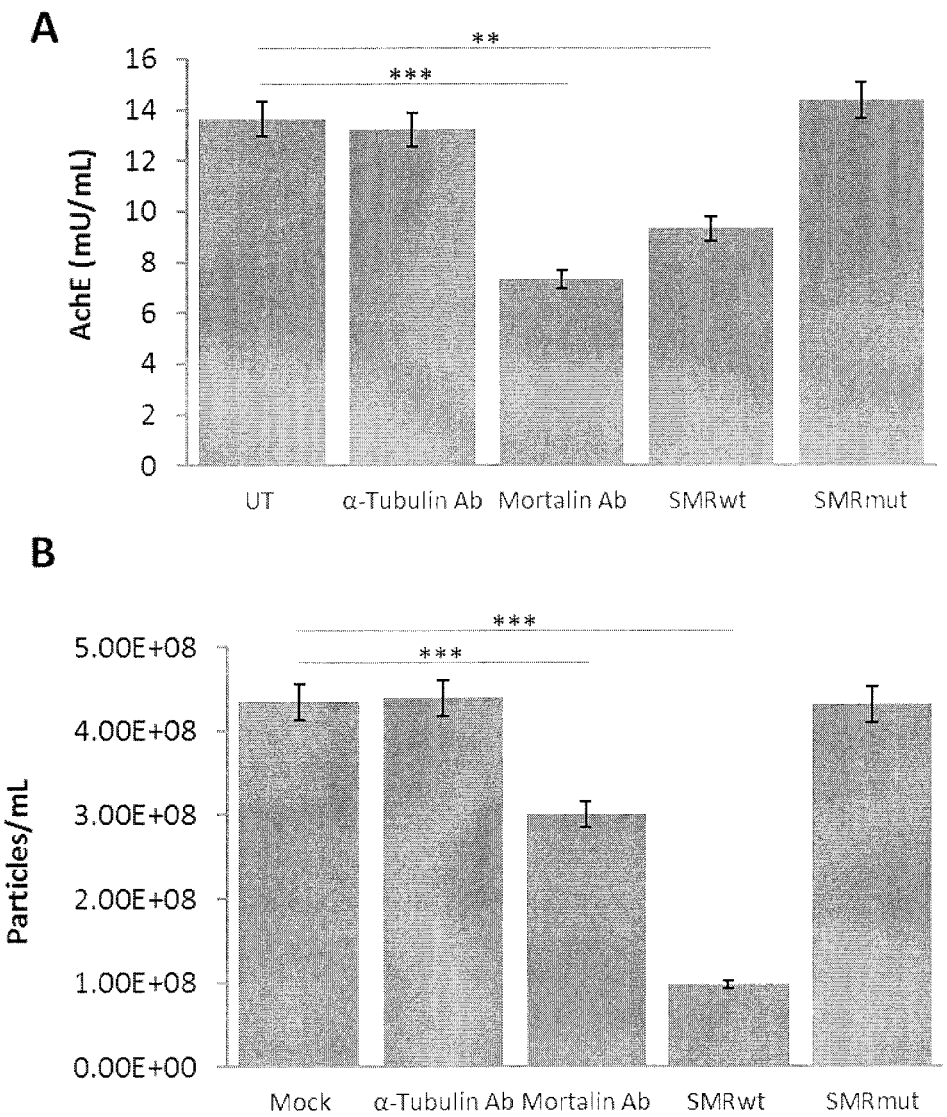
FIG. 4 shows that antibody to mortalin inhibits exosome secretion from MCF-7 cells. MCF-7 cells were either transfected with antibodies to mortalin or alpha-tubulin, or treated with SMRwt or SMRmut peptides. Panel A: Relative exosome release level after 48 hr by AchE assay. Panel B: Relative numbers of exosomes released after 48 hr by NanoSight analysis. Error bars represent the mean±SD of three independent experiments. Significant differences relative to untreated cells: *p<0.0001, **p<0.0001.

Analysis of exosome concentrations and size distributions was assayed by NanoSight LMI0 Nanoparticle Tracking Analysis (NTA). With NTA, particles are automatically tracked and sized based on Brownian motion and the associated diffusion coefficient. Before analysis of the samples by NT A, it was determined that salt aggregates from the PBS did not contribute to background and the equipment was free of contaminant particles. The untreated MCF-7 cell control medium showed a considerable number of particles ($5.16 \times 10^9$ particles/ml) (FIG. 1, Panel C). However, a reduced number of particles was found in MCF-7 cells treated with PEG-SMRwt-CLU ($3.28 \times 10^8$ particles/ml, $p<2.40E-06$), PEG-SMRwt-CLU in combination with paclitaxel ($5.7 \times 10^8$ particles/mL, $p<0.0008$) and PEG-SMRwt-CLU in combination with cisplatin ($3.77 \times 10^8$ particles/mL, $p<0.0001$) (FIG. 4, Panel C).

Similarly, whereas control media from MDA-MB-231 cultures also showed a considerable number of particles ($4.7 \times 10^9$ particles/ml), a reduced number of particles was found in MDA-MB-231 cells treated with PEG-SMRwt-CLU peptide ($6.8 \times 10^8$ particles/ml, $p<3.96E-05$), PEG-SMRwt-CLU peptide in combination with paclitaxel ($7.5 \times 10^8$ particles/mL, $p<0.001$) and PEG-SMRwt-CLU peptide in combination with cisplatin ($3.06 \times 10^8$ particles/mL, $p<5.37E-05$) (FIG. 1, Panel D). By NTA analysis, the size of the EVs was estimated to range between 30 to 47 nm in both cell lines.

Figure 2:
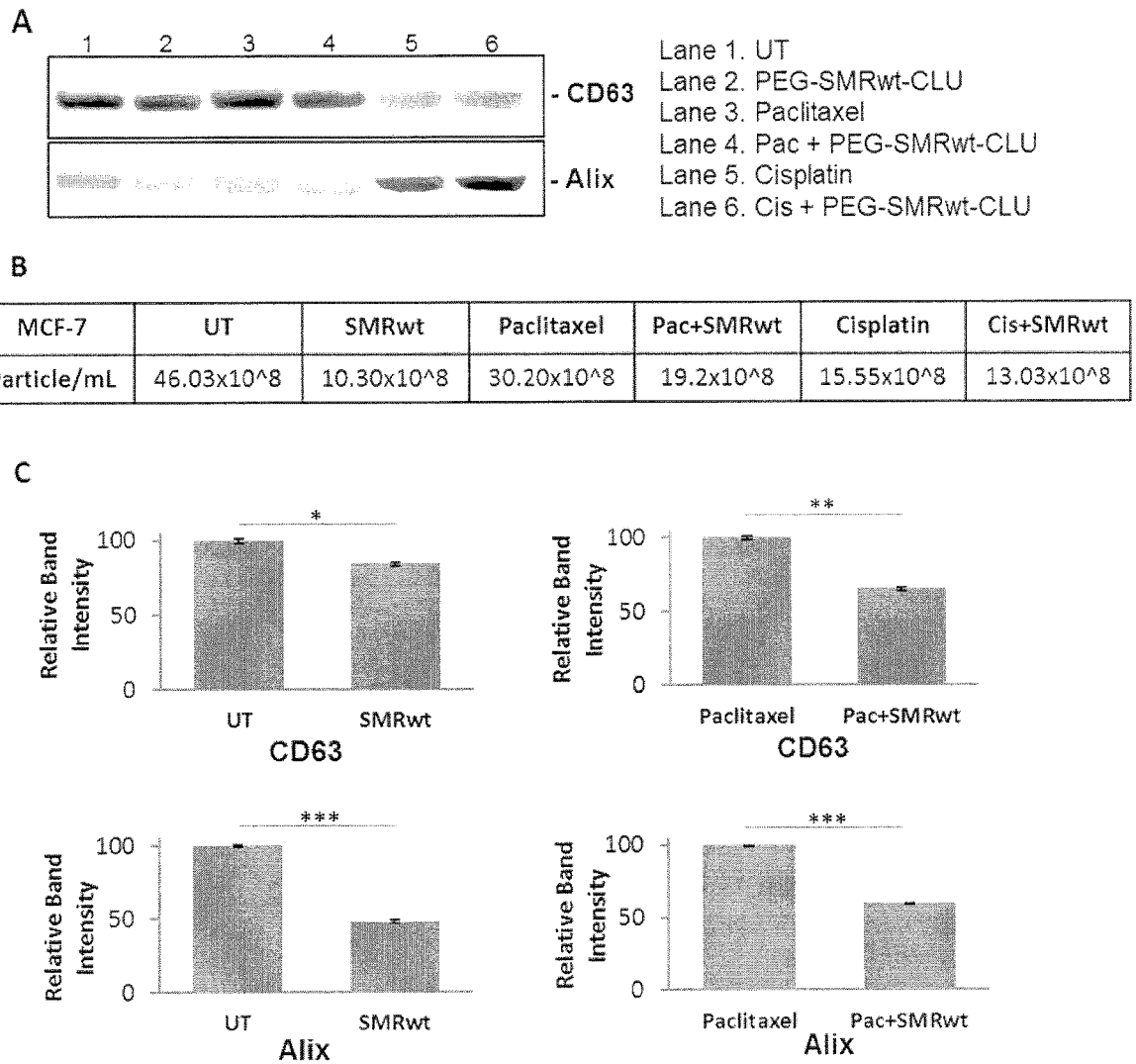
FIG. 2 shows that exosome-specific proteins can be detected on exosomes from MCF-7 cells. Cells were treated for 48 hr with SMRwt peptide alone or combined with paclitaxel or cisplatin. Panel A: Expression of exosome proteins by Western blot analysis. Panel B: Exosome numbers were measured by NanoSight. Panel C: Densitometry analysis showing relative intensity of bands. Data represent the mean+SD of three independent experiments. Significant differences relative to treatment with peptide are indicated as follows: *p<0.01,  p<0.001, *p<0.0001.
Figure 3:
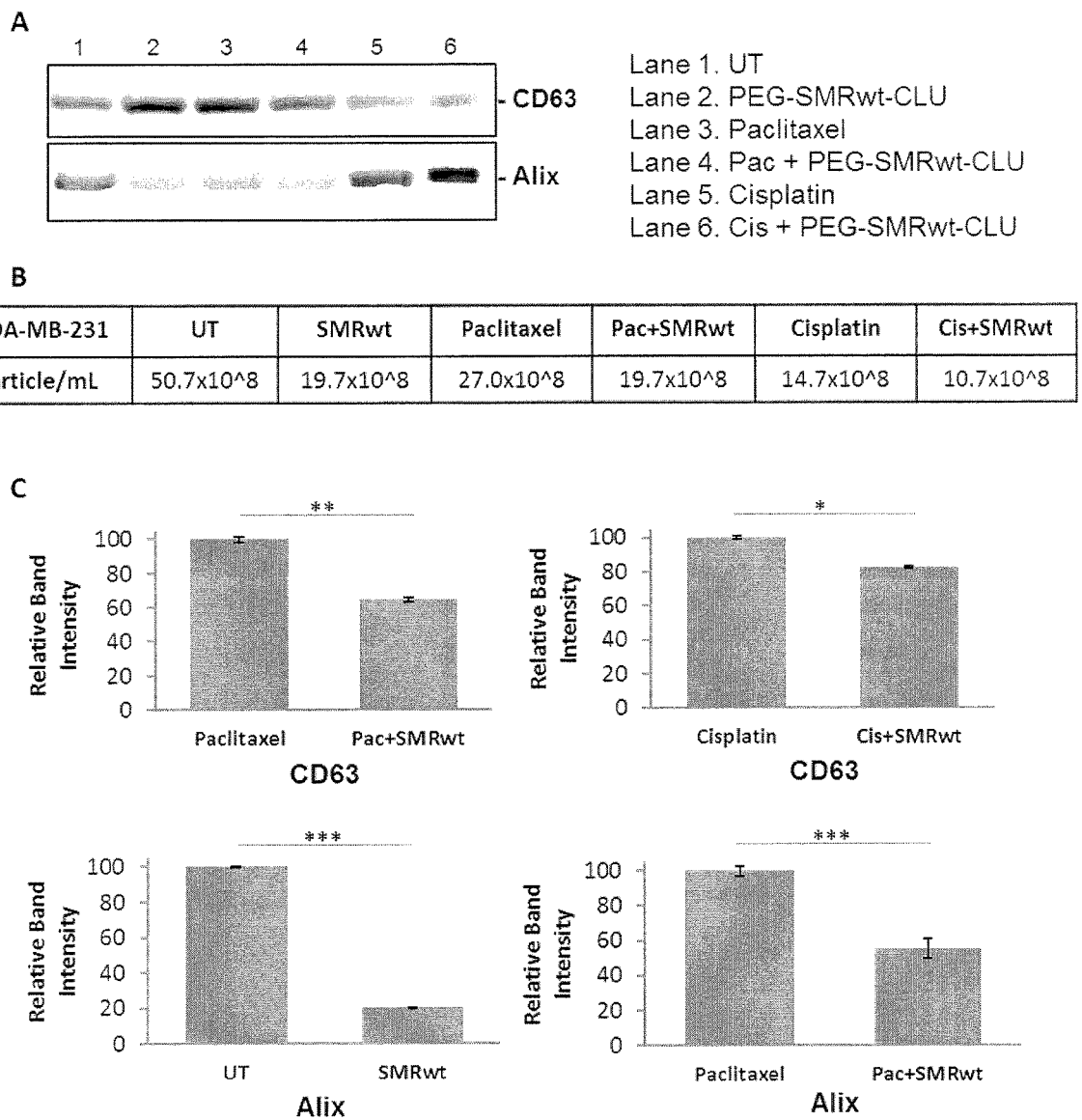
FIG. 3 shows that exosome-specific proteins can be detected on exosomes from MDA-MB-231 cells. Cells were treated for 48 hr with SMRwt peptide alone or combined with paclitaxel or cisplatin. Panel A shows Expression of exosome proteins by Western blot analysis. Exosome numbers were measured by NanoSight (Panel B) and densitometry analysis shows relative intensity of bands (Panel C). Data represent the mean+SD of three independent experiments. Significant differences relative to treatment with peptide are indicated as follows: p<0.01, p<0.001, **p<0.0001.

Finally, Western blot analysis was used to detect EV proteins in control- and peptide-treated cultures. The results of this analysis revealed the presence of human CD63 and Alix markers in the all EVs isolated from MCF-7 cells (FIG. 2) and MDA-MB-231 cells (FIG. 3). Control EVs showed higher expression of human CD63 from MCF-7 cells and higher expression of Alix from MDA-MB-231 cells.

Example 3: Blocking the SMR-Mortalin Interaction Blocks Exosome Release

A previous study identified the HSP70 family protein, mortalin (encoded by HSPA9) as a binding partner for HIV-1 Nef SMR, and showed that disruption of HIV-1 Nef SMR-mortalin binding interfered with exosome release (Shelton et al., J Virol (2012) 86(1): p. 406-19). To test whether an analogous interaction accounts for the observed PEG-SMRwt-CLU effect on exosome release, MCF-7 cells were transfected with antibody to mortalin or antibody to a-tubulin as a control. The anti-mortalin treated cells were found to be significantly impaired in EV release as measured by AchE assay (FIG. 4, Panel A) and slightly less so when measured by NTA assay (FIG. 4, Panel B). The effect of treatment with anti-mortalin was similar to the effect of treating MCF-7 cells with PEG-SMRwt-CLU peptide.

Figure 5:
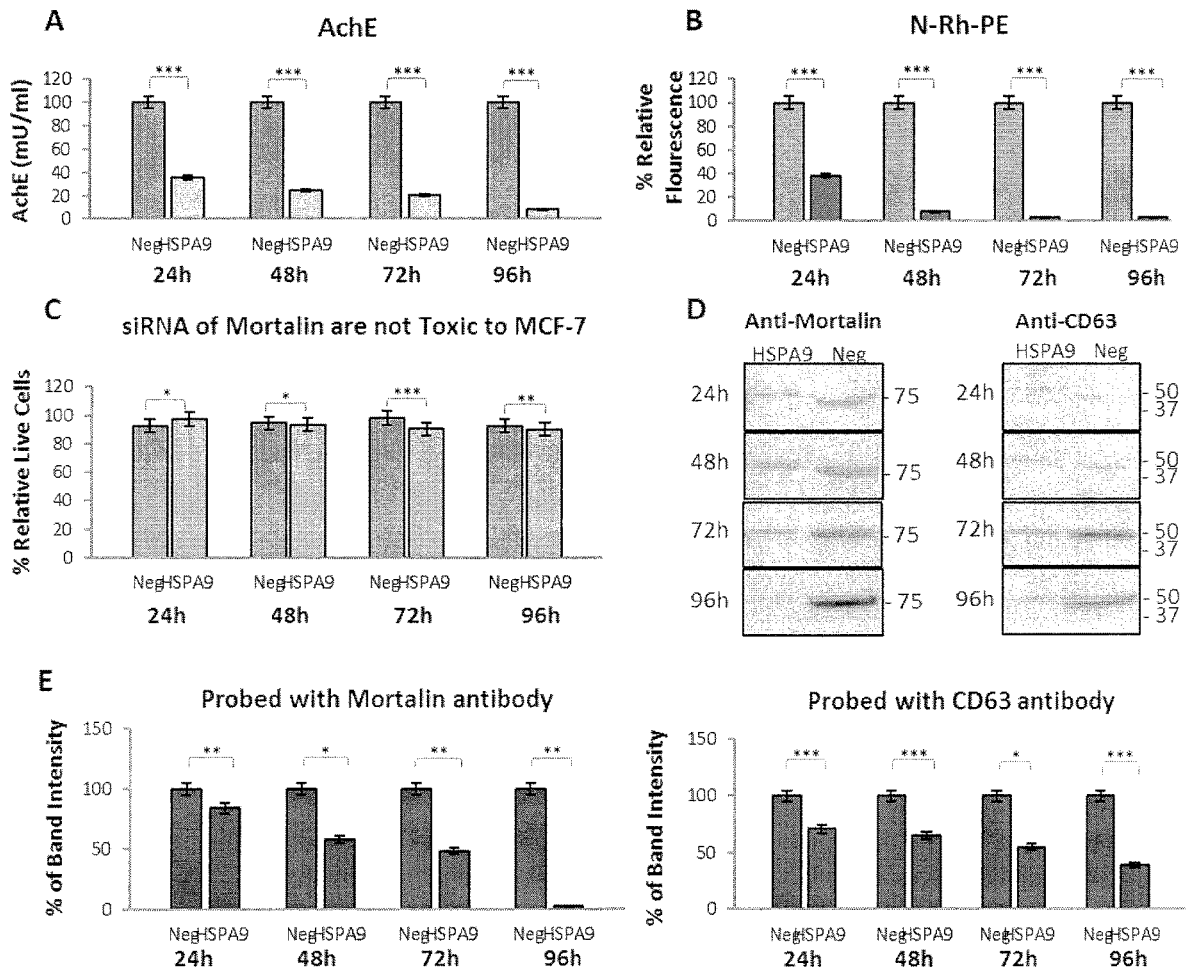
FIG. 5 shows exosome secretion is decreased in MCF-7 cells by knockdown of mortalin expression. MCF-7 cells were transfected with clones expressing siRNA against either mortalin (HSPA9) or a negative control RNA. Exosomes were isolated and analyzed after 24, 48, 72, and 96 hr for changes in level of exosome secretion by AchE assay (Panel A). Significant differences relative to controls are indicated: *p<0.0001, and exosome secretion by N—Rh-PE (Panel B). Significant differences relative to controls are indicated: *p<0.0001. Panel C: percentage of live cells remaining at each time point,*p<0.05, p<0.002, *p<0.0001. Panel D: mortalin and CD63 protein expression levels by Western blotting. Panel E: Densitometry analysis of Western blot data. Significant differences relative to controls are indicated:*p<0.01, p<0.001, *p<0.0001.

To further validate the significance of this mortalin-mediated process, expression of mortalin protein was knocked down by transfecting MCF-7 cells with a plasmid construct expressing a mortalin siRNA. The mortalin siRNAs were found to block EV secretion as evidenced by AchE assay and membrane fluorescence (N—Rh-PE) assays at all timepoints tested (FIGS. 5, Panels A and B) in the absence of any cell toxicity (FIG. 5, Panel C). The EVs from siRNA-transfected cells were further assayed for expression of mortalin and the exosome marker CD63, a tetraspanins by Western blot analysis. The results of this analysis showed that expression of both mortalin and CD63 was significantly decreased at 48 hon through to 96 h (FIG. 5, Panels D and E).

Example 4: SMRwt Peptides and Mortalin Inhibitors Block EV Release

Figure 6:
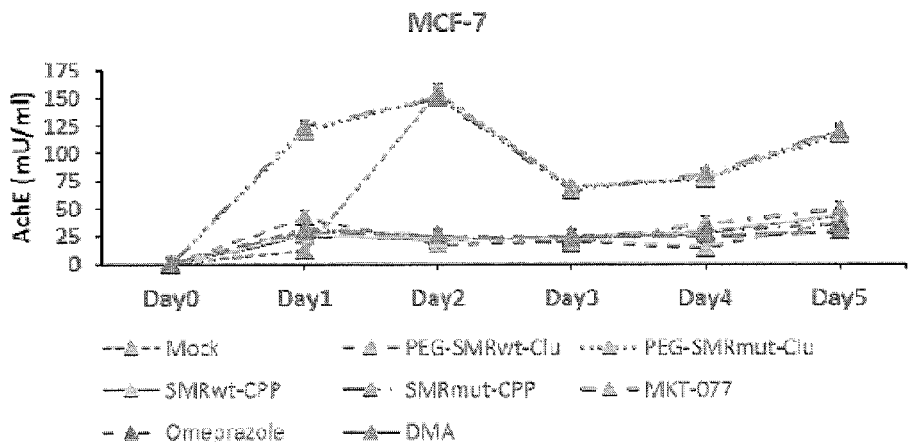
FIG. 6 shows that treatment of MCF-7 cells, MDA-MB-231 cells and K562 cells with PEG-SMRwt-Clu peptide, SMRwt-CPP peptide, or the mortalin inhibitors, MKT-077, Omeprazole or 5-(N,N-dimethyl)amiloride (DMA) blocked exosome release. Each of these three cell types were treated with PEG-SMRwt-Clu peptide, PEG-SMRmut-Clu peptide, SMRwt-CPP peptide, SMRmut-CPP peptide, MKT-077, Omeprazole or DMA for five days at 37° C. Panels A, B and C show levels of exosome release from MCF-7 cells, MDA-MB-231 cells, and K562 cells, respectively, as determined by an acetylcholinesterase (AchE) assay.
Figure 6:
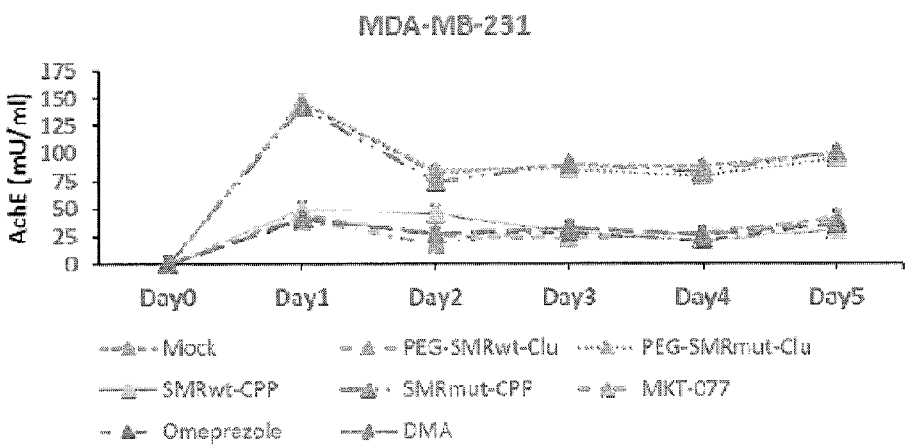
Figure 6:
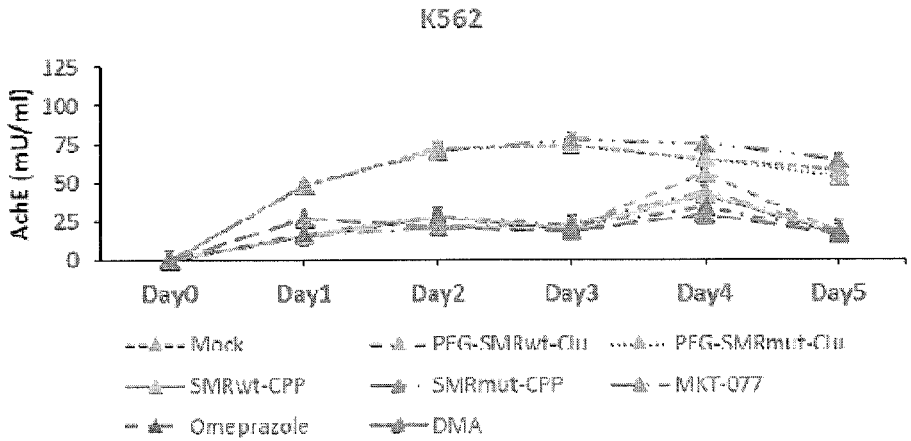

PEG-SMRwt-Clu peptide was previously shown to block exosome release (Huang et al., Oncotarget (2017) 8(7): p. 11302-11315). To further examine the underlying mechanism for blocking exosome release, a study was extended to examine the effects of the SMRwt peptides, PEG-SMRwt-Clu peptide and SMRwt-CPP peptide, and the mortalin inhibitors MKT-077, Omeprazole, and DMA on exosome release. In particular, acetylcholinesterase (AchE) assays, NanoSight analysis and Western blot analysis were performed to characterize EVs released from MCF-7, MDA-MB-231 and K562 cells. Cells were treated for five days at 37° C. with the various peptides and mortalin inhibitors as indicated in FIG. 6. Panels A, B and C depict the relative numbers of EVs released as a function of time as measured by an acetylcholinesterase (AchE) assay in MCF-7 cells (FIG. 6, Panel A); MDA-MB-231 cells (FIG. 6, Panel B); and K562 cells (FIG. 6, Panel C).

The results of this analysis showed that the SMRwt-CPP peptide, (SEQ ID NO: 4), PEG-SMRwt-Clu peptide, VGFPVAAVGFPVHPLSKHPYWSQP (SEQ ID NO: 47), and the mortalin inhibitors, MKT-077, Omeprazole and DMA all reduced the number of EVs released over the entire five day treatment period. As shown in FIG. 6, Panels A-C, there was an initial increase in exosome release on days 1 and/or 2 under all treatment conditions and a subsequent decrease in EV release thereafter, although the initial increases and subsequent decreases were substantially reduced in cells treated with the SMRwt peptides or mortalin inhibitors. In particular, AchE concentrations in MCF-7 cells treated with the negative controls (i.e., mock, PEG-SMRmut-Clu, and SMRmut-CPP were 155.13 mU/mL, 151.5 mU/mL and 150.06 mU/mL, respectively. On day 3, a rapid decrease was observed under these treatment conditions (69.15 mU/mL, 69.0 mU/mL and 66.05 mU/mL) with a subsequent increase in AChE concentrations on day 4 and day 5.

In contrast, MCF-7 cells treated with PEG-SMRwt-Clu, SMRwt-CPP, MKT-077, Omeprazole, and DMA were found to exhibit reduced AChE concentrations throughout days 1 to day 5, wherein the average AChE concentrations were 31 mU/mL, 22 mU/mL, 22 mU/mL 26 mU/mL and 26 mU/mL, respectively.

FIG. 6, Panel B shows the results obtained for similar treatments in MDA-MB-231 cells. In this case, initial increases in AChE of 146.52 mU/mL, 146.79 mU/mL and 141.47 mU/mL were observed on day 1 for mock, PEG-SMRmut-Clu, and SMRmut-CPP treatments, respectively, which were followed by decreases in AChE concentrations on days 2-5. In MDA-MB-231 cells treated with PEG-SMRwt-Clu, SMRwt-CPP, MKT-077, Omeprazole, and DMA, however, the AChE levels were maintained at average concentration levels throughout day 1 to 5 of 42 mU/mL, 29 mU/mL, 29 mU/mL, 25 mU/mL and 37 mU/mL, respectively.

FIG. 6, Panel C shows the results obtained for similar treatments in K562 cells. In this case, average AChE levels in the negative control groups from days 1 to 5 were 48 mU/mL, 71 mU/mL, 75 mU/mL, 69 mU/mL and 59 mU/mL, respectively. By contrast, average AChE levels on days 1-3 and 5 in K562 cells treated with PEG-SMRwt-Clu, SMRwt-CPP, MKT-077, Omeprazole, and DMA were 18 mU/mL, 25 mU/mL, 21 mU/mL and 18 mU/mL with day 4 showing an increase relative to the other days (i.e., 41 mU/mL). These results further confirm that EV release was inhibited by all experimental treatments (FIG. 6).

Example 5: Effect of SMRwt Peptides and Mortalin Inhibitors on EV Protein Content Western blot analysis was used to examine the effects of the SMRwt peptides, PEG-SMRwt-Clu peptide and SMRwt-CPP peptide, and the mortalin inhibitors MKT-077, Omeprazole, and DMA on EV protein content in MCF-7, MDA-MB-231 and K562 cells. Negative control treatments included the PEG-SMRmut-Clu peptide, NXNAGFPVAAAGFPVHPLSKHPYWSQP (SEQ ID NO: 49) and the SMRmut-CPP peptide, AGFPVAAAGFPVGRKKRRQRRRPPQ (SEQ ID NO: 50). EVs were isolated from all treated and untreated cell lines screened. Western blot analyses were carried out to evaluate the expression levels of the exosomal proteins, Alix, mortalin, and vimentin in MCF-7 cells (FIG. 7, Panel A, left sub-panel), MDA-MB-231 cells (FIG. 7, Panel A, middle sub-panel), and K562 cells (FIG. 7, Panel A, right sub-panel).

Figure 7:
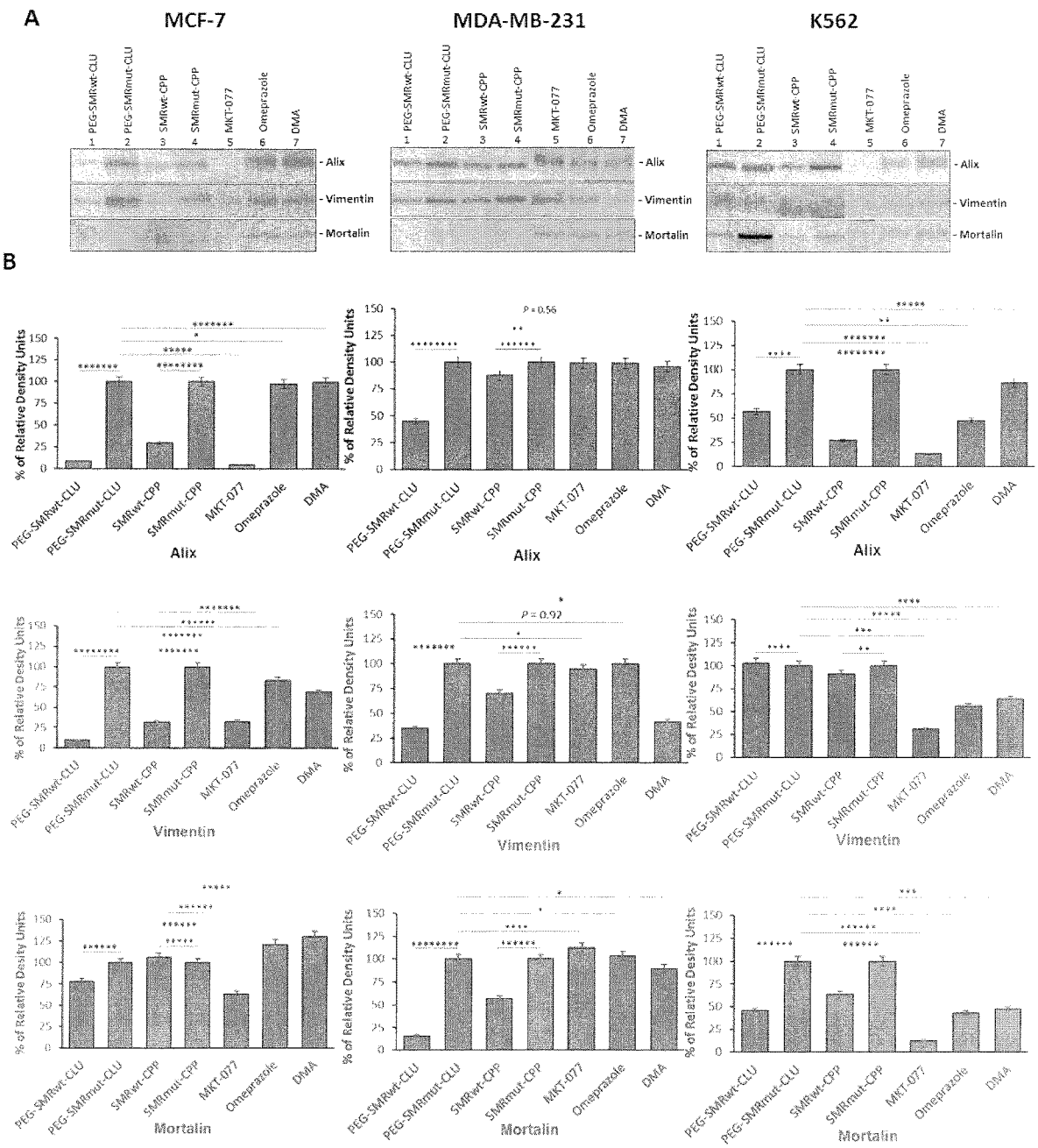
FIG. 7 shows detection of mortalin, vimentin and the exosome-specific ALIX protein in exosomes released from MCF-7 cells, MDA-MB-231 cells and K562 cells treated with PEG-SMRwt-Clu, PEG-SMRmut-Clu, SMRwt-CPP, SMRmut-CPP, MKT-077, Omeprazole or DMA for 48 hours at 37° C. Western blot analysis was carried out using anti-mortalin (Grp-75), anti-Vimentin and anti-Alix antibodies to evaluate mortalin, vimentin and exosomes expression. Panel A shows gel images of the exosome products, mortalin, vimentin and Alix in MCF-7, MDA-MB-231 and K562 cells; Panel B shows band intensities of the exosome products mortalin, vimentin and Alix in MCF-7 and MDA-MB-231 cells and K562 cells. Quantitative results from Western blots were obtained by densitometry analysis of relative band intensities. The data shown represent the mean±SD of three independent experiments. Significant differences relative to treatment with peptide are indicated as follows: *p<0.01, p<0.001, *p<0.0001, **p<0.00001, *p<0.000001, **p<0.0000001, ***p<0.00000001, ******p<0.000000001.

As shown in FIG. 7, Panel A, left sub-panel and FIG. 7, Panel B, top left sub-panel), Alix expression in EVs from MCF-7 cells were significantly decreased in PEG-SMRwt-CLU, SMRwt-CPP and MKT-077 treated cells. However, as shown in FIG. 7, Panel B, top left sub-panel, treatment of MCF-7 cells with Omeprazole or DMA were not accompanied by significant reductions in Alix expression. Vimentin expression in EVs from MCF-7 cells was significantly decreased for all treatments (PEG-SMRwt-Clu, SMRwt-CPP, MKT-077, omeprazole and DMA) relative to the negative controls (PEG-SMRmut-Clu and SMRmut-CPP) (FIG. 7, Panel B, middle left sub-panel. Mortalin expression in MCF-7 EVs was only significantly decreased following treatment with PEG-SMRwt-Clu peptide or MKT-077, however, no significant changes in mortalin expression were observed following treatment with SMRwt-CPP, Omeprazole, or DMA (FIG. 7, Panel B, bottom left sub-panel).

In MDA-MB-231 cells (FIG. 7, Panel A, middle top sub-panel and FIG. 7, Panel B, middle top sub-panel), Alix expression in MDA-MB-231 EVs was found to be significantly decreased in cells treated with PEG-SMRwt-Clu and SMRwt-CPP, however, no significant changes were observed following treatment with the three mortalin inhibitors. Vimentin expression was significantly decreased following treatment with PEG-SMRwt-Clu, SMRwt-CPP and DMA, however, no significant change was observed following treatment with MKT-077 or omeprazole (FIG. 7, Panel B, middle top sub-panel). Mortalin expression was significantly decreased following treatment with PEG-SMRwt-Clu and SMRwt-CPP treatment, and to a lesser extent following DMA treatment (FIG. 7, Panel B, middle bottom sub-panel. No significant change was observed following treatment of MDA-MB-231 cells with MKT-077 or omeprazole treatment.

In K562 cells (FIG. 7, Panel A, top right sub-panel and FIG. 7, Panel B, top right sub-panel), Alix expression in K562 EVs was significantly decreased following treatment with PEG-SMRwt-Clu, SMRwt-CPP, MKT-077, omeprazole and DMA. In contrast, vimentin expression in K562 EVs was significantly increased following treatment with MKT-077, Omeprazole and DMA, however, no significant changes in vimentin expression were observed following treatment with any of the wild-type or mutant SMR peptides (FIG. 7, Panel B, middle right sub-panel). Mortalin expression was significantly decreased following treatment with PEG-SMRwt-Clu, SMRwt-CPP, MKT-077, omeprazole and DMA. Taken together, the data from FIGS. 6 and 7 indicate that EV numbers and EV protein contents are modulated differently depending on the specific treatment.

Figure 8:
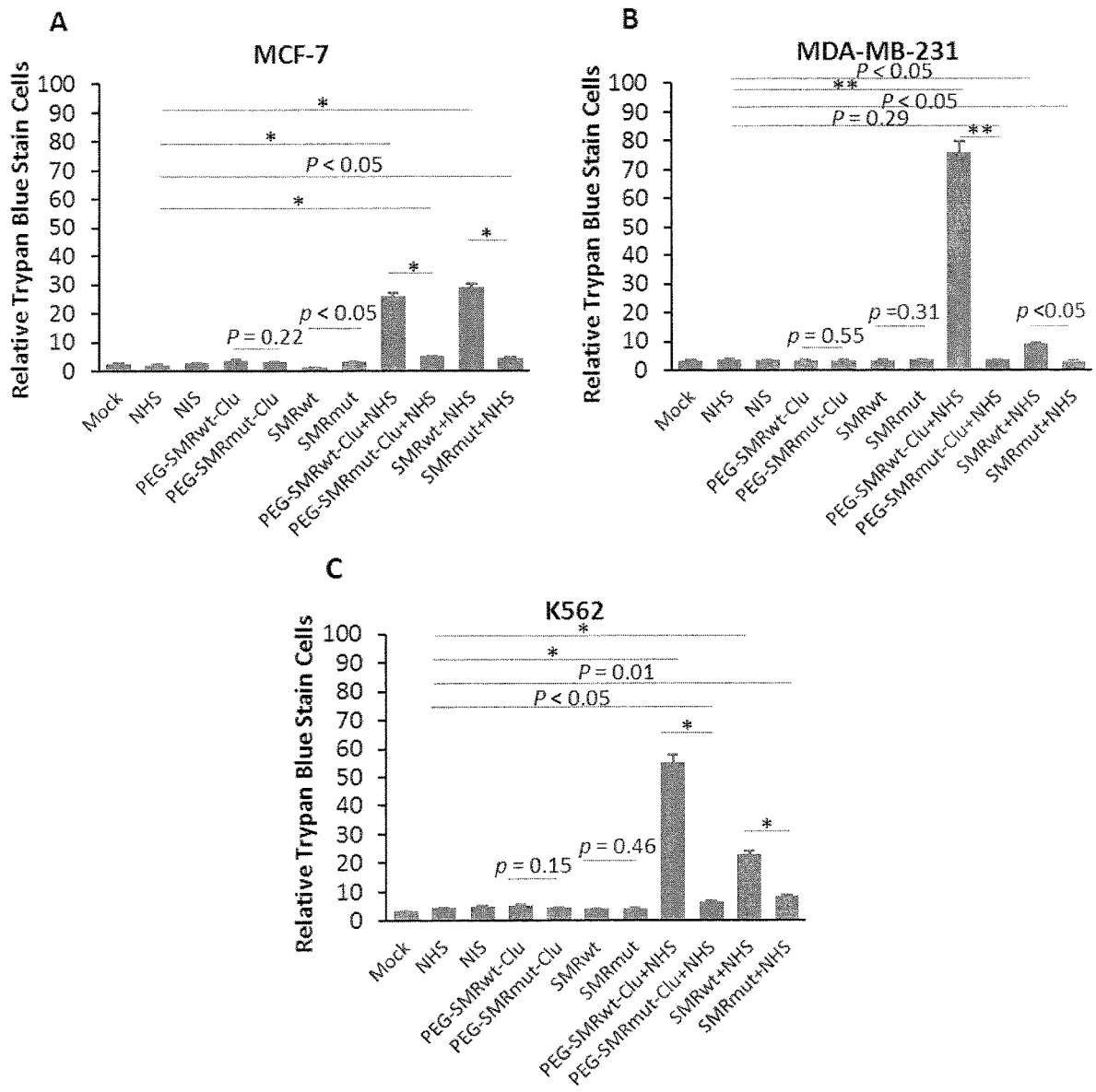
FIG. 8 shows that in the presence of NHS, PEG-SMRwt-Clu and SMRwt-CPP peptides SMRwt peptides block secretion of mortalin and exosomes and induce complement-mediated cytotoxicity in K562, MCF-7 and MDA-MB-231 cultures. Cells were treated with 280 nM PEG-SMRwt-Clu peptide or 560 nM SMRwt-CPP peptide alone for 60 min at 37° C., followed by treatment with 1 µg/mL anti-CXCR4 antibody and 50 µL NHS or NIS for additional 60 min at 37° C. PEG-SMRmut-Clu peptide and SMRmut-CPP peptide were used as negative controls. The percentage of stained (dead) cells is representative of 3 independent experiments. Panels A-C show relative levels of cells surviving a complement attack as determined by trypan blue exclusion. Panel A shows percent cell survival following treatment of MCF-7 cells (as indicated); Panel B shows percent cell survival following treatment of MDA-MB-231 cells; and Panel C shows percent cell survival following treatment of K562 cells. Cytotoxicity was not observed in cells treated with SMR peptides alone. Error bars represent mean+SD of four independent experiments. Significant differences relative to PEG-SMRwt-Clu peptide and SMRwt-CPP peptide are indicated as follows:*p<0.01, **p<0.001.

Example 6: SMRwt Peptides Block Mortalin-Driven Exosome Release of Complement-Dependent Cytotoxicity Mortalin has been shown to bind complement factor C9 and play a major role in development of resistance to complement-dependent cytotoxicity via mortalin induced exocytosis of the membrane attack complex (MAC) via EVs (Pilzer et al., Intl. Immunol., (2005) 17(9): p. 1239-1248). Therefore, it was of interest to see whether SMR peptide driven mortalin sequestration and functional disruption increases cell sensitivity to complement-induced cell death. Accordingly, MCF-7, MDA-MB-231, and K562 cells were treated with 280 nM PEG-SMRwt-Clu peptide or 560 nM SMRwt-CPP peptide alone for 60 min at 37° C., followed by treatment with 1 µg/mL anti-CXCR4 antibody and 50 µL normal human serum (NHS; as a source of complement) or normal heat-inactivated (human) serum (NIS) for an additional 60 min at 37° C. (FIG. 8). PEG-SMRmut-Clu peptide and SMRmut-CPP peptide were used as negative controls. The percentage of stained (dead) cells was determined by trypan blue exclusion and is representative of 3 independent experiments.

In the presence of functional complement (NHS), both of the SMRwt peptides significantly induced cell death. More specifically, in MCF-7 cells treated with PEG-SMRwt-Clu, cell death increased from 2.1% under complement-negative conditions (bar 4) to 26% under complement-positive conditions (bar 8)(FIG. 8, Panel A); likewise, in MCF-7 cells treated with SMRwt-CPP, cell death increased from 2.1% under complement-negative conditions (bar 6) to 29% under complement-positive conditions (bar 10) (FIG. 8, Panel A). These effects were abolished in the presence of complement when upon treatment with the SMRmutant peptides (bars 9, 11) (FIG. 8, Panel A).

In MDA-MB-231 cells treated with PEG-SMRwt-Clu, cell death increased from 3.6% under complement-negative conditions (bar 4) to 76% under complement-positive conditions (bar 8)(FIG. 8, Panel B); likewise, in MDA-MB-231 cells treated with SMRwt-CPP, cell death increased from 3.6% under complement-negative conditions (bar 6) to 9% under complement-positive conditions (bar 10) (FIG. 8, Panel B). These effects were abolished in the presence of complement when upon treatment with the SMRmutant peptides (bars 9, 11) (FIG. 8, Panel B).

In K562 cells treated with PEG-SMRwt-Clu, cell death increased from 4.3% under complement-negative conditions (bar 4) to 55% under complement-positive conditions (bar 8)(FIG. 8, Panel C); likewise, in K562 cells treated with SMRwt-CPP, cell death increased from 4.3% under complement-negative conditions (bar 6) to 23% under complement-positive conditions (bar 10) (FIG. 8, Panel C). These effects were abolished in the presence of complement when upon treatment with the SMRmutant peptides (bars 9, 11) (FIG. 8, Panel C).

Taken together, these data show that SMR-induced mortalin sequestration and functional disruption is linked to complement-mediated sensitivity and cell death. Specifically, blocking mortalin function renders or enhances cell sensitivity to complement-mediated cytotoxicity. Not wishing to be bound by theory, it is believed that such enhanced cell sensitivity and cell death may reduce the amount of viral production and spread.

Example 7: Mortalin Small Interfering RNA (siRNA) Reduces EV Secretion and Induces Complement-Mediated Cytotoxicity siRNA knockdown of mortalin expression was employed to further evaluate the role of mortalin in reducing EV secretion and protecting cells from complement-mediated cytotoxicity. Briefly, MCF-7, MDA-MB-231 and K562 cells were cultured in exosome-free media at 37° C. for 24 hr. The cells were then transfected with a vector expressing double-stranded mortalin siRNAs (Shelton et al., J Virol (2012) 86(1): p. 406-19; Huang et al., Oncotarget (2017) 8(7): p. 11302-11315). Negative control cells were transfected with a vector expressing a double-stranded siRNA predicted not to target any known vertebrate gene.

Figure 9:
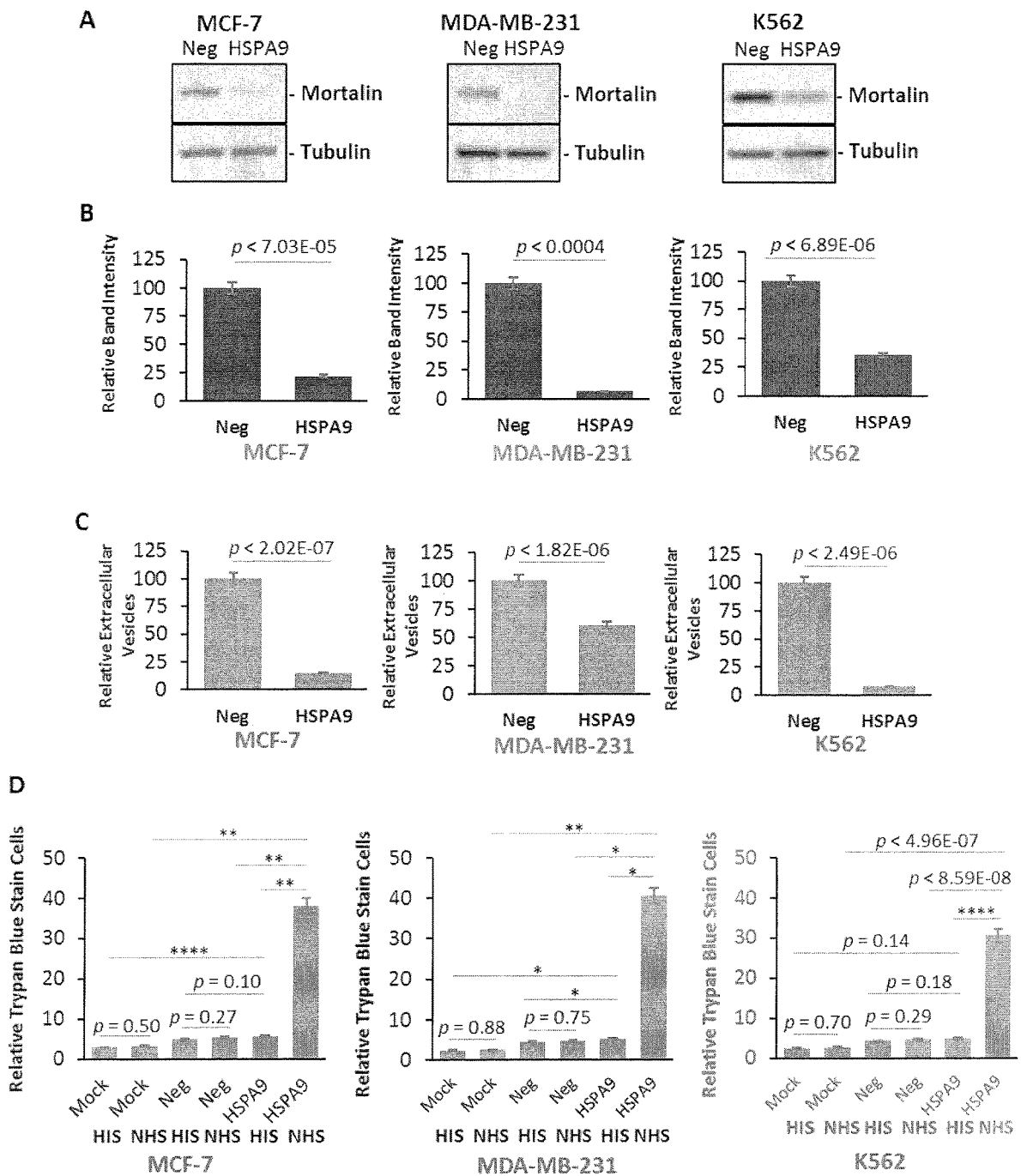
FIG. 9 shows that knockdown of mortalin expression induced complement-mediated cytotoxicity in K562, MCF-7 and MDA-MB-231 cell cultures. Cells were transfected with a vector expressing double-stranded mortalin siRNAs. Panel A shows detection of mortalin and a-tubulin following SDS-PAGE/Western blot analysis using anti-mortalin and anti-a-tubulin antibodies; Panel B shows the relative band intensities corresponding to the detected products in Panel A; Panel C shows the relative numbers of exosomes released by MCF-7, MDA-MB-231 and K562 cells as determined by NanoSight measurement; Panel D shows that siRNA-mediated knockdown of mortalin expression (HSPA9) induced complement-mediated cytotoxicity in the presence of normal human serum (NHS), but not in the presence of heat-inactivated serum (HIS), nor in mock-transfected cells or in cells expressing non-mortalin siRNAs ("Neg" means an siRNA predicted not to target any known vertebrate gene)) regardless of the presence or absence of NHS. Significant differences relative to siRNA-Neg transfected cells with NHS and mortalin siRNA transfected cells treated with NHS are indicated as follows: *p<0.01, **p<0.001.

Detection of mortalin protein in cells was measured by SDS-PAGE/Western blot analysis using anti-mortalin and anti-a-tubulin (internal control) antibodies (FIG. 9, Panel A). Quantitative results from Western blots were obtained by densitometry analysis of relative band intensities (FIG. 9, Panel B). Compared to the levels of mortalin expression in cells transfected with the negative control, transfection of the mortalin-targeted siRNA resulted in mortalin expression levels of: 21.86% in MCF-7 (FIG. 9, Panel B, left sub-panel), 6.28% in MDA-MB-231 (FIG. 9, Panel B, middle sub-panel) and 35.3% in K562 (FIG. 9, Panel C, right sub-panel).

In addition, EVs were isolated from the cell culture supernatants, and analyzed for concentration, and size distribution via NanoSight LMl0 Nanoparticle Tracking Analysis (NT A). With NT A, particles are automatically tracked and sized, based on Brownian motion and the associated diffusion coefficient. Before analysis of the samples by NTA, it was determined that salt aggregates from PBS did not contribute to background and that equipment was free of contaminant particles.

The results of this analysis are shown in FIG. 9, Panel C. In MCF-7 cells treated with the siRNA-Neg control, the cell culture supernatant was found to contain $3.91 \times 10^9$ particles/mL, while the mortalin siRNA treated cells were found to contain $5.79 \times 10^8$ particles/mL ($p<2.02E-07$)(FIG. 9, Panel C, left sub-panel). In MDA-MB-231 cells treated with the siRNA-Neg control, the cell culture supernatant was found to contain $5.71 \times 10^9$ particles/ml, while the mortalin siRNA treated cells were found to contain 3 $0.46 \times 10^9$ particles/mL ($p<1.82E-06$)(FIG. 9, Panel C, middle sub-panel). In K562 cells treated with the siRNA-Neg control, the cell culture supernatant was found to contain $3.44 \times 10^9$ particles/mL, while the mortalin siRNA treated cells were found to contain $2.58 \times 10^8$ particles/mL ($p<2.49E-06$)(FIG. 9, Panel C, right sub-panel). In all three cultures, NTA estimated the size of the EVs to be in the range of 30 to 47 nm (data not shown).

To further validate the ability of mortalin neutralization to render or enhance complement-mediated cytotoxicity, MCF-7, MDA-MB-231 and K562 cells were transfected with vectors expressing mortalin siRNAs or negative control siRNAs, incubated for 72 hours at 37° C., treated with anti-CXCR4 antibody for 30 minutes at 4° C. followed by incubation with either NHS or NIS for 60 minutes at 37° C. The data from these experiments indicated that silencing of mortalin expression resulted in mortalin-mediated protection of cells from complement-dependent cytotoxicity at 38.02% relative-to the negative control in MCF-7 cells (FIG. 9, Panel D, left sub-panel), at 40.55% relative to the negative control in MDA-MB-231 cells (FIG. 9, Panel D, middle sub-panel) and at 30.54% relative to the negative control in K562 cells (FIG. 9, Panel D, right subpanel).

Example 8: Inhibitory Activity of the VI-SMR Peptides

The VI-SMR peptides are tested for binding and/or functional activities via binding assays, infectivity assays and the like. A VI-SMR peptide-containing composition is evaluated for coronavirus binding activity using a variety of SARS-CoV-2 S protein-, SARS-CoV-2 S1 subunit (receptor binding domain, RBD) protein-, and/or ACE2 protein reagents. These reagents are His-tagged, Fe-tagged, A vi-tagged, or biotin-labeled in order to facilitate detection of binding on microtiter plates and the like using suitable colorimetric, chemiluminescent substrates (BPS Bioscience, San Diego, Calif.).

A functional assay is employed to evaluate the ability of the VI-SMR peptides to inhibit SARS-CoV-2 replication. The functional assays described below further allow for the generation of dose-response curves reflecting the degree of CoV-2 inhibition, including IC50 determinations for a given VI-SMR peptide.

In one assay, a VI-SMR peptide is tested for inhibitory activity by an in vitro plaque reduction assay using SARS-CoV-2 infected Vero E6 cells, a monkey kidney cell line, which is known to express the ACE2 receptor. Briefly, Vero E6 cells are plated onto 12-well tissue culture plates and incubated overnight to allow for adherence to the plates. Serial dilutions of VI-SMR peptide in cell maintenance media are then incubated with a defined amount of SARS-CoV-2 for one hour in the absence of Vero E6 cells. Negative control solutions include SARS-CoV-2 incubated for 1 hr in cell maintenance media without VI-SMR peptide or cells. Following the one hour incubation, the cell maintenance media is removed from the Vero E6 seeded plates and replaced with the pre-incubated solutions of VI-SMR peptide/SARS-CoV-2/cell media (test) or SARS-CoV-2/cell media (negative control). The cells are then incubated for 1 hr to allow adsorption of virus to the cells. Following the 1 hr incubation, the suspension is removed and methylcellulose overlays containing matched concentrations of VI-SMR peptide are added to each well. The plates are incubated for 3 days, inactivated and then stained with crystal violet stain. Dose response curves are then generated based on the degree of replication inhibition in each well compared to the corresponding negative controls (i.e., absence of VI-SMR peptide).

In another assay, a VI-SMR peptide is tested for inhibitory activity using lentivirus-based, VSV-based or MuLV-based virus particles pseudotyped with a CoV Spike (S) protein, such as SARS-CoV-2 S protein, and operably linked to a luciferase reporter. More particularly, this assay evaluates the ability of VI-SMR peptide to block expression of the luciferase reporter in ACE2-expressing cells infected with the S/S1-pseudotyped lentivirus reporter. A "bald" or non-pseudotyped control containing the luciferase reporter alone can be used as a negative control.

ACE2-expressing cells or cell lines are infected with the pseudotyped or non-pseudotyped virus particles in the presence of increasing concentrations of VI-SMR peptide. When using cells exhibiting low or no ACE2 expression, the pseudotyped and/or non-pseudotyped virus particles are co-infected with an expression construct, such as replication-defective HIV-1 particles engineered to express human ACE2. A lentivirus-based luciferase reporter system for carrying out this assay includes pseudotyped (CoV-2 S protein) lentivirus reporters, non-pseudotyped lentivirus reporters (negative control), and ACE2-expressing lentiviruses (BPS Bioscience, San Diego, Calif., BPS #s 79942, 79943 and 79944). Additional reagents and cell lines for carrying out the above experiments are obtained from BPS Bioscience (San Diego, Calif.) and Creative Biogene (Shirley, N.Y.).

Example 9: In Vivo Animal Model for Evaluating Therapeutic Efficacy

A major objective in treating Covid patients is to reduce viral loads and prevent or reduce the severity of the cytokine storm and its potentially lethal effects. A number of cytokines with anti-inflammatory properties are responsible for the cytokine storm, such as IL-10 and transforming growth factor β (TGF-β). Each cytokine acts on a different part of the inflammatory response. For example, products of the Th2 immune response suppress the Th1 immune response and vice versa. By resolving the associated inflammation, one can minimize collateral damage to surrounding cells, with little or no long-term damage to the patient. Accordingly, in addition to using the VI-SMR peptides described herein to inhibit the viral infection, the VI-SMR peptides may be administered alone or in combination with one or more active agents can be used to inhibit the cytokine storm.

To facilitate a determination of effective dosages and administration protocols for the VI-SMR peptides of the present application, an in vivo SARS-CoV-2 Syrian hamster model will be employed prior to human clinical trials. This study will address key aspects of SARS-CoV-2 pathology following VI-SMR peptide delivery, including evaluation of viral loads and alleviation of the occurrence and severity of downstream effects, including the cytokine storm associated with SARS-CoV-2 infections. Syrian hamsters are permissive to SARS-CoV-2 and develop mild lung disease similar to the disease observed in early-stage COVID-19 patients.

Briefly, 6-8 week old female Syrian hamsters are anesthetized with ketamine/xylazine/atropine and inoculated intranasally (twice daily) with 50 $\mu$L containing about $1 \times 10^5$ $TCID_{50}$ (median tissue culture infectious dose) of a SARS-CoV-2 strain (day 0). Beginning 2 h before infection, animals are treated twice daily with a VI-SMR peptide (e.g., VGFPVAAVGFPV (SEQ ID NO: 2) or VGFPVAAVGFPVGRKKRRQRRRPPQ (SEQ ID NO: 4)), a mutant VI-SMR peptide (e.g., AGFPVAAAGFPV (SEQ ID NO: 52) or AGFPVAAAGFPVGRKKRRQRRRPPQ (SEQ ID NO: 50); negative control) and/or the vehicle used in the VI-SMR peptide formulation (negative control). The peptide may be delivered intranasally, by intratracheal instillation or by aerosol inhalation. Hamsters are monitored for appearance, behavior and weight. At day 2 post infection (pi) (day 3), 6 h following the 5th dose, hamsters are euthanized by IP injection of 500 $\mu$L Dolethal (200 mg/mL sodium pentobarbital, Vétoquinol SA). Lungs are collected and viral RNA and infectious virus are quantified by RT-qPCR and end-point virus titration, respectively. In addition, blood samples and lung tissue samples are collected and evaluated for cytokine levels and pharmacokinetic analysis of the VI-SMR peptides. The results of these studies show at least a 2 or 3 $\log_{10}$ reduction in viral RNA copies per mg of lung tissue compared to the vehicle. Additionally, the results show a reduction of at least 10%, 20%, 50% or 80% in cytokine levels for one or more of IL-6, IL-1β, IL-2, IL-10, IFN-γ, TNF-α, and GM-CSF.

While various embodiments have been described above, it should be understood that such disclosures have been presented by way of example only and are not limiting. Thus, the breadth and scope of the subject compositions and methods should not be limited by any of the above-described exemplary embodiments, but should be defined only in accordance with the following claims and their equivalents.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

What is claimed is:

1. A method for treating a SARS-CoV-2 infection, comprising:
   administering to a subject in need of such treatment an effective amount of a pharmaceutical composition comprising a virus-inhibiting secretion modifying region (VI-SMR) peptide comprising an SMR peptide from HIV-1 Nef in combination with a cell penetrating peptide (CPP), a Clusterin-binding peptide (Clu-BP), or both.

2. The method of claim 1, wherein the SMR peptide comprises the amino acid sequence of VGFPVAAVGFPV (SEQ ID NO: 2), VGFPVAAVGFPVGRKKRRQRRRPPQ (SEQ ID NO: 4) or VGFPVAAVGFPVAAHPLSKHPYWSQPAAHPLSKHPYWSQP (SEQ ID NO: 48).

3. The method of claim 1, wherein the VI-SMR peptide comprises an anti-SARS-CoV-2 anti-fusogenic (AF) peptide, an anti-SARS-CoV-2 viral attachment inhibitor (VAI) peptide, a mitochondrial targeting (Mito-T) peptide, or combination thereof.

4. The method of claim 1, wherein the VI-SMR peptide is pegylated, conjugated to a fatty acid, or both.

5. The method of claim 1, wherein the pharmaceutical composition comprises a dimeric or multimeric VI-SMR peptide.

6. The method of claim 1, wherein the pharmaceutical composition is administered in combination with one or more antiviral agents targeting SARS-2-CoV-2.

7. The method of claim 1, wherein the VI-SMR peptide is loaded into an exosome that is administered into the subject infected with SARS-CoV-2.

8. A method for treating a SARS-CoV-2 infection, comprising:
   administering to a subject in need of such treatment a pharmaceutical composition comprising an effective amount of an anti-SARS-CoV-2 peptide comprising an SMR peptide from HIV-1 Nef fused to a CPP, Clu-BP, or both, optionally wherein the anti-SARS-CoV-2 peptide is administered in combination with a mortalin inhibitor, an anti-SARS-CoV-2 AF peptide, an anti-SARS-CoV-2 VAI peptide, or combination thereof.

9. The method of claim 8, wherein the pharmaceutical composition comprising the anti-SARS-CoV-2 peptide is administered in combination with an AF peptide or VAI peptide,
   wherein the anti-SARS-CoV-2 peptide is administered independent of the AF peptide or the VAI peptide or wherein the anti-SARS-CoV-2 peptide is administered as a single peptide fused to the anti-SARS-CoV-2 peptide or the VI-SMR peptide.

10. The method of claim 8, wherein the anti-SARS-CoV-2 peptide is pegylated, conjugated to a fatty acid, or both.

11. The method of claim 8, wherein the pharmaceutical composition comprises a dimeric or multimeric anti-SARS-CoV-2 peptide.

12. The method of claim 8, wherein the pharmaceutical composition is administered in combination with one or more antiviral agents inhibiting SARS-2-CoV-2 infections.

* * * * *

SEQUENCE LISTING

<160> NUMBER OF SEQ ID NOS: 52

<210> SEQ ID NO 1
<211> LENGTH: 5
<212> TYPE: PRT
<213> ORGANISM: Artificial Sequence
<220> FEATURE:
<223> OTHER INFORMATION: Synthetic: SMR peptide

<400> SEQUENCE: 1

Val Gly Phe Pro Val
1               5

<210> SEQ ID NO 2
<211> LENGTH: 12
<212> TYPE: PRT
<213> ORGANISM: Artificial Sequence
<220> FEATURE:
<223> OTHER INFORMATION: Synthetic: SMR peptide

<400> SEQUENCE: 2

Val Gly Phe Pro Val Ala Ala Val Gly Phe Pro Val
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Synthetic: CPP peptide

<400> SEQUENCE: 3

Gly Arg Lys Lys Arg Arg Gln Arg Arg Arg Pro Pro Gln
1               5                   10

<210> SEQ ID NO 4
<211> LENGTH: 25
<212> TYPE: PRT
<213> ORGANISM: Artificial Sequence
<220> FEATURE:
<223> OTHER INFORMATION: Synthetic: SMR-CPP peptide

<400> SEQUENCE: 4

Val Gly Phe Pro Val Ala Ala Val Gly Phe Pro Val Gly Arg Lys Lys
1               5                   10                  15

Arg Arg Gln Arg Arg Arg Pro Pro Gln
            20                  25

<210> SEQ ID NO 5
<211> LENGTH: 12
<212> TYPE: PRT
<213> ORGANISM: Artificial Sequence
<220> FEATURE:
<223> OTHER INFORMATION: Synthetic: Clu-BP peptide

<400> SEQUENCE: 5

His Pro Leu Ser Lys His Pro Tyr Trp Ser Gln Pro
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic: Clu-BP peptide

<400> SEQUENCE: 6

```
Asn Thr Tyr Trp Ser Gln Leu Leu His Phe Gln Thr
1               5                   10
```

<210> SEQ ID NO 7
<211> LENGTH: 12
<212> TYPE: PRT
<213> ORGANISM: Artificial Sequence
<220> FEATURE:
<223> OTHER INFORMATION: Synthetic: Clu-BP peptide

<400> SEQUENCE: 7

```
Ser His Ala Leu Pro Leu Thr Trp Ser Thr Ala Ala
1               5                   10
```

<210> SEQ ID NO 8
<211> LENGTH: 29
<212> TYPE: PRT
<213> ORGANISM: Artificial Sequence
<220> FEATURE:
<223> OTHER INFORMATION: Synthetic: Mito-T peptide

<400> SEQUENCE: 8

```
Met Ser Val Leu Thr Pro Leu Leu Leu Arg Gly Leu Thr Gly Ser Ala
1               5                   10                  15

Arg Arg Leu Pro Val Pro Arg Ala Lys Ile His Ser Leu
            20                  25
```

<210> SEQ ID NO 9
<211> LENGTH: 33
<212> TYPE: PRT
<213> ORGANISM: Artificial Sequence
<220> FEATURE:
<223> OTHER INFORMATION: Synthetic: Mito-T peptide

<400> SEQUENCE: 9

```
Met Leu Ser Asn Leu Arg Ile Leu Leu Asn Lys Ala Ala Leu Arg Lys
1               5                   10                  15

Ala His Thr Ser Met Val Arg Asn Phe Arg Tyr Gly Lys Pro Val Gln
            20                  25                  30

Cys
```

<210> SEQ ID NO 10
<211> LENGTH: 18
<212> TYPE: PRT
<213> ORGANISM: Artificial Sequence
<220> FEATURE:
<223> OTHER INFORMATION: Synthetic: Mito-T peptide

<400> SEQUENCE: 10

```
Met Leu Ser Leu Arg Gln Ser Ile Arg Phe Phe Lys Pro Ala Thr Arg
1               5                   10                  15

Thr Leu
```

<210> SEQ ID NO 11
<211> LENGTH: 16
<212> TYPE: PRT
<213> ORGANISM: Artificial Sequence
<220> FEATURE:
<223> OTHER INFORMATION: Synthetic: Mito-T peptide

<400> SEQUENCE: 11

```
Arg Gln Ile Lys Ile Trp Phe Gln Asn Arg Arg Met Lys Trp Lys Lys
1               5                   10                  15
```

<210> SEQ ID NO 12
<211> LENGTH: 34
<212> TYPE: PRT
<213> ORGANISM: Artificial Sequence
<220> FEATURE:
<223> OTHER INFORMATION: Synthetic: Mito-T peptide

<400> SEQUENCE: 12

```
Met Phe Ser Tyr Leu Pro Arg Tyr Pro Leu Arg Ala Ala Ser Ala Arg
1               5                   10                  15

Ala Leu Val Arg Ala Thr Arg Pro Ser Tyr Arg Ser Ala Leu Leu Arg
            20                  25                  30

Tyr Gln
```

<210> SEQ ID NO 13
<211> LENGTH: 20
<212> TYPE: PRT
<213> ORGANISM: Artificial Sequence
<220> FEATURE:
<223> OTHER INFORMATION: Synthetic: Mito-T peptide

<400> SEQUENCE: 13

```
Met Ala Ala Trp Met Arg Ser Leu Phe Ser Pro Leu Lys Lys Leu Trp
1               5                   10                  15

Ile Arg Met His
            20
```

<210> SEQ ID NO 14
<211> LENGTH: 13
<212> TYPE: PRT
<213> ORGANISM: Artificial Sequence
<220> FEATURE:
<223> OTHER INFORMATION: Synthetic: Mito-T peptide

<400> SEQUENCE: 14

```
Met Lys Leu Leu Trp Arg Leu Ile Leu Ser Arg Lys Trp
1               5                   10
```

<210> SEQ ID NO 15
<211> LENGTH: 14
<212> TYPE: PRT
<213> ORGANISM: Artificial Sequence
<220> FEATURE:
<223> OTHER INFORMATION: Synthetic: Mito-T peptide

<400> SEQUENCE: 15

```
Met Trp Trp Arg Arg Ser Arg Thr Asn Ser Leu Arg Tyr Thr
1               5                   10
```

<210> SEQ ID NO 16
<211> LENGTH: 16
<212> TYPE: PRT
<213> ORGANISM: Artificial Sequence
<220> FEATURE:
<223> OTHER INFORMATION: Synthetic: Mito-T peptide

<400> SEQUENCE: 16

```
Met Leu Phe Arg Leu Arg Arg Ser Val Arg Leu Arg Gly Leu Leu Ala
1               5                   10                  15
```

<210> SEQ ID NO 17
<211> LENGTH: 20
<212> TYPE: PRT
<213> ORGANISM: Artificial Sequence
<220> FEATURE:

-continued

<223> OTHER INFORMATION: Synthetic: Mito-T peptide

<400> SEQUENCE: 17

Met Trp Thr Leu Gly Arg Arg Ala Val Ala Gly Leu Leu Ala Ser Pro
1               5                   10                  15

Ser Pro Ala Gln
            20

<210> SEQ ID NO 18
<211> LENGTH: 20
<212> TYPE: PRT
<213> ORGANISM: Artificial Sequence
<220> FEATURE:
<223> OTHER INFORMATION: Synthetic: Mito-T peptide

<400> SEQUENCE: 18

Arg Arg Ile Val Val Leu His Gly Tyr Gly Ala Val Lys Glu Val Leu
1               5                   10                  15

Leu Asn His Lys
            20

<210> SEQ ID NO 19
<211> LENGTH: 22
<212> TYPE: PRT
<213> ORGANISM: Artificial Sequence
<220> FEATURE:
<223> OTHER INFORMATION: Synthetic: Mito-T peptide

<400> SEQUENCE: 19

Met Leu Ser Leu Arg Gln Asp Ile Arg Phe Phe Lys Pro Ala Thr Arg
1               5                   10                  15

Thr Leu Cys Ser Ser Arg
            20

<210> SEQ ID NO 20
<211> LENGTH: 36
<212> TYPE: PRT
<213> ORGANISM: Artificial Sequence
<220> FEATURE:
<223> OTHER INFORMATION: Synthetic: anti-fusion peptide

<400> SEQUENCE: 20

Ser Leu Asp Gln Ile Asn Val Thr Phe Leu Asp Leu Glu Tyr Glu Met
1               5                   10                  15

Lys Lys Leu Glu Glu Ala Ile Lys Lys Leu Glu Glu Ser Tyr Ile Asp
            20                  25                  30

Leu Lys Glu Leu
            35

<210> SEQ ID NO 21
<211> LENGTH: 35
<212> TYPE: PRT
<213> ORGANISM: Artificial Sequence
<220> FEATURE:
<223> OTHER INFORMATION: Synthetic: anti-fusion peptide

<400> SEQUENCE: 21

Ile Ser Gly Ile Asn Ala Ser Val Val Asn Ile Gln Lys Glu Ile Asp
1               5                   10                  15

Arg Leu Asn Glu Val Ala Lys Asn Leu Asn Glu Ser Leu Ile Asp Leu
            20                  25                  30

Gln Glu Leu
        35

```
<210> SEQ ID NO 22
<211> LENGTH: 36
<212> TYPE: PRT
<213> ORGANISM: Artificial Sequence
<220> FEATURE:
<223> OTHER INFORMATION: Synthetic: anti-fusion peptide

<400> SEQUENCE: 22

Ile Ser Gly Ile Asn Ala Ser Val Val Asn Ile Gln Lys Glu Ile Asp
1               5                   10                  15

Arg Leu Asn Glu Val Ala Lys Asn Leu Asn Glu Ser Leu Ile Asp Leu
            20                  25                  30

Gln Glu Leu Lys
        35

<210> SEQ ID NO 23
<211> LENGTH: 36
<212> TYPE: PRT
<213> ORGANISM: Artificial Sequence
<220> FEATURE:
<223> OTHER INFORMATION: Synthetic: anti-fusion peptide

<400> SEQUENCE: 23

Asp Ile Ser Gly Ile Asn Ala Ser Val Val Asn Ile Gln Lys Glu Ile
1               5                   10                  15

Asp Arg Leu Asn Glu Val Ala Lys Asn Leu Asn Glu Ser Leu Ile Asp
            20                  25                  30

Leu Gln Glu Leu
        35

<210> SEQ ID NO 24
<211> LENGTH: 6
<212> TYPE: PRT
<213> ORGANISM: Artificial Sequence
<220> FEATURE:
<223> OTHER INFORMATION: Synthetic: viral attachment inhibitor peptide

<400> SEQUENCE: 24

Tyr Lys Tyr Arg Tyr Leu
1               5

<210> SEQ ID NO 25
<211> LENGTH: 18
<212> TYPE: PRT
<213> ORGANISM: Artificial Sequence
<220> FEATURE:
<223> OTHER INFORMATION: Synthetic: viral attachment inhibitor peptide

<400> SEQUENCE: 25

Phe Leu Asp Lys Phe Asn His Glu Ala Glu Asp Leu Phe Tyr Gln Ser
1               5                   10                  15

Ser Leu

<210> SEQ ID NO 26
<211> LENGTH: 31
<212> TYPE: PRT
<213> ORGANISM: Artificial Sequence
<220> FEATURE:
<223> OTHER INFORMATION: Synthetic: viral attachment inhibitor peptide

<400> SEQUENCE: 26

Glu Glu Gln Ala Lys Thr Phe Leu Asp Lys Phe Asn His Glu Ala Glu
1               5                   10                  15
```

```
Asp Leu Phe Tyr Gln Ser Ser Gly Leu Gly Lys Gly Asp Phe Arg
            20                  25                  30

<210> SEQ ID NO 27
<211> LENGTH: 12
<212> TYPE: PRT
<213> ORGANISM: Artificial Sequence
<220> FEATURE:
<223> OTHER INFORMATION: Synthetic: viral attachment inhibitor peptide

<400> SEQUENCE: 27

Gly Phe Leu Tyr Val Tyr Lys Gly Tyr Gln Pro Ile
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Synthetic: viral attachment inhibitor peptide

<400> SEQUENCE: 28

Phe Tyr Thr Thr Thr Gly Ile Gly Tyr Gln Pro Tyr
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Synthetic: viral attachment inhibitor peptide

<400> SEQUENCE: 29

Ser Thr Ser Gln Lys Ser Ile Val Ala Tyr Thr Met
1               5                   10

<210> SEQ ID NO 30
<211> LENGTH: 45
<212> TYPE: PRT
<213> ORGANISM: Artificial Sequence
<220> FEATURE:
<223> OTHER INFORMATION: Synthetic: viral attachment inhibitor peptide

<400> SEQUENCE: 30

Gly Gly Gly Tyr Ser Lys Ala Gln Lys Ala Gln Ala Lys Gln Ala Lys
1               5                   10                  15

Gln Ala Gln Lys Ala Gln Lys Ala Gln Ala Lys Gln Ala Lys Gln Ala
            20                  25                  30

Gln Lys Ala Gln Lys Ala Gln Ala Lys Gln Ala Lys Gln
        35                  40                  45

<210> SEQ ID NO 31
<211> LENGTH: 80
<212> TYPE: PRT
<213> ORGANISM: Artificial Sequence
<220> FEATURE:
<223> OTHER INFORMATION: Synthetic: viral attachment inhibitor peptide

<400> SEQUENCE: 31

Gly Ser His Met Gly Asp Ala Gln Asp Lys Leu Lys Tyr Leu Val Lys
1               5                   10                  15

Gln Leu Glu Arg Ala Leu Arg Glu Leu Lys Lys Ser Leu Asp Glu Leu
            20                  25                  30

Glu Arg Ser Leu Glu Glu Leu Glu Lys Asn Pro Ser Glu Asp Ala Leu
```

```
                35                  40                  45
Val Glu Asn Asn Arg Leu Asn Val Glu Asn Asn Lys Ile Ile Val Glu
    50                  55                  60

Val Leu Arg Ile Ile Leu Glu Leu Ala Lys Ala Ser Ala Lys Leu Ala
65                  70                  75                  80

<210> SEQ ID NO 32
<211> LENGTH: 15
<212> TYPE: PRT
<213> ORGANISM: Artificial Sequence
<220> FEATURE:
<223> OTHER INFORMATION: Synthetic: PEG-endo-cleavage-SMR peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 32

Asn Xaa Asn Val Gly Phe Pro Val Ala Ala Val Gly Phe Pro Val
1               5                   10                  15

<210> SEQ ID NO 33
<211> LENGTH: 27
<212> TYPE: PRT
<213> ORGANISM: Artificial Sequence
<220> FEATURE:
<223> OTHER INFORMATION: Synthetic: PEG-endo-cleavage-SMR-Clu-BP peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 33

Asn Xaa Asn Val Gly Phe Pro Val Ala Ala Val Gly Phe Pro Val His
1               5                   10                  15

Pro Leu Ser Lys His Pro Tyr Trp Ser Gln Pro
            20                  25

<210> SEQ ID NO 34
<211> LENGTH: 6
<212> TYPE: PRT
<213> ORGANISM: Artificial Sequence
<220> FEATURE:
<223> OTHER INFORMATION: Synthetic: endo-cleavage

<400> SEQUENCE: 34

Pro Leu Gly Leu Ala Gly
1               5

<210> SEQ ID NO 35
<211> LENGTH: 6
<212> TYPE: PRT
<213> ORGANISM: Artificial Sequence
<220> FEATURE:
<223> OTHER INFORMATION: Synthetic: endo-cleavage
<220> FEATURE:
<221> NAME/KEY: MOD_RES
<222> LOCATION: (4)..(4)
<223> OTHER INFORMATION: METHYLATION

<400> SEQUENCE: 35

Pro Leu Gly Cys Ala Gly
1               5

<210> SEQ ID NO 36
<211> LENGTH: 8
<212> TYPE: PRT
```

```
<213> ORGANISM: Artificial Sequence
<220> FEATURE:
<223> OTHER INFORMATION: Synthetic: endo-cleavage

<400> SEQUENCE: 36

Arg Pro Leu Ala Leu Trp Arg Ser
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic: endo-cleavage

<400> SEQUENCE: 37

Glu Ser Pro Ala Tyr Tyr Thr Ala
1               5

<210> SEQ ID NO 38
<211> LENGTH: 6
<212> TYPE: PRT
<213> ORGANISM: Artificial Sequence
<220> FEATURE:
<223> OTHER INFORMATION: Synthetic: endo-cleavage

<400> SEQUENCE: 38

Asp Pro Arg Ser Phe Leu
1               5

<210> SEQ ID NO 39
<211> LENGTH: 6
<212> TYPE: PRT
<213> ORGANISM: Artificial Sequence
<220> FEATURE:
<223> OTHER INFORMATION: Synthetic: endo-cleavage

<400> SEQUENCE: 39

Pro Pro Arg Ser Phe Leu
1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic: endo-cleavage

<400> SEQUENCE: 40

Arg Leu Gln Leu Lys Leu
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic: endo-cleavage
<220> FEATURE:
<221> NAME/KEY: MOD_RES
<222> LOCATION: (5)..(5)
<223> OTHER INFORMATION: ACETYLATION

<400> SEQUENCE: 41

Arg Leu Gln Leu Lys
1               5
```

```
<210> SEQ ID NO 42
<211> LENGTH: 4
<212> TYPE: PRT
<213> ORGANISM: Artificial Sequence
<220> FEATURE:
<223> OTHER INFORMATION: Synthetic: endo-cleavage
<220> FEATURE:
<221> NAME/KEY: misc_feature
<222> LOCATION: (2)..(3)
<223> OTHER INFORMATION: Xaa can be any naturally occurring amino acid

<400> SEQUENCE: 42

Arg Xaa Xaa Arg
1

<210> SEQ ID NO 43
<211> LENGTH: 4
<212> TYPE: PRT
<213> ORGANISM: Artificial Sequence
<220> FEATURE:
<223> OTHER INFORMATION: Synthetic: endo-cleavage
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa is Lys or Arg

<400> SEQUENCE: 43

Arg Xaa Xaa Arg
1

<210> SEQ ID NO 44
<211> LENGTH: 4
<212> TYPE: PRT
<213> ORGANISM: Artificial Sequence
<220> FEATURE:
<223> OTHER INFORMATION: Synthetic: endo-cleavage
<220> FEATURE:
<221> NAME/KEY: misc_feature
<222> LOCATION: (2)..(2)
<223> OTHER INFORMATION: Xaa is Glu or Asp

<400> SEQUENCE: 44

Ile Xaa Gly Arg
1

<210> SEQ ID NO 45
<211> LENGTH: 6
<212> TYPE: PRT
<213> ORGANISM: Artificial Sequence
<220> FEATURE:
<223> OTHER INFORMATION: Synthetic: endo-cleavage

<400> SEQUENCE: 45

Leu Val Pro Arg Gly Ser
1               5

<210> SEQ ID NO 46
<211> LENGTH: 24
<212> TYPE: PRT
<213> ORGANISM: Artificial Sequence
<220> FEATURE:
<223> OTHER INFORMATION: Synthetic: SMR-Clu-BP

<400> SEQUENCE: 46

Val Gly Phe Pro Val Ala Ala Val Gly Phe Pro Val His Pro Leu Ser
1               5                   10                  15
```

```
Lys His Pro Tyr Trp Ser Gln Pro
            20

<210> SEQ ID NO 47
<211> LENGTH: 26
<212> TYPE: PRT
<213> ORGANISM: Artificial Sequence
<220> FEATURE:
<223> OTHER INFORMATION: Synthetic: SMR-Clu-BP

<400> SEQUENCE: 47

Val Gly Phe Pro Val Ala Ala Val Gly Phe Pro Val Ala Ala His Pro
1               5                   10                  15

Leu Ser Lys His Pro Tyr Trp Ser Gln Pro
            20                  25

<210> SEQ ID NO 48
<211> LENGTH: 40
<212> TYPE: PRT
<213> ORGANISM: Artificial Sequence
<220> FEATURE:
<223> OTHER INFORMATION: Synthetic: SMR-Clu-BP

<400> SEQUENCE: 48

Val Gly Phe Pro Val Ala Ala Val Gly Phe Pro Val Ala Ala His Pro
1               5                   10                  15

Leu Ser Lys His Pro Tyr Trp Ser Gln Pro Ala Ala His Pro Leu Ser
            20                  25                  30

Lys His Pro Tyr Trp Ser Gln Pro
        35                  40

<210> SEQ ID NO 49
<211> LENGTH: 27
<212> TYPE: PRT
<213> ORGANISM: Artificial Sequence
<220> FEATURE:
<223> OTHER INFORMATION: Synthetic: SMRmut-Clu-BP
<220> FEATURE:
<221> NAME/KEY: misc_feature
<222> LOCATION: (2)..(2)
<223> OTHER INFORMATION: Xaa can be any naturally occurring amino acid

<400> SEQUENCE: 49

Asn Xaa Asn Ala Gly Phe Pro Val Ala Ala Ala Gly Phe Pro Val His
1               5                   10                  15

Pro Leu Ser Lys His Pro Tyr Trp Ser Gln Pro
            20                  25

<210> SEQ ID NO 50
<211> LENGTH: 25
<212> TYPE: PRT
<213> ORGANISM: Artificial Sequence
<220> FEATURE:
<223> OTHER INFORMATION: Synthetic: SMRmut-CPP

<400> SEQUENCE: 50

Ala Gly Phe Pro Val Ala Ala Ala Gly Phe Pro Val Gly Arg Lys Lys
1               5                   10                  15

Arg Arg Gln Arg Arg Pro Pro Gln
            20                  25

<210> SEQ ID NO 51
<211> LENGTH: 5
<212> TYPE: PRT
```

```
<213> ORGANISM: Artificial Sequence
<220> FEATURE:
<223> OTHER INFORMATION: Synthetic: SMRmut

<400> SEQUENCE: 51

Ala Gly Phe Pro Val
1               5

<210> SEQ ID NO 52
<211> LENGTH: 12
<212> TYPE: PRT
<213> ORGANISM: Artificial Sequence
<220> FEATURE:
<223> OTHER INFORMATION: Synthetic: SMRmut

<400> SEQUENCE: 52

Ala Gly Phe Pro Val Ala Ala Ala Gly Phe Pro Val
1               5                   10
```